(12) United States Patent
Ivosevic et al.

(10) Patent No.: US 10,537,495 B2
(45) Date of Patent: Jan. 21, 2020

(54) SYSTEM FOR CLOSED TRANSFER OF FLUIDS

(71) Applicant: Becton Dickinson and Company Limited, Dun Laoghaire (IE)

(72) Inventors: Milan Ivosevic, Kinnelon, NJ (US); Paul Paia Marici, Piscataway, NJ (US)

(73) Assignee: Becton Dickinson and Company Ltd., Dun Laoghaire (IE)

( * ) Notice: Subject to any disclaimer, the term of this patent is extended or adjusted under 35 U.S.C. 154(b) by 265 days.

(21) Appl. No.: 15/426,683

(22) Filed: Feb. 7, 2017

(65) Prior Publication Data

US 2017/0143587 A1    May 25, 2017

Related U.S. Application Data

(62) Division of application No. 14/204,428, filed on Mar. 11, 2014, now Pat. No. 9,597,260.

(60) Provisional application No. 61/895,168, filed on Oct. 24, 2013, provisional application No. 61/895,187, filed on Oct. 24, 2013, provisional application No.
(Continued)

(51) Int. Cl.
*A61J 1/20* (2006.01)
*A61M 39/14* (2006.01)
*A61M 39/12* (2006.01)
*A61M 39/10* (2006.01)

(52) U.S. Cl.
CPC ............. *A61J 1/2096* (2013.01); *A61J 1/201* (2015.05); *A61J 1/2048* (2015.05); *A61J 1/2082* (2015.05); *A61M 39/12* (2013.01); *A61M 39/14* (2013.01); *A61J 1/2055* (2015.05); *A61J 1/2065* (2015.05); *A61J 1/2072* (2015.05); *A61M 2039/1027* (2013.01); *A61M 2039/1044* (2013.01); *A61M 2039/1072* (2013.01); *Y10T 29/49217* (2015.01)

(58) Field of Classification Search
CPC ........ A61J 1/2096; A61J 1/201; A61J 1/2082; A61J 1/2048; A61J 1/2055; A61J 1/2065; A61J 1/2072; A61M 39/12; A61M 39/14
See application file for complete search history.

(56) References Cited

U.S. PATENT DOCUMENTS

| 3,047,178 | A | 7/1962 | Poitras et al. |
| 4,564,054 | A | 1/1986 | Gustavsson |

(Continued)

FOREIGN PATENT DOCUMENTS

| EP | 2462971 A1 | 6/2012 |
| JP | 5043056 | 8/1948 |

(Continued)

*Primary Examiner* — Timothy P. Kelly
(74) *Attorney, Agent, or Firm* — The Webb Law Firm

(57) ABSTRACT

A system for the closed transfer of fluids that provides substantially leak-proof sealing and pressure equalization during engagement of a cannula with a vial, during transfer of a substance from a vial chamber to a barrel chamber via the cannula, and during disengagement of the cannula from the vial is disclosed. The leak-proof sealing of the system substantially prevents leakage of both air and liquid during use of the system. The system of the present disclosure also permits pressure equalization between a vial and the system when the system is attached to the vial. The system is compatible with a needle and syringe assembly for accessing a medication contained within a vial for administering the medication to a patient.

3 Claims, 45 Drawing Sheets

Related U.S. Application Data

61/895,182, filed on Oct. 24, 2013, provisional application No. 61/787,674, filed on Mar. 15, 2013.

(56) References Cited

U.S. PATENT DOCUMENTS

| | | |
|---|---|---|
| 4,589,879 A | 5/1986 | Pearson |
| 4,673,404 A | 6/1987 | Gustavsson |
| 4,932,937 A | 6/1990 | Gustavsson et al. |
| 5,122,123 A * | 6/1992 | Vaillancourt ......... A61M 39/14 604/192 |
| 5,122,129 A | 6/1992 | Olson et al. |
| 5,211,638 A | 5/1993 | Dudar et al. |
| 5,280,876 A | 1/1994 | Atkins |
| 5,290,254 A | 3/1994 | Vaillancourt |
| 5,334,188 A | 8/1994 | Inoue et al. |
| 5,360,011 A | 11/1994 | McCallister |
| 5,395,348 A | 3/1995 | Ryan |
| 5,437,650 A | 8/1995 | Larkin et al. |
| 5,464,123 A | 11/1995 | Scarrow |
| 5,472,430 A | 12/1995 | Vaillancourt et al. |
| 5,478,328 A | 12/1995 | Silverman et al. |
| 5,487,728 A | 1/1996 | Vaillancourt |
| 5,507,733 A | 4/1996 | Larkin et al. |
| 5,509,911 A | 4/1996 | Cottone, Sr. et al. |
| 5,545,152 A | 8/1996 | Funderburk et al. |
| 5,607,392 A | 3/1997 | Kanner |
| 5,609,584 A | 3/1997 | Gettig et al. |
| 5,611,792 A | 3/1997 | Gustafsson |
| 5,647,845 A | 7/1997 | Haber et al. |
| 5,685,866 A | 11/1997 | Lopez |
| 5,807,347 A | 9/1998 | Bonaldo |
| 5,827,262 A | 10/1998 | Neftel et al. |
| 5,897,526 A | 4/1999 | Vaillancourt |
| 6,063,068 A | 5/2000 | Fowles et al. |
| 6,089,541 A | 7/2000 | Weinheimer et al. |
| 6,113,068 A | 9/2000 | Ryan |
| 6,113,583 A | 9/2000 | Fowles et al. |
| 6,132,404 A | 10/2000 | Lopez |
| 6,139,534 A | 10/2000 | Niedospial, Jr. et al. |
| 6,149,623 A | 11/2000 | Reynolds |
| 6,221,041 B1 | 4/2001 | Russo |
| 6,221,056 B1 | 4/2001 | Silverman |
| 6,238,372 B1 | 5/2001 | Zinger et al. |
| 6,280,430 B1 | 8/2001 | Neftel et al. |
| 6,299,131 B1 * | 10/2001 | Ryan ................ A61M 39/045 251/149.1 |
| 6,343,629 B1 | 2/2002 | Wessman et al. |
| 6,358,236 B1 | 3/2002 | DeFoggi et al. |
| 6,409,708 B1 | 6/2002 | Wessman |
| 6,474,375 B2 | 11/2002 | Spero et al. |
| 6,478,788 B1 | 11/2002 | Aneas |
| 6,544,246 B1 | 4/2003 | Niedospial, Jr. |
| 6,551,299 B2 | 4/2003 | Miyoshi et al. |
| 6,585,695 B1 | 7/2003 | Adair et al. |
| 6,599,273 B1 | 7/2003 | Lopez |
| 6,610,040 B1 | 8/2003 | Fowles et al. |
| 6,629,958 B1 | 10/2003 | Spinello |
| 6,656,433 B2 | 12/2003 | Sasso |
| 6,715,520 B2 | 4/2004 | Andréasson et al. |
| 6,746,438 B1 | 6/2004 | Arnissolle |
| 6,814,726 B1 | 11/2004 | Lauer |
| 6,852,103 B2 | 2/2005 | Fowles et al. |
| 6,875,203 B1 | 4/2005 | Fowles et al. |
| 6,875,205 B2 | 4/2005 | Leinsing |
| 6,911,025 B2 | 6/2005 | Miyahara |
| 6,997,917 B2 | 2/2006 | Niedospial, Jr. et al. |
| 7,040,598 B2 | 5/2006 | Raybuck |
| 7,083,605 B2 | 8/2006 | Miyahara |
| 7,097,209 B2 | 8/2006 | Unger et al. |
| 7,261,707 B2 | 8/2007 | Frezza et al. |
| 7,306,584 B2 | 12/2007 | Wessman et al. |
| 7,326,194 B2 | 2/2008 | Zinger et al. |
| 7,350,535 B2 | 4/2008 | Liepold et al. |
| 7,354,427 B2 | 4/2008 | Fangrow |
| 7,452,349 B2 | 11/2008 | Miyahara |
| 7,547,300 B2 | 6/2009 | Fangrow |
| 7,628,772 B2 | 12/2009 | McConnell et al. |
| 7,648,491 B2 | 1/2010 | Rogers |
| 7,658,734 B2 | 2/2010 | Adair et al. |
| 7,743,799 B2 | 6/2010 | Mosier et al. |
| 7,744,581 B2 | 6/2010 | Wallén et al. |
| 7,758,560 B2 | 7/2010 | Connell et al. |
| 7,803,140 B2 | 9/2010 | Fangrow, Jr. |
| 7,867,215 B2 | 1/2011 | Akerlund et al. |
| 7,879,018 B2 | 2/2011 | Zinger et al. |
| 7,900,659 B2 | 3/2011 | Whitley et al. |
| 7,927,316 B2 | 4/2011 | Proulx et al. |
| 7,942,860 B2 | 5/2011 | Horppu |
| 7,975,733 B2 | 7/2011 | Horppu et al. |
| 7,992,597 B2 | 8/2011 | Py et al. |
| 8,002,130 B2 | 8/2011 | Thilly |
| 8,096,525 B2 | 1/2012 | Ryan |
| 8,122,923 B2 | 2/2012 | Kraus et al. |
| 8,123,738 B2 | 2/2012 | Vaillancourt |
| 8,137,332 B2 | 3/2012 | Pipelka |
| 8,167,863 B2 | 5/2012 | Yow |
| 8,177,768 B2 | 5/2012 | Leinsing |
| 8,196,614 B2 | 6/2012 | Kriheli |
| 8,206,367 B2 | 6/2012 | Warren et al. |
| 8,211,069 B2 | 7/2012 | Fangrow, Jr. |
| 8,211,082 B2 | 7/2012 | Hasegawa et al. |
| 8,225,949 B2 | 7/2012 | Aneas |
| 8,226,628 B2 | 7/2012 | Muramatsu et al. |
| 8,257,286 B2 | 9/2012 | Meyer et al. |
| 8,267,127 B2 | 9/2012 | Kriheli |
| 8,277,424 B2 | 10/2012 | Pan |
| 8,317,741 B2 | 11/2012 | Kraushaar |
| 8,317,743 B2 | 11/2012 | Denenburg |
| 8,398,607 B2 | 3/2013 | Fangrow, Jr. |
| 8,403,905 B2 | 3/2013 | Yow |
| 8,425,487 B2 | 4/2013 | Beiriger et al. |
| 8,449,521 B2 | 5/2013 | Thorne, Jr. et al. |
| 8,454,579 B2 | 6/2013 | Fangrow, Jr. |
| 2002/0177819 A1 | 11/2002 | Barker et al. |
| 2003/0070726 A1 | 4/2003 | Andreasson et al. |
| 2003/0153895 A1 | 8/2003 | Leinsing |
| 2005/0065495 A1 | 3/2005 | Zambaux |
| 2005/0182383 A1 | 8/2005 | Wallen |
| 2005/0215976 A1 | 9/2005 | Wallen |
| 2006/0118749 A1 | 6/2006 | Ryan et al. |
| 2006/0155257 A1 | 7/2006 | Reynolds |
| 2007/0079894 A1 | 4/2007 | Kraus et al. |
| 2008/0009789 A1 | 1/2008 | Zinger et al. |
| 2008/0045919 A1 | 2/2008 | Jakob et al. |
| 2008/0097371 A1 | 4/2008 | Shemesh |
| 2008/0249479 A1 | 10/2008 | Zinger et al. |
| 2008/0262466 A1 | 10/2008 | Smith et al. |
| 2008/0287914 A1 | 11/2008 | Wyatt et al. |
| 2008/0306439 A1 | 12/2008 | Nelson et al. |
| 2009/0159485 A1 | 6/2009 | Jakob et al. |
| 2010/0179506 A1 | 7/2010 | Shemesh et al. |
| 2010/0217226 A1 | 8/2010 | Shemesh |
| 2010/0241088 A1 | 9/2010 | Ranalletta et al. |
| 2011/0004183 A1 * | 1/2011 | Carrez ................ A61J 1/2096 604/405 |
| 2011/0022023 A1 | 1/2011 | Weitzel et al. |
| 2011/0062703 A1 | 3/2011 | Lopez et al. |
| 2011/0074148 A1 | 3/2011 | Imai |
| 2011/0106046 A1 | 5/2011 | Hiranuma et al. |
| 2011/0208128 A1 | 8/2011 | Wu et al. |
| 2011/0257621 A1 | 10/2011 | Fangrow |
| 2011/0291406 A1 | 12/2011 | Kraft et al. |
| 2012/0035580 A1 | 2/2012 | Fangrow |
| 2012/0046636 A1 | 2/2012 | Kriheli |
| 2012/0053554 A1 | 3/2012 | Simpson et al. |
| 2012/0123381 A1 | 5/2012 | Kraus et al. |
| 2012/0192968 A1 | 8/2012 | Bonnal et al. |
| 2012/0192976 A1 | 8/2012 | Rahimy et al. |
| 2012/0203193 A1 | 8/2012 | Rogers |
| 2012/0265163 A1 | 10/2012 | Cheng et al. |
| 2012/0279884 A1 | 11/2012 | Tennican et al. |
| 2012/0316536 A1 | 12/2012 | Carrez et al. |
| 2012/0323172 A1 | 12/2012 | Lev et al. |
| 2013/0006211 A1 | 1/2013 | Takemoto |

(56) References Cited

U.S. PATENT DOCUMENTS

| | | |
|---|---|---|
| 2013/0012908 A1 | 1/2013 | Yeung |
| 2013/0066293 A1 | 3/2013 | Garfield et al. |
| 2013/0072893 A1 | 3/2013 | Takemoto |
| 2013/0076019 A1 | 3/2013 | Takemoto |
| 2013/0079744 A1 | 3/2013 | Okiyama et al. |
| 2013/0184672 A1 | 7/2013 | Nord et al. |
| 2014/0150925 A1 | 6/2014 | Sjögren et al. |
| 2014/0276649 A1 | 9/2014 | Ivosevic et al. |
| 2014/0311624 A1 | 10/2014 | Eilertsen et al. |
| 2014/0360623 A1 | 12/2014 | Nielsen et al. |
| 2015/0082746 A1 | 3/2015 | Ivosevic et al. |
| 2015/0101706 A1 | 4/2015 | Fukuoka |

FOREIGN PATENT DOCUMENTS

| | | |
|---|---|---|
| JP | 60501294 A | 8/1985 |
| JP | 60501342 A | 8/1985 |
| JP | 2002166948 A | 6/2002 |
| JP | 2002526179 A | 8/2002 |
| JP | 2004189265 A | 7/2004 |
| JP | 2007509691 A | 4/2007 |
| WO | 2005011781 A1 | 2/2005 |
| WO | 2006103074 A1 | 10/2006 |
| WO | 2009024807 A1 | 2/2009 |
| WO | 2009090627 A1 | 7/2009 |
| WO | 2011050333 A1 | 4/2011 |
| WO | 2012069401 A1 | 5/2012 |
| WO | 2012119225 A1 | 9/2012 |
| WO | 2012143921 A1 | 10/2012 |
| WO | 2012168235 A1 | 12/2012 |
| WO | 2013025946 A1 | 2/2013 |
| WO | 2013054323 A1 | 4/2013 |
| WO | 2013066779 A1 | 5/2013 |
| WO | 2013115730 A1 | 8/2013 |
| WO | 2013179596 A1 | 12/2013 |

* cited by examiner

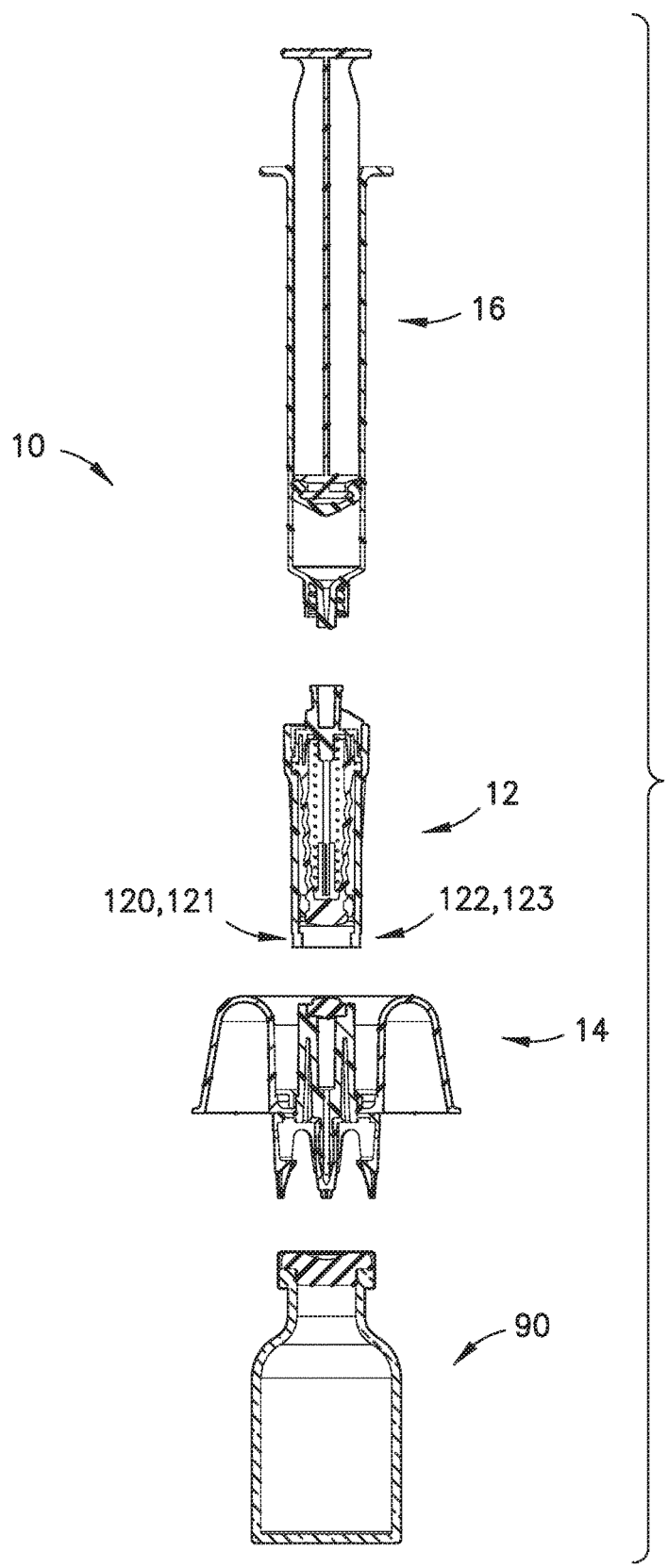

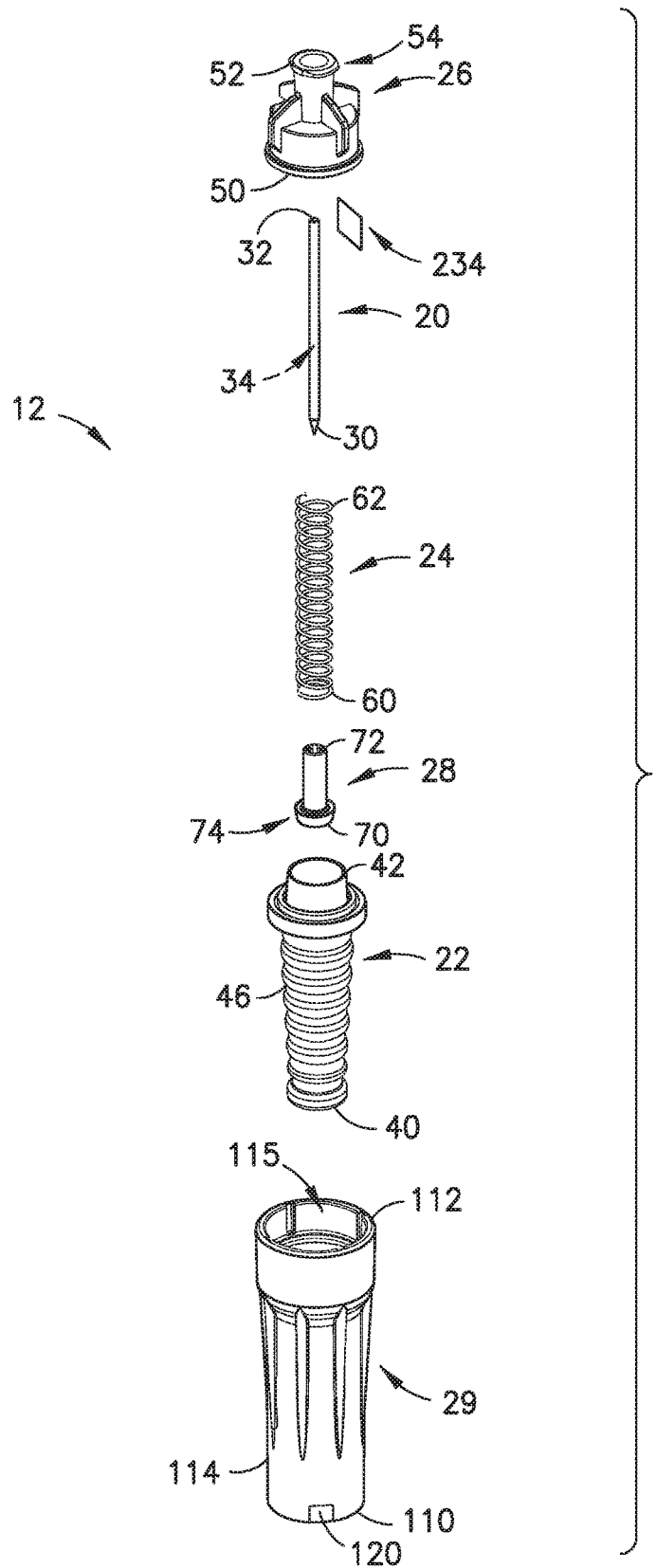

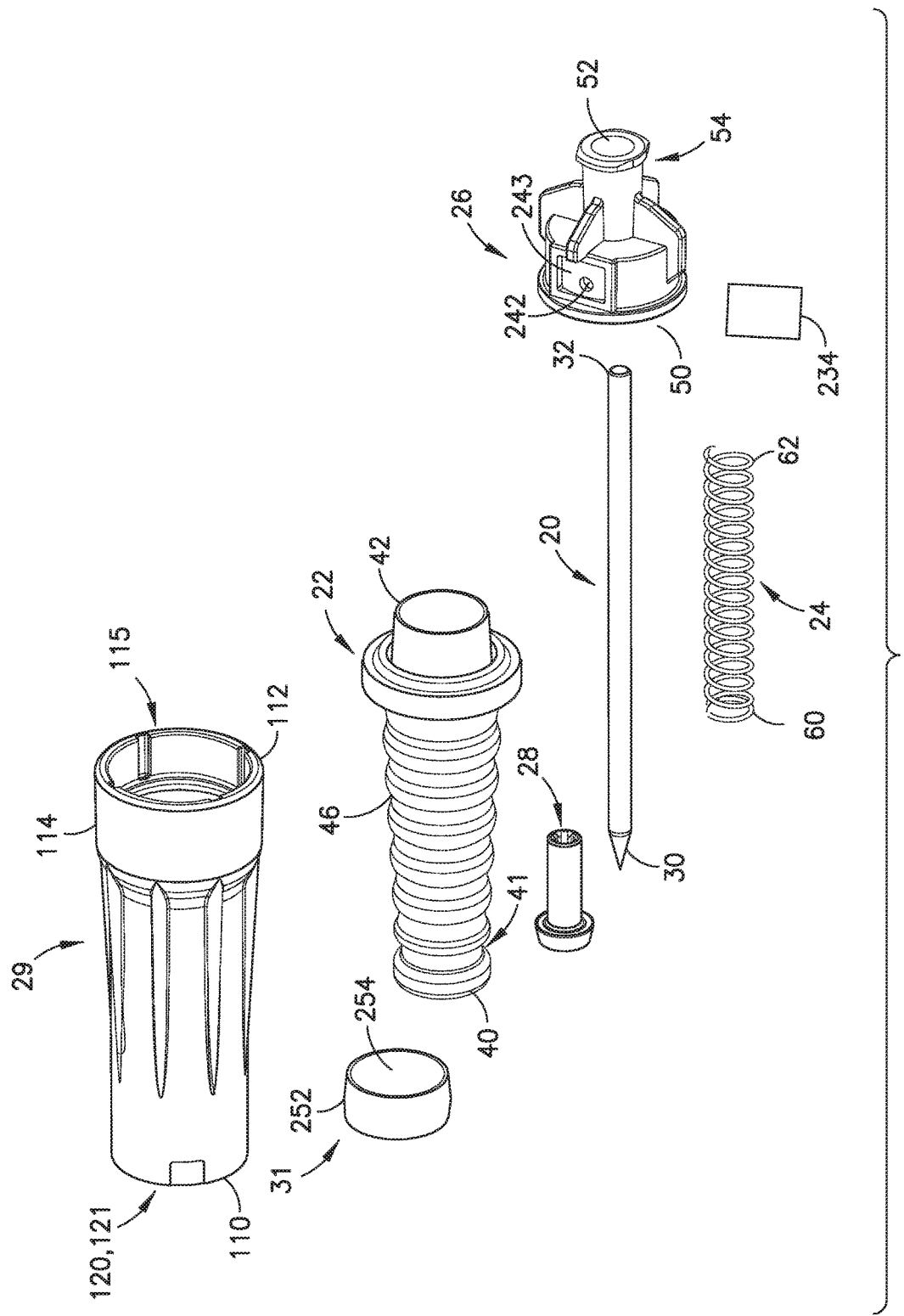

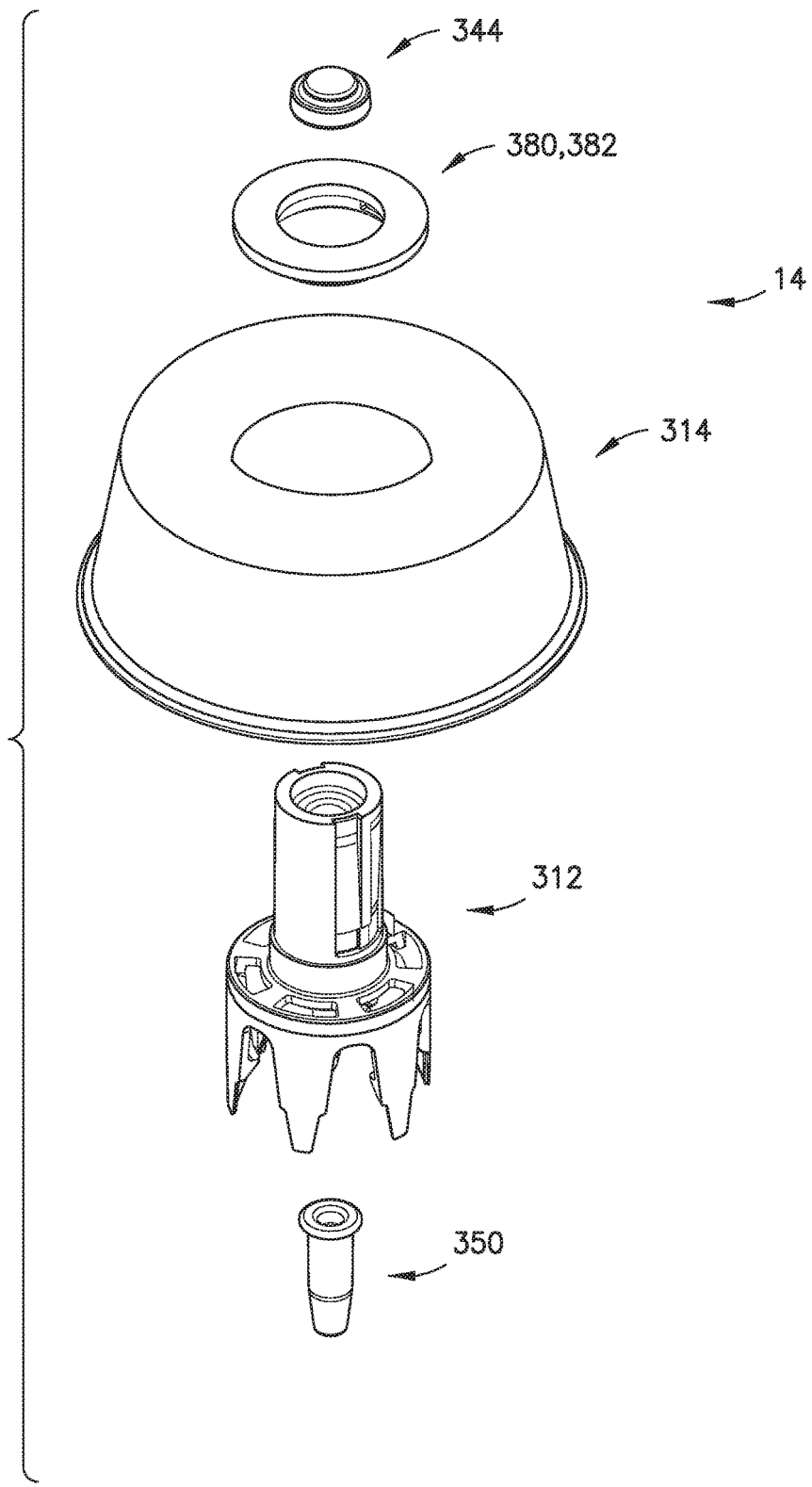

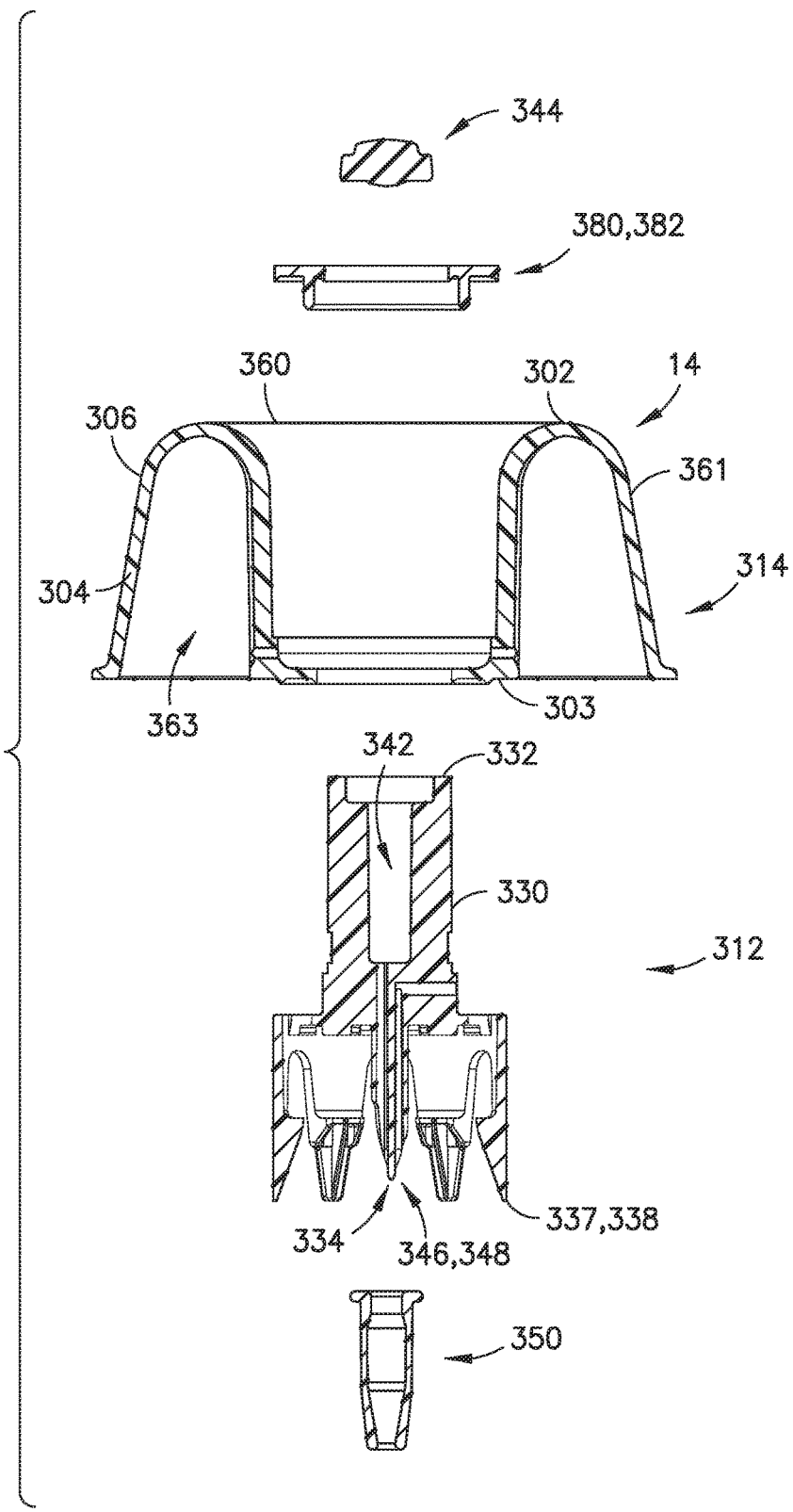

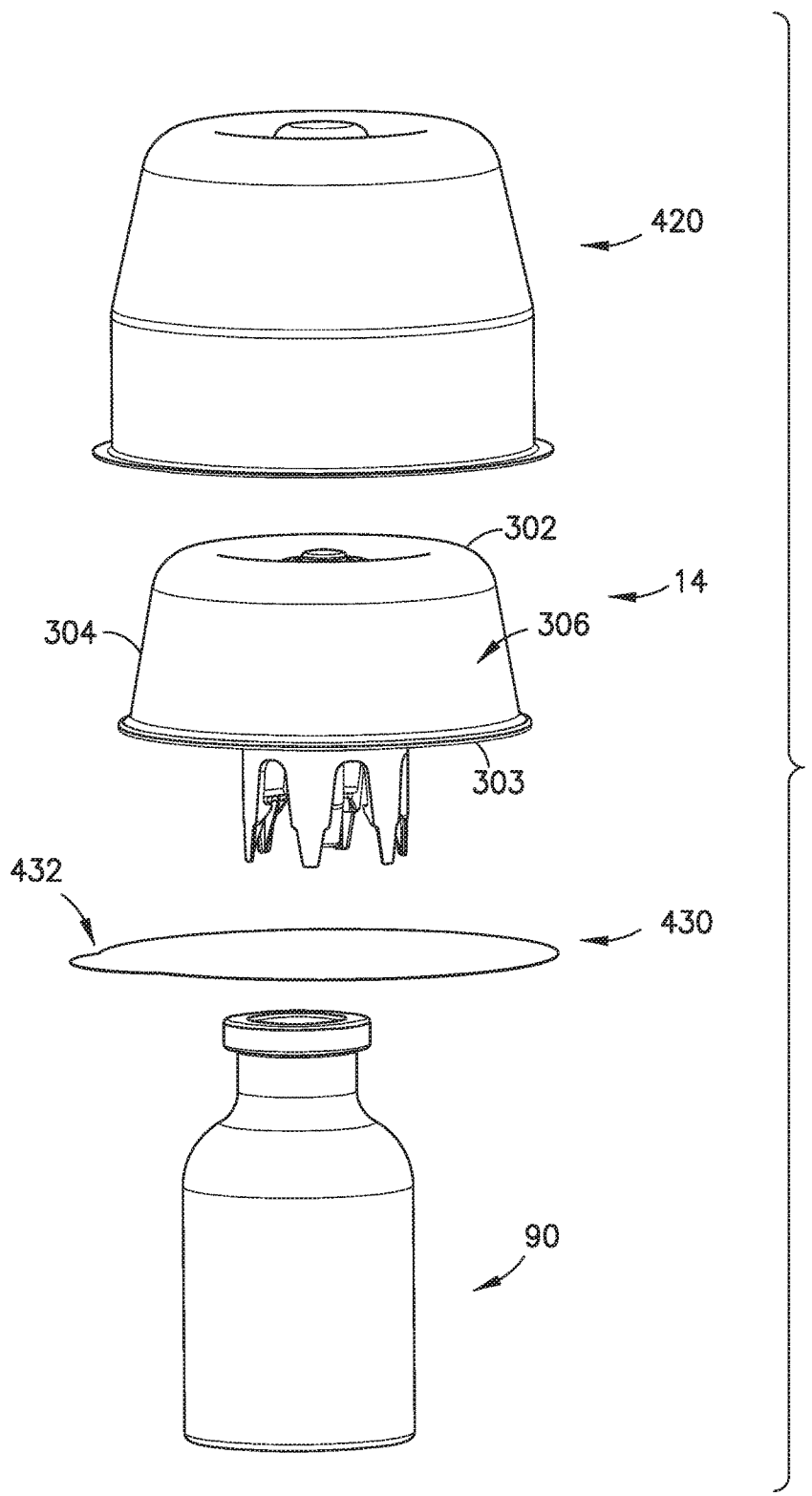

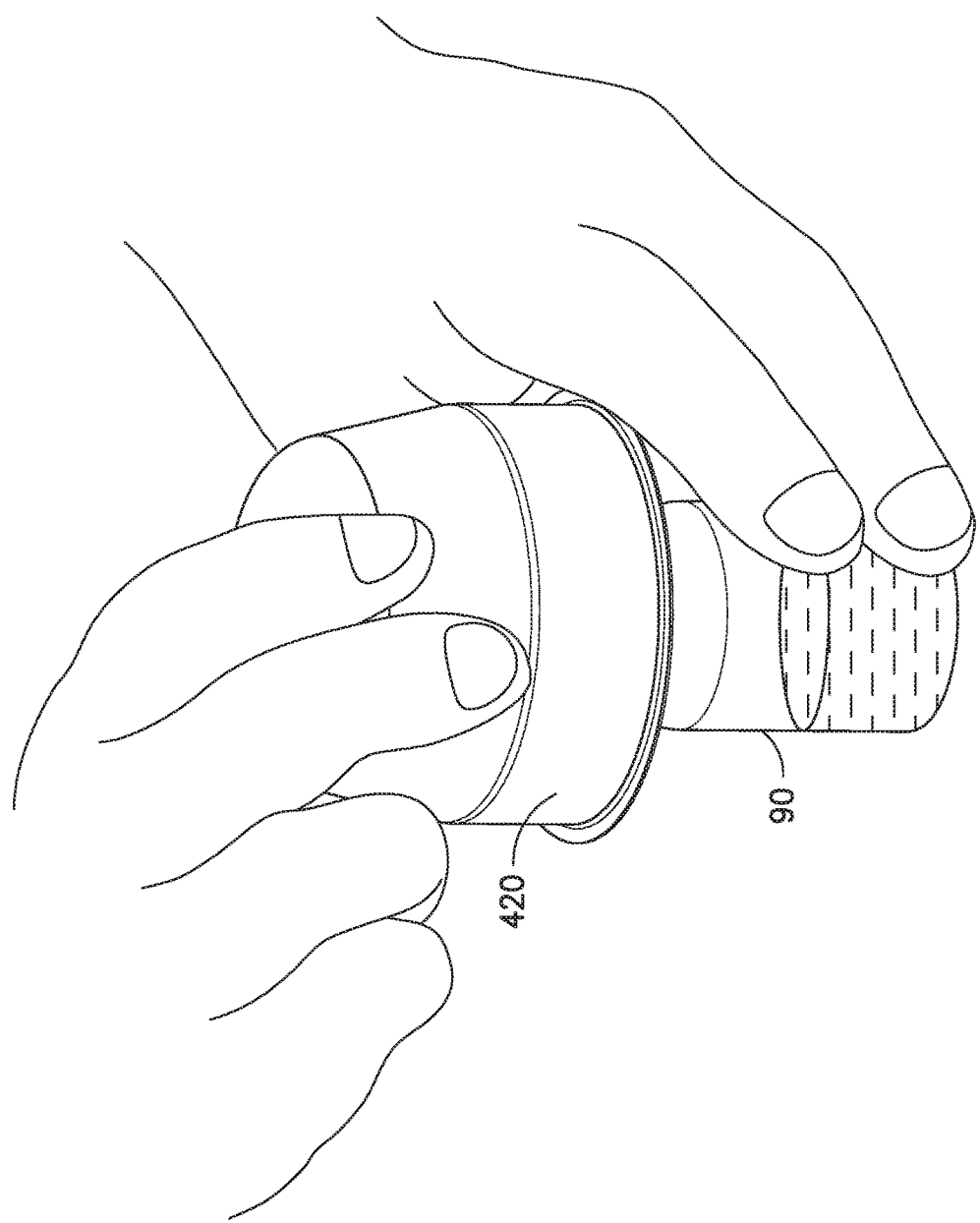

SYSTEM FOR CLOSED TRANSFER OF FLUIDS

CROSS-REFERENCE TO RELATED APPLICATIONS

The present application is a divisional application of U.S. patent application Ser. No. 14/204,428, entitled "System for Closed Transfer of Fluids" filed Mar. 11, 2014, which claims the benefit of U.S. Provisional Patent Application Ser. Nos. 61/787,674, filed Mar. 15, 2013, 61/895,168, filed Oct. 24, 2013, 61/895,182, filed Oct. 24, 2013, and 61/895,187, filed Oct. 24, 2013, the entire disclosures of each of which are incorporated herein by reference.

BACKGROUND OF THE INVENTION

1. Field of the Disclosure

The present disclosure relates generally to a system for the closed transfer of fluids. More particularly, the present disclosure relates to a system that provides leak-proof sealing and pressure equalization during engagement of a cannula with a vial, during transfer of a substance from a vial chamber to a barrel chamber via the cannula, and during disengagement of the cannula from the vial.

2. Description of the Related Art

Health care providers reconstituting, transporting, and administering hazardous drugs, such as cancer treatments, can put health care providers at risk of exposure to these medications and present a major hazard in the health care environment. For example, nurses treating cancer patients risk being exposed to chemotherapy drugs and their toxic effects. Unintentional chemotherapy exposure can affect the nervous system, impair the reproductive system, and bring an increased risk of developing blood cancers in the future. In order to reduce the risk of health care providers being exposed to toxic drugs, the closed transfer of these drugs becomes important.

Some drugs must be dissolved or diluted before they are administered, which involves transferring a solvent from one container to a sealed vial containing the drug in powder or liquid form, by means of a needle. Drugs may be inadvertently released into the atmosphere in gas form or by way of aerosolization, during the withdrawal of the needle from the vial and while the needle is inside the vial if any pressure differential between the interior of the vial and the surrounding atmosphere exists.

SUMMARY OF THE INVENTION

The present disclosure provides a system for the closed transfer of fluids that provides substantially leak-proof sealing and pressure equalization during engagement of a cannula with a vial, during transfer of a substance from a vial chamber to a barrel chamber via the cannula, and during disengagement of the cannula from the vial. The leak-proof sealing of the system substantially prevents leakage of both air and liquid during use of the system. The system of the present disclosure also permits pressure equalization between a vial and the system when the system is attached to the vial. The system is compatible with a needle and syringe assembly for accessing a medication contained within a vial for administering the medication to a patient. The system is also compatible to be used with a drug reconstitution system.

In accordance with an embodiment of the present invention, a system includes a cannula attachable to a first container having a first chamber such that the cannula is in fluid communication with the first chamber; a syringe adapter having a housing and a cannula seal having a resilient sleeve with the cannula seal enclosing at least a portion of the cannula, the cannula seal disposed within the housing, the housing including a first connection element; and a second container adapter attachable to a second container having a second chamber, the second container adapter having a second container seal, and a second connection element; wherein with the first connection element of the syringe adapter engaged with the second connection element of the second container adapter, the syringe adapter is secured to the second container adapter.

In one configuration, the second container adapter includes a pressure equalization system with the pressure equalization system including a toroidal expandable balloon. In another configuration, the second container adapter includes a second container adapter housing and a portion of the toroidal expandable balloon is not covered by the second container adapter housing. In yet another configuration, a portion of the toroidal expandable balloon can expand in an axial direction. In one configuration, the cannula seal and the second container seal provide substantially leak-proof sealing during engagement of the cannula with the second container, during transfer of a first substance from the second chamber of the second container to the first chamber of the first container via the cannula, and during disengagement of the cannula from the second container. In another configuration, the syringe adapter includes an intake air filter. In yet another configuration, the first connection element includes a first projecting element and the second connection element includes a first connection channel, a first disconnection channel, and a first securement element disposed between the first connection channel and the first disconnection channel, the first connection channel separate and distinct from the first disconnection channel, wherein with the first projecting element engaged with the first securement element, the syringe adapter is secured to the second container adapter. In one configuration, the first container is a syringe barrel. In another configuration, the second container is a vial.

In accordance with another embodiment of the present invention, a system includes a first container defining a first chamber; a cannula attachable to the first container such that the cannula is in fluid communication with the first chamber; a syringe adapter having a housing and a cannula seal having a resilient sleeve, the cannula seal enclosing at least a portion of the cannula, the cannula seal disposed within the housing, the housing including a first connection element; a second container defining a second chamber; a second container septum engaged with the second container to seal the second chamber; and a second container adapter attachable to the second container, the second container adapter having a second container seal and a second connection element, wherein with the first connection element of the syringe adapter engaged with the second connection element of the second container adapter, the syringe adapter is secured to the second container adapter.

In one configuration, the cannula seal, the second container seal, and the second container septum provide substantially leak-proof sealing during engagement of the cannula with the second container, during transfer of a first substance from the second chamber of the second container to the first chamber of the first container via the cannula, and during disengagement of the cannula from the second container. In another configuration, the second container adapter includes a pressure equalization system including a toroidal expandable balloon. In yet another configuration, the second container adapter includes a second container adapter housing and a portion of the toroidal expandable balloon is not covered by the second container adapter housing. In one configuration, a portion of the toroidal expandable balloon can expand in an axial direction. In another configuration, the syringe adapter includes an intake air filter. In yet another configuration, the first connection element includes a first projecting element and the second connection element includes a first connection channel, a first disconnection channel, and a first securement element disposed between the first connection channel and the first disconnection channel, the first connection channel distinct from the first disconnection channel, wherein with the first projecting element engaged with the first securement element, the syringe adapter is secured to the second container adapter. In one configuration, the first container is a syringe barrel. In another configuration, the second container is a vial.

In accordance with another embodiment of the present invention, a vial adapter includes a vial access system including a vial access housing having a first end and a second end, the vial access housing including a seal membrane; a first connection element disposed at the first end of the vial access housing, the first connection element engageable with a second connection element of a syringe adapter to secure the vial adapter to the syringe adapter; a plurality of vial grip members disposed at the second end of the vial access housing, the plurality of vial grip members attachable to a vial to secure the vial adapter to the vial; and a spike disposed at the second end of the vial access housing, the spike attachable to the vial such that the spike is in fluid communication with a chamber of the vial. The vial adapter further includes a pressure equalization system attachable to the vial access system, the pressure equalization system including a pressure equalization housing and a toroidal expandable balloon, wherein a portion of the toroidal expandable balloon is not covered by the pressure equalization housing, wherein with the vial adapter attached to the vial, the pressure equalization system is in fluid communication with the vial.

In one configuration, the vial adapter includes a vial sleeve seal disposed over the spike, the vial sleeve seal providing a seal between the vial adapter and the vial with the spike attached to the vial. In another configuration, a portion of the toroidal expandable balloon can expand in an axial direction. In yet another configuration, the pressure equalization housing includes a filter.

In accordance with another embodiment of the present invention, a syringe adapter includes a cannula attachable to a first container having a first chamber such that the cannula is in fluid communication with the first chamber of the first container; a syringe adapter housing including a first connection element, the first connection element engageable with a second connection element of a vial adapter to secure the syringe adapter to the vial adapter; a cannula seal including a resilient sleeve, the cannula seal enclosing at least a portion of the cannula, the cannula seal disposed within the syringe adapter housing; a spring disposed over the cannula such that the spring is positioned between the cannula and the cannula seal, wherein the spring provides a biasing force; and an intake air filter disposed within the syringe adapter housing.

In one configuration, the syringe adapter housing includes a first end, a second end, and a sidewall extending therebetween, the sidewall having an exterior surface and an interior surface, the interior surface of the sidewall having the first connection element. In another configuration, the syringe adapter further includes a gliding ring positioned between the cannula seal and the housing. In yet another configuration, the gliding ring is secured to a distal end of the cannula seal.

In a further embodiment, the present disclosure provides a packaging member for a vial adapter having an exterior profile. The packaging member is sized and adapted to receive the vial adapter therein and includes a sidewall that defines an interior profile, the interior profile of the packaging member being sized and shaped to substantially correspond to the exterior profile of the vial adapter. The packaging member of the present disclosure provides for a vial adapter to be secured and contained within the packaging member using a taper lock and an interference connection to provide a secure fit therebetween, such that, with the vial adapter received within the packaging member and with a sealing member removed from the packaging member, the packaging member can be used as an interface between the hand of a user and the vial adapter so that the vial adapter can be placed onto a vial without taking the vial adapter out of the packaging member.

In accordance with an embodiment of the present invention, a packaging member for a vial adapter having an exterior profile includes a packaging member body having a proximal end, a distal end, and a sidewall extending therebetween and defining an interior, the sidewall of the packaging member body defining an interior profile, the interior of the packaging member body sized and adapted to receive the vial adapter therein, and the interior profile of the packaging member body sized and shaped to substantially correspond to the exterior profile of the vial adapter.

In one configuration, the packaging member further includes a sealing member removably attachable to the proximal end of the packaging member body. In another configuration, the sidewall of the packaging member body includes a cylindrical portion, a tapered portion, and a bottom arcuate portion. In yet another configuration, the interior profile of the packaging member body is sized and shaped to substantially correspond to the exterior profile of the vial adapter such that, with the vial adapter received within the interior of the packaging member body, the vial adapter is secured within the packaging member body by an interference fit.

In accordance with another embodiment of the present invention, a system includes a vial adapter having a first end, a second end, and a wall extending therebetween, the wall defining an exterior profile, the vial adapter having a vial seal, the vial adapter attachable to a vial; and a packaging member having a proximal end, a distal end, and a sidewall extending therebetween and defining an interior, the sidewall of the packaging member defining an interior profile, the interior of the packaging member sized and adapted to receive the vial adapter therein, and the interior profile of the packaging member sized and shaped to substantially correspond to the exterior profile of the vial adapter.

In one configuration, the system further includes a sealing member removably attachable to the proximal end of the packaging member, wherein with the vial adapter received within the interior of the packaging member and the sealing member attached to the packaging member, the sealing member seals the vial adapter within the packaging member. In another configuration, the sidewall of the packaging member includes a cylindrical portion, a tapered portion, and a bottom arcuate portion. In yet another configuration, the vial adapter includes a tapered exterior wall portion. In one configuration, with the vial adapter received within the interior of the packaging member, the tapered portion of the packaging member and the tapered exterior wall portion of the vial adapter form complementary locking tapers. In another configuration, the interior profile of the packaging member is sized and shaped to substantially correspond to the exterior profile of the vial adapter such that, with the vial adapter received within the interior of the packaging member, the vial adapter is secured within the packaging member by an interference fit. In yet another configuration, the vial adapter further includes a plurality of stabilizing ribs spaced around a periphery of the wall of the vial adapter.

In accordance with another embodiment of the present invention, a system includes a vial adapter having a first end, a second end, and a wall extending therebetween, the vial adapter having a vial seal and a vial engagement member, the vial engagement member attachable to a vial; a packaging member having a proximal end, a distal end, and a sidewall extending therebetween and defining an interior, the interior of the packaging member sized and adapted to receive the vial adapter therein; and a sealing member removably attachable to the proximal end of the packaging member, wherein with the vial adapter received within the interior of the packaging member and the sealing member attached to the packaging member, the sealing member seals the vial adapter within the packaging member, and wherein with the sealing member removed from the packaging member and with the vial adapter received within the interior of the packaging member, the vial engagement member of the vial adapter is engageable with the vial while the vial adapter is received within the interior of the packaging member.

In one configuration, the wall of the vial adapter defines an exterior profile and the sidewall of the packaging member defines an interior profile, the interior profile of the packaging member sized and shaped to substantially correspond to the exterior profile of the vial adapter. In another configuration, the sidewall of the packaging member includes a cylindrical portion, a tapered portion, and a bottom arcuate portion. In yet another configuration, the interior profile of the packaging member is sized and shaped to substantially correspond to the exterior profile of the vial adapter such that, with the vial adapter received within the interior of the packaging member, the vial adapter is secured within the packaging member by an interference fit.

In accordance with another embodiment of the present invention, a system includes a vial defining a vial chamber; a first substance contained within the vial chamber; a vial adapter having a first end, a second end, and a wall extending therebetween, the wall defining an exterior profile, the vial adapter having a vial seal and a vial engagement member, the vial engagement member attachable to the vial; and a packaging member having a proximal end, a distal end, and a sidewall extending therebetween and defining an interior, the sidewall of the packaging member defining an interior profile, the interior of the packaging member sized and adapted to receive the vial adapter therein, and the interior profile of the packaging member sized and shaped to substantially correspond to the exterior profile of the vial adapter In one configuration, the system further includes a sealing member removably attachable to the proximal end of the packaging member, wherein with the vial adapter received within the interior of the packaging member and the sealing member attached to the packaging member, the sealing member seals the vial adapter within the packaging member. In another configuration, with the sealing member removed from the packaging member and with the vial adapter received within the interior of the packaging member, the vial engagement member of the vial adapter is directly engageable with the vial while the vial adapter is received within the interior of the packaging member. In yet another configuration, the sidewall of the packaging member includes a cylindrical portion, a tapered portion, and a bottom arcuate portion. In one configuration, the interior profile of the packaging member is sized and shaped to substantially correspond to the exterior profile of the vial adapter such that, with the vial adapter received within the interior of the packaging member, the vial adapter is secured within the packaging member by an interference fit.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 1B is a cross-sectional view of the system of FIG. 1A in accordance with an embodiment of the present invention.

FIG. 2A is an exploded, perspective view of a syringe adapter in accordance with an embodiment of the present invention.

FIG. 2C is another exploded, perspective view of a syringe adapter in accordance with an embodiment of the present invention.

FIG. 4A is an exploded, perspective view of a vial adapter in accordance with an embodiment of the present invention.

FIG. 4B is an exploded, cross-sectional view of the vial adapter of FIG. 4A in accordance with an embodiment of the present invention.

FIG. 19 is an exploded, perspective view of a system in accordance with an embodiment of the present invention.

FIG. 23B is a perspective view of a second step of using a system of the present disclosure in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1A:
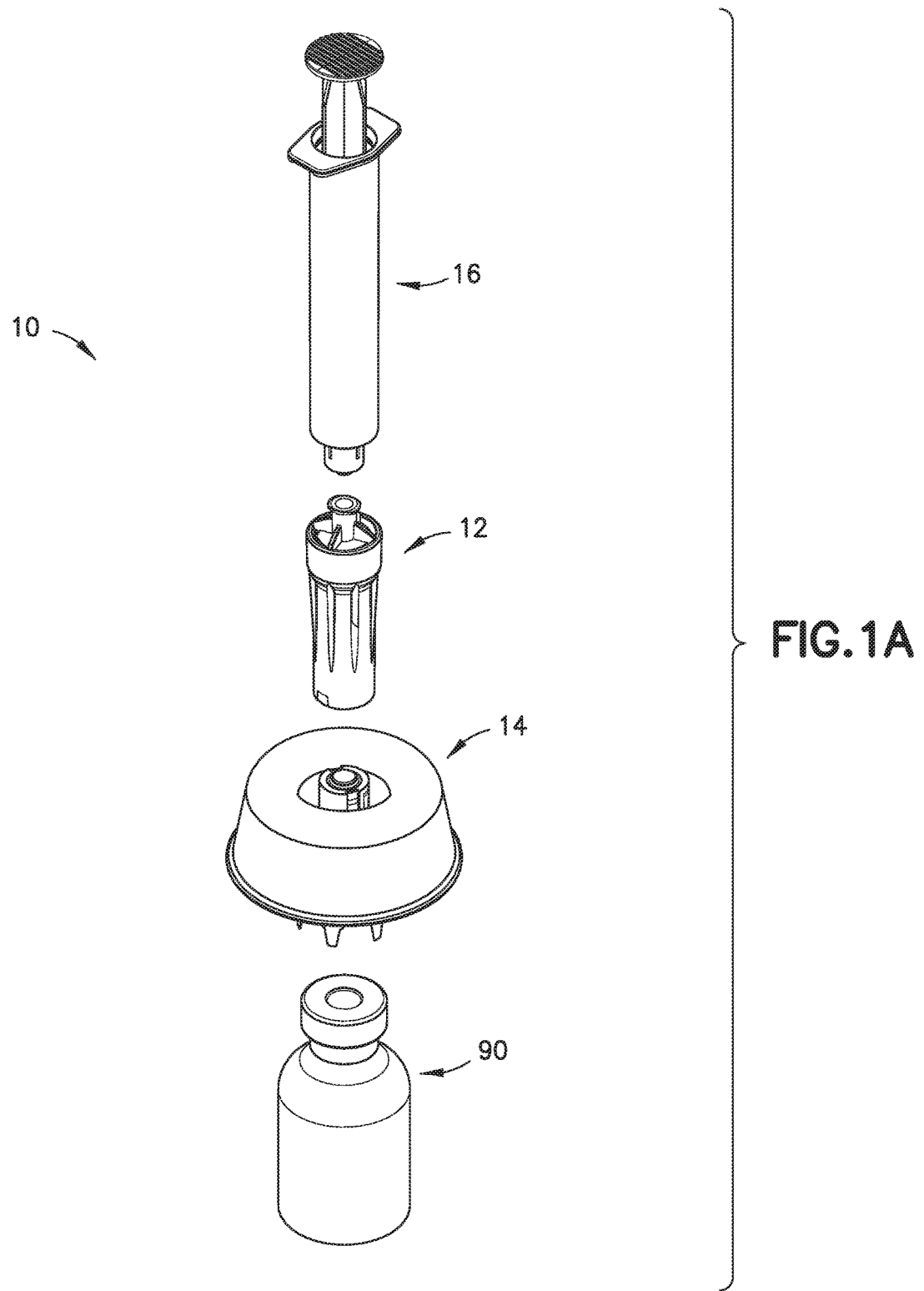
FIG. 1A is an exploded, perspective view of a system in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

In the following discussion, "distal" refers to a direction generally toward an end of a barrel adapted for contact with a patient and/or engagement with a separate device such as a needle assembly or IV connection assembly, and "proximal" refers to the opposite direction of distal, i.e., away from the end of a barrel adapted for engagement with the separate device. For purposes of this disclosure, the above-mentioned references are used in the description of the components of a barrel in accordance with the present disclosure.

FIGS. 1A-18C illustrate an exemplary embodiment of the present disclosure. Referring to FIGS. 1A and 1B, a system for the closed transfer of fluids 10 includes a syringe adapter 12, a vial adapter 14, a barrel assembly 16, and an intravenous (IV) line adapter 18 as will be described in more detail below. System 10 provides substantially leak-proof sealing and pressure balancing during engagement of a cannula with a vial, during transfer of a substance from a vial chamber to a barrel chamber via the cannula, and during disengagement of the cannula from the vial. The leak-proof sealing of the system 10 substantially prevents leakage of both air and liquid during use of the system 10. System 10 is compatible with a needle and syringe assembly for accessing a medication contained within a vial for administering the medication to a patient. System 10 is also compatible to be used with a drug reconstitution system as will be described in more detail below.

Figure 2B:
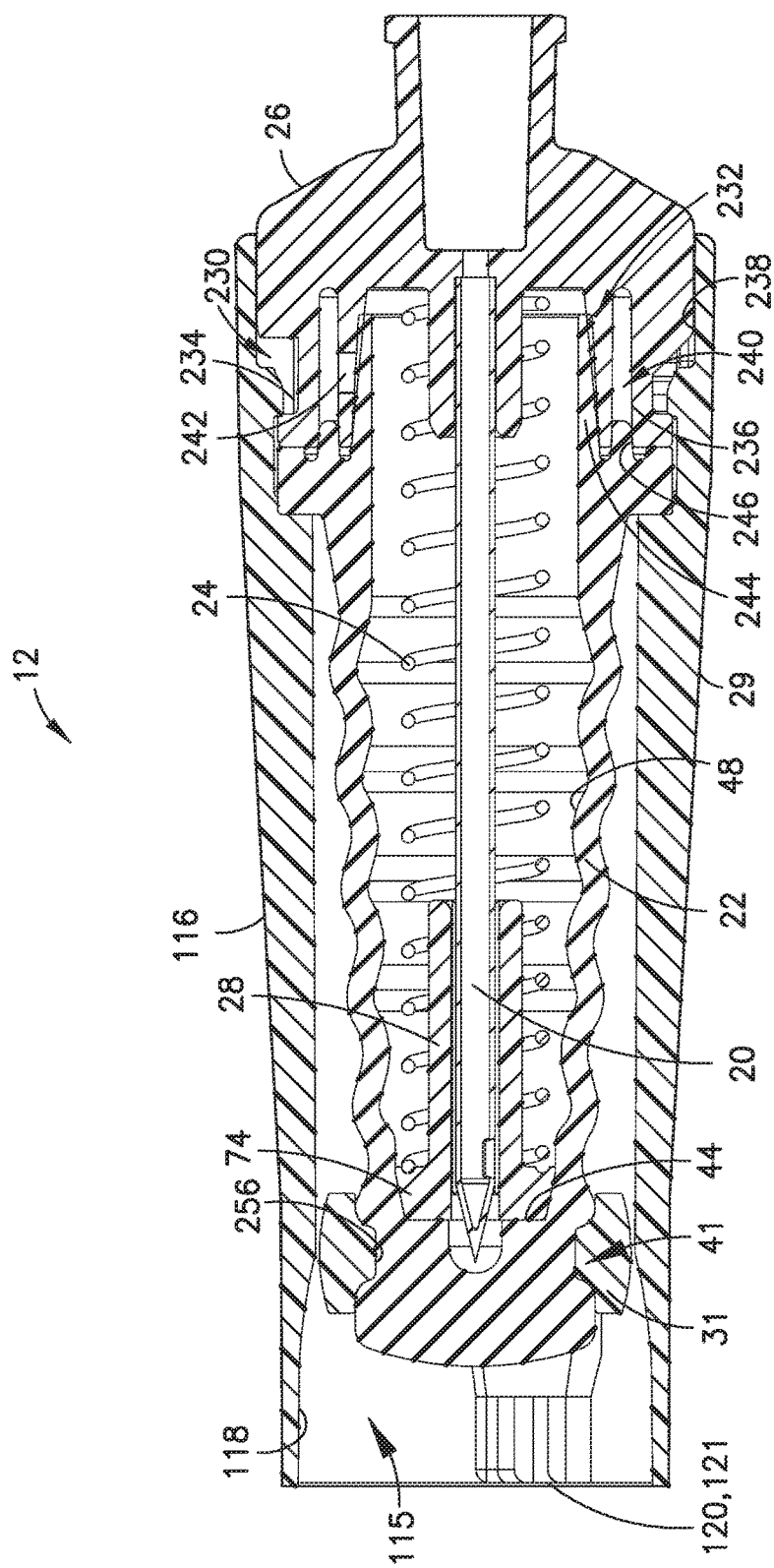
FIG. 2B is an assembled, cross-sectional view of the syringe adapter of FIG. 2A in accordance with an embodiment of the present invention.
Figure 15:
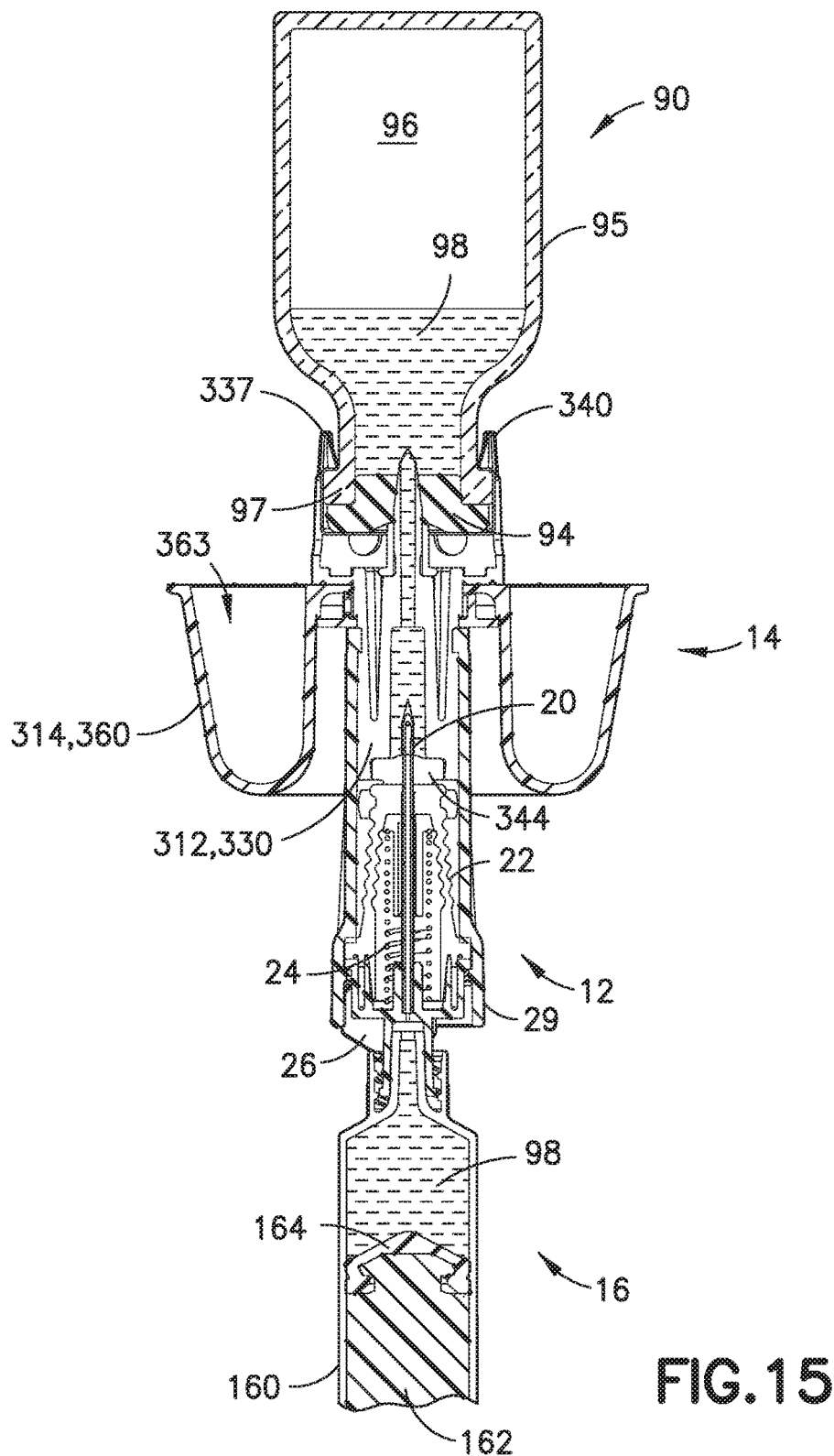
FIG. 15 is a cross-sectional view of the system of FIG. 10 with the system inverted and the cannula seal in communication with the vial seal and a cannula in fluid communication with a substance contained within a vial chamber in accordance with an embodiment of the present invention.

Referring to FIGS. 2A-2C, syringe adapter 12 generally includes a cannula 20, a cannula seal 22, a spring 24, a needle hub 26, a cannula stabilizing member 28, a housing 29, a gliding ring 31, a one-way valve 232, and a filter 234. Referring to FIG. 2A, cannula 20 includes a distal end 30, a proximal end 32, and a lumen 34 extending therebetween. Distal end 30 is in fluid communication with proximal end 32 via lumen 34 of cannula 20. As shown in FIG. 15, distal end 30 of cannula 20 is capable of piercing cannula seal 22 and a vial seal membrane 344 to place a vial chamber 96 in fluid communication with a barrel chamber 176 via cannula 20 as will be described in more detail below. In one embodiment, distal end 30 of cannula 20 defines a sharp point.

Figure 11:
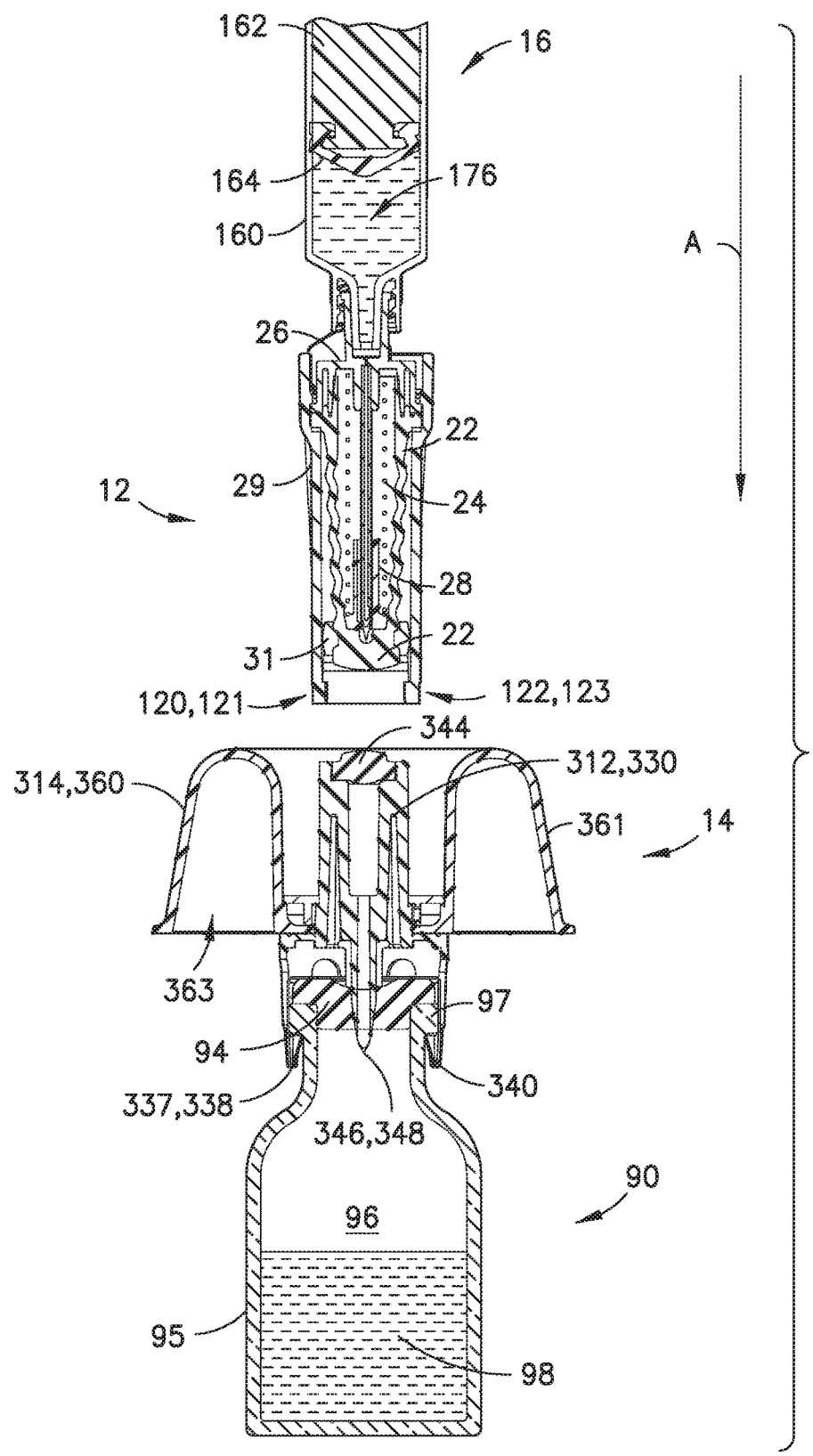
FIG. 11 is a cross-sectional view of the system of FIG. 10 with a cannula seal not in communication with a vial seal in accordance with an embodiment of the present invention.
Figure 12A:
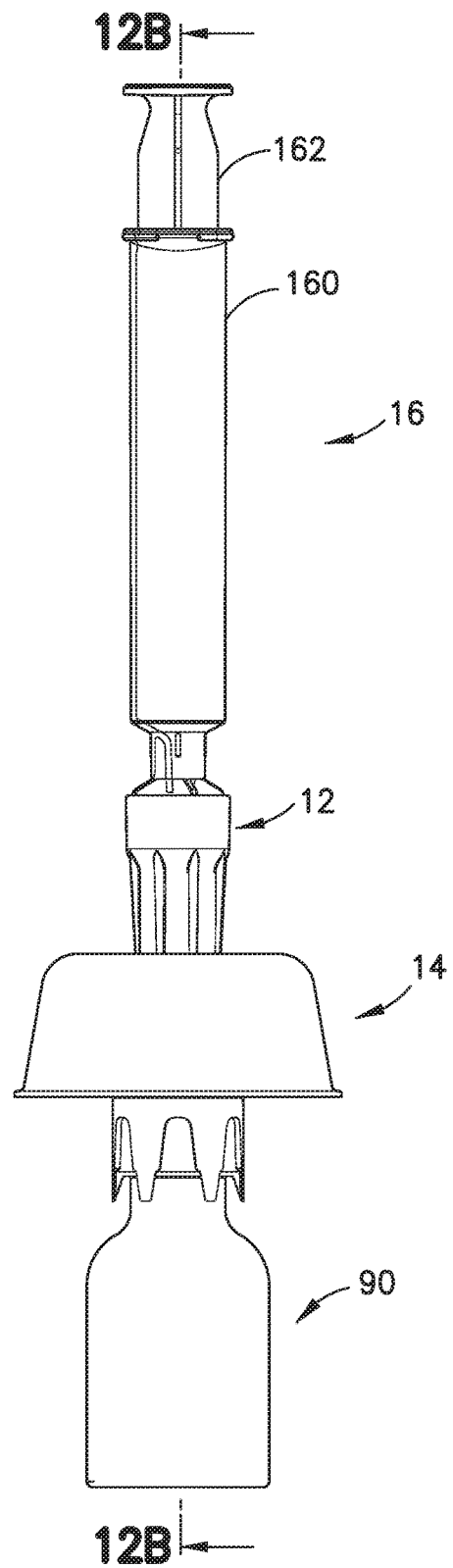
FIG. 12A is an assembled, perspective view of a system in accordance with an embodiment of the present invention.
Figure 12B:
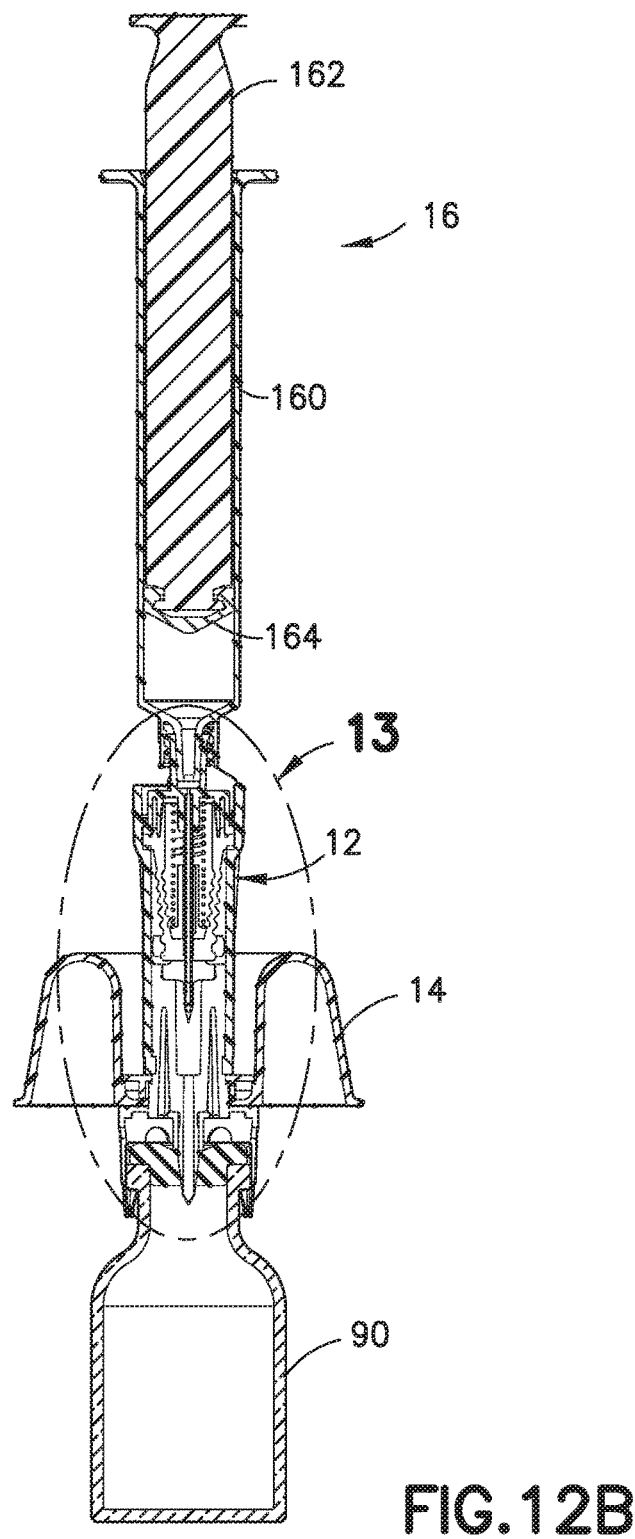
FIG. 12B is a cross-sectional view of the system taken along line 12B-12B of FIG. 12A in accordance with an embodiment of the present invention.
Figure 16:
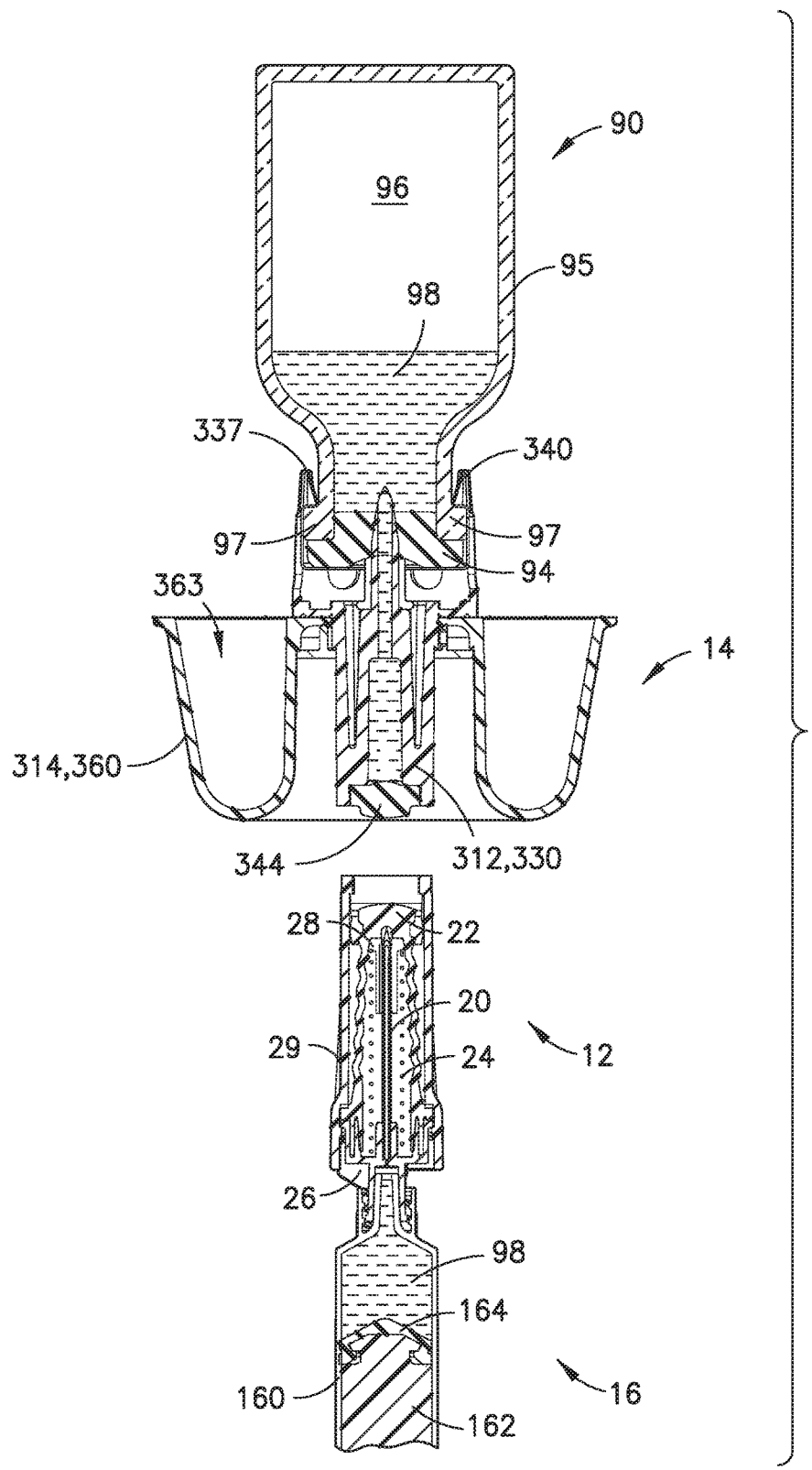
FIG. 16 is a cross-sectional view of the system of FIG. 10 with the system inverted and the cannula seal not in communication with the vial seal and a portion of a substance contained within a vial chamber transferred to a barrel chamber via a cannula in accordance with an embodiment of the present invention.

Referring to FIGS. 2A-2C, cannula seal 22 generally includes a self-sealing seal secured over cannula 20 so that cannula seal 22 encloses cannula 20 in a sealed position (FIGS. 11 and 16) to provide a substantially leak-proof seal preventing any liquid, air, or medication residue from being exposed to a health care provider transferring, reconstituting, transporting, or administering a drug using syringe adapter 12. Referring to FIGS. 11 and 16, with cannula seal 22 in the sealed position, cannula seal 22 encloses cannula 20 to also prevent accidental needle stick injuries to a user of syringe adapter 12. Cannula seal 22 includes a distal end 40, a proximal end 42, annular ribbed members 46 extending therebetween, and a shoulder portion 44 (FIG. 2B) located on an interior wall 48 near distal end 40 of cannula seal 22. In one embodiment, distal end 40 of cannula seal 22 includes an annular cavity 41. The distal end 40 of cannula seal 22 defines a convex surface and has a transverse cross-sectional shape that is generally circular, although it is contemplated that other shapes and sizes of distal end 40 may be used. For example, distal end 40 of cannula seal 22 can have other multi-sided polygon cross-sectional shapes, such as square or oval cross-sectional shapes. The cannula seal 22 may have a length that is about equal to a length of the cannula 20 and, upon assembly of the syringe adapter 12, the cannula seal 22 may extend about the entire length of the cannula 20.

In one embodiment, cannula seal 22 comprises a resilient material. For example, cannula seal 22 is preferably a unitary device molded of any flexible, elastomeric material conventionally used for fabricating gas-proof closures. Cannula seal 22 may be formed of a natural rubber material, polyurethane elastomers, butyl rubbers, or similar materials. It is contemplated that cannula seal 22 is formed of a material having a Shore A hardness of approximately 10 to 50. It is also envisioned that cannula seal 22 can have other material hardness values that would provide an appropriate self-sealing material to provide a substantially leak-proof seal with cannula seal 22 in the sealed position, thereby preventing any liquid or medication residue from being exposed to a health care provider transferring, reconstituting, transporting, or administering a drug using syringe adapter 12. In one embodiment, cannula seal 22 comprises a resilient sleeve.

Referring to FIG. 2A, spring 24 includes a distal end 60 and a proximal end 62. Spring 24 provides a biasing force that promotes cannula seal 22 to enclose cannula 20 in the sealed position as will be described in more detail below. Referring to FIG. 2B, spring 24 is disposed over cannula 20 such that spring 24 is radially positioned between cannula 20 and cannula seal 22, i.e., cannula seal 22 encloses spring 24 and cannula 20.

Referring to FIG. 2B, spring 24 is disposed over cannula 20 and within cannula seal 22 such that distal end 60 of spring 24 engages shoulder portion 44 of cannula seal 22. In this manner, spring 24 exerts the biasing force on shoulder portion 44 of cannula seal 22. Shoulder portion 44 of cannula seal 22 also ensures that spring 24 is secured between shoulder portion 44 and needle hub 26.

Referring to FIGS. 2A-2C, needle hub 26 generally includes a distal end 50 and a proximal end 52. Proximal end 52 of needle hub 26 includes a barrel connection portion 54. In one embodiment, barrel connection portion 54 is a female luer connector that is configured to mate with a male luer connector, although other suitable connectors may be utilized. The barrel connection portion 54 includes a projection that is configured to be received by a corresponding threaded portion of the male luer connector. Other arrangements for the barrel connection portion 54 may be utilized that deter undesired disconnection from the needle hub 26. Referring to FIGS. 11-16, needle hub 26 supports and is secured to a portion of cannula 20. In one embodiment, the needle hub 26 is secured to the cannula 20 via an adhesive, such as an epoxy, although other suitable arrangements for securing the cannula 20 to the needle hub 26 may be utilized. Distal end 50 of needle hub 26 also provides a connection with proximal end 62 of spring 24 so that distal end 60 of spring 24 may be compressed relative to proximal end 62 of spring 24 when cannula 20 pierces cannula seal 22 as will be described in more detail below. With spring 24 compressed, spring 24 exerts a biasing force that promotes cannula seal 22 to elastically enclose cannula 20. Referring to FIGS. 11 and 16, in one embodiment, with cannula seal 22 in the sealed position, spring 24 is loaded between shoulder portion 44 of cannula seal 22 and needle hub 26 in a slightly compressed position so that spring 24 exerts a biasing force that retains cannula seal 22 in the sealed position.

In one embodiment, referring to FIGS. 2A-2C, annular ribbed members 46 of cannula seal 22 provide an additional biasing force that retains cannula seal 22 in the sealed position. Referring to FIGS. 11-14, as cannula 20 is brought into contact with vial adapter 14, annular ribbed members 46 of cannula seal 22 and spring 24 are compressed as cannula 20 pierces cannula seal 22 and vial adapter 14. With annular ribbed members 46 of cannula seal 22 compressed, annular ribbed members 46 exert an additional biasing force that promotes cannula seal 22 to elastically enclose cannula 20.

Referring to FIGS. 2A-2C, housing 29 generally includes a distal or first end 110, a proximal or second end 112, and a sidewall 114 extending therebetween. Sidewall 114 of housing 29 defines a housing chamber 115. Housing chamber 115 is sized and shaped to contain and house the components of syringe adapter 12. The sidewall 114 of housing 29 includes an exterior wall surface 116 and an interior wall surface 118. In one embodiment, the interior wall surface 118 of the sidewall 114 includes a first connection element 120. Referring to FIG. 2B, first connection element 120 extends inwardly from interior wall surface 118 of sidewall 114 into housing chamber 115 adjacent distal end 110. First connection element 120 is engageable with a connection element of a vial adapter or an IV line adapter 18 to secure syringe adapter 12 to a vial adapter or an IV line adapter 18 such that significant relative movement between syringe adapter 12 and the vial adapter or IV line adapter 18 is prevented. In one embodiment, first connection element 120 comprises a first projecting member 121.

In one embodiment, the interior wall surface 118 of the sidewall 114 includes a second connection element 122. Referring to FIG. 2C, second connection element 122 extends inwardly from interior wall surface 118 of sidewall 114 into housing chamber 115 adjacent distal end 110. Second connection element 122 is spaced a distance from first connection element 120. In one embodiment, second connection element 122 is spaced approximately 180 degrees (180°) from first connection element 120. Second connection element 122 is engageable with a connection element of a vial adapter or an IV line adapter 18 to secure syringe adapter 12 to a vial adapter or an IV line adapter 18. In one embodiment, second connection element 122 comprises a second projecting member 123.

Housing 29 provides a protective housing which seals the components of syringe adapter 12 within housing 29, i.e., housing 29 provides a leak prevention and protection enclosure, protects the components of syringe adapter 12 contained within housing 29, and/or maintains a sealed, sterilized environment within housing 29. Housing 29 also provides connection elements 120, 122 which provide for engagement with a connection element of a vial adapter or an IV line adapter 18 to secure syringe adapter 12 to a vial adapter or an IV line adapter 18.

Referring to FIGS. 2A-2C, in one embodiment, syringe adapter 12 includes cannula stabilizing member 28. Cannula stabilizing member 28 includes a distal end 70, a proximal end 72, and an annular ring 74 therebetween. Referring to FIG. 2B, cannula stabilizing member 28 is disposed within cannula seal 22 such that annular ring 74 of cannula stabilizing member 28 engages shoulder portion 44 of cannula seal 22. In this position, cannula stabilizing member 28 supports a portion of cannula 20 and provides stability to cannula 20 during engagement of cannula 20 with a vial or other device. With cannula stabilizing member 28 positioned within cannula seal 22, spring 24 is disposed over cannula 20 and within cannula seal 22 such that distal end 60 of spring 24 engages annular ring 74 of cannula stabilizing member 28. In this manner, spring 24 exerts the biasing force on annular ring 74 of cannula stabilizing member 28 which exerts the biasing force on shoulder portion 44 of cannula seal 22.

Referring to FIGS. 2B and 2C, in one embodiment, syringe adapter 12 includes gliding ring 31. Gliding ring 31 includes an exterior wall surface, i.e., a gliding surface 252 and an interior surface 254. In one embodiment, the interior surface 254 of gliding ring 31 includes an annular protrusion 256. The annular protrusion 256 extends radially inwards from interior surface 254. Referring to FIG. 2B, gliding ring 31 is disposed within housing 29 such that annular protrusion 256 is received within annular cavity 41 of cannula seal 22 to secure the gliding ring 31 to the cannula seal 22 such that the gliding ring 31 is positioned between cannula seal 22 and interior wall surface 118 of housing 29. In this position, gliding ring 31 supports a portion of cannula seal 22 and provides stability to cannula seal 22 within housing 29 during engagement of cannula 20 with a vial or other device. Gliding ring 31 also provides stability to cannula seal 22 with cannula seal 22 moving within housing 29.

Referring to FIGS. 2A-2C, in one embodiment, syringe adapter 12 is configured to provide an aspiration arrangement 230 to allow air to enter the syringe adapter 12 for aspirating air into a syringe barrel while using system 10. In particular, the aspiration arrangement 230 allows a user to aspirate air into the barrel chamber 176 after syringe adapter 12 is secured to the barrel assembly 16. In one embodiment, the aspiration arrangement 230 includes a one-way valve 232 and filter 234. As shown in FIG. 2B, the needle hub 26 includes an inner wall 236 and an outer wall 238 that defines an annular recess 240. The needle hub 26 further defines at least one passageway 242 that extends perpendicularly to a longitudinal axis of the needle hub 26. The passageway 242 extends through the inner wall 236. The outer wall 238 defines a cutout 243 that is configured to receive the filter 234. The cutout 243 is in fluid communication with the passageway 242 and the annular recess 240. In one embodiment, as shown in FIGS. 2A-2C, the filter 234 is a flat filter sheet positioned within the cutout 243, although other suitable arrangements may be utilized. For example, the filter 234 may be ring-shaped and fitted within the annular recess 240 rather than being positioned within the cutout 243. The filter 234 may be any suitable commercially available filter, such as a particulate air filter having a pore size of 0.2 μm or larger. The filter 234 may be configured remove viable micro-organisms.

Referring again to FIG. 2B, in one embodiment, the one-way valve 232 is embodied as an extension 244 of the cannula seal 22 that extends into the needle hub 26. The extension 244 is formed integrally with the cannula seal 22, although the extension 244 may be formed separately. The extension 244 of the cannula seal 22 abuts and extends along at least a portion of an inner surface 246 of the inner wall 236. The extension 244 is configured to selectively allow the flow of outside air through the passageways 242 and the filter 234 and into the cannula seal 22. In particular, in response to a pressure drop within the cannula seal 22 caused by aspiration, the extension 244 will deflect inwardly to open the passageways 242 and allow outside air to be drawn into the barrel chamber 176 of barrel assembly 16. After aspiration, the extension 244 will return to its original position to block or close the passageways 242. When the cannula seal 22 is under a positive pressure, the extension 244 is forced radially outward and continues to block and seal the passageways 242. Air may first be injected into the vial chamber 96 of vial 90 prior to withdrawing fluid, such as substance 98, from the vial chamber 96. Accordingly, the one-way valve 232 and filter 234 allows a user to aspirate air into the barrel chamber 176 after the syringe adapter 12 is secured to the barrel assembly 16. Furthermore, the filter 234 is configured to filter the outside air that is aspirated into the barrel assembly 16, which advantageously allows clean filter air to be injected into the vial chamber 96.

Referring to FIGS. 11-16, proximal end 52 of needle hub 26 is attached to a barrel 160 of barrel assembly 16. With needle hub 26 supporting a portion of cannula 20 and with proximal end 52 of needle hub 26 attached to barrel 160 of barrel assembly 16, needle hub 26 attaches cannula 20 to barrel assembly 16 such that cannula 20 is in fluid communication with barrel chamber 176 of barrel 160 as will be described in more detail below.

Figure 3A:
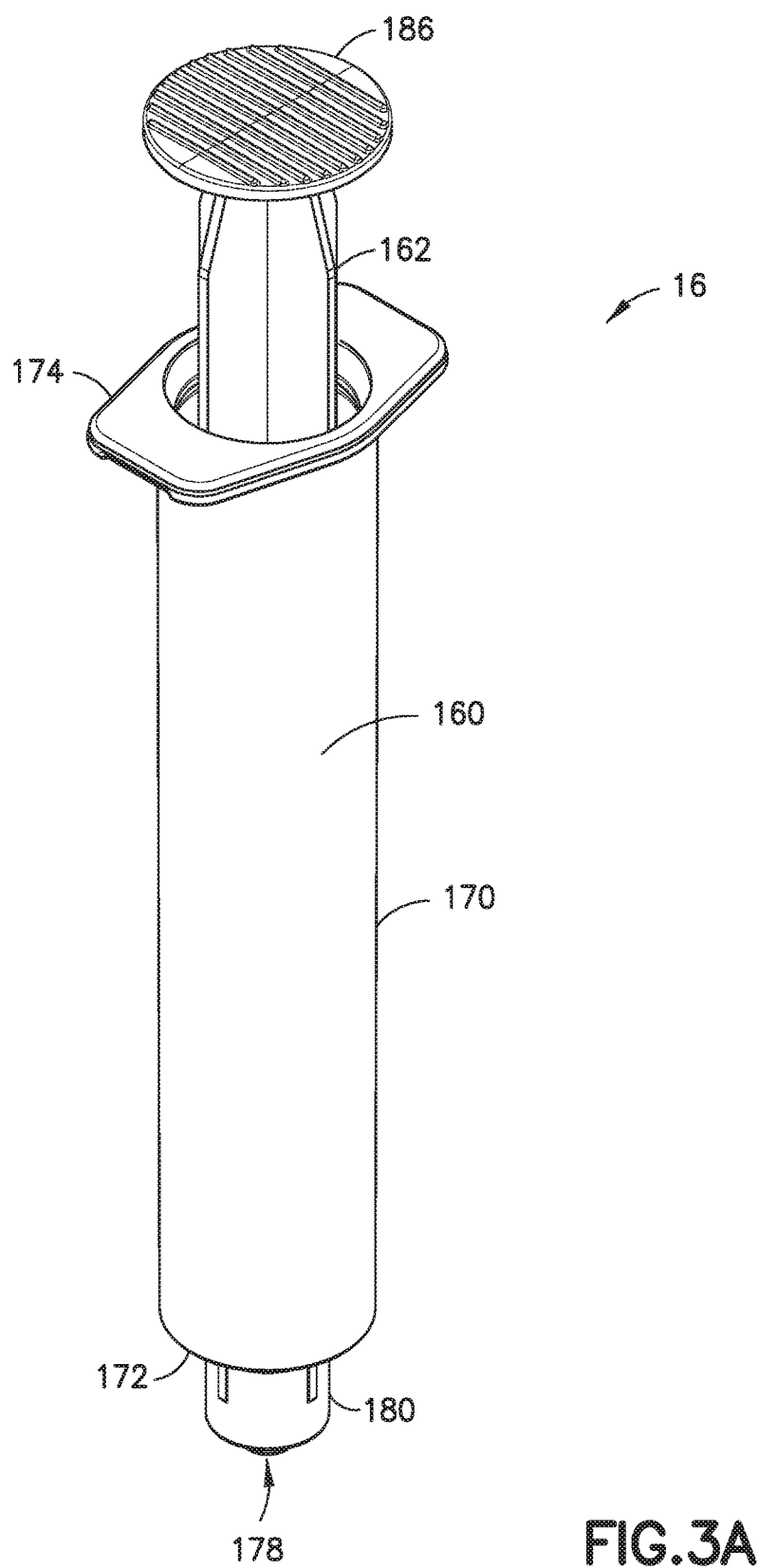
FIG. 3A is a perspective view of a barrel assembly in accordance with an embodiment of the present invention.
Figure 3B:
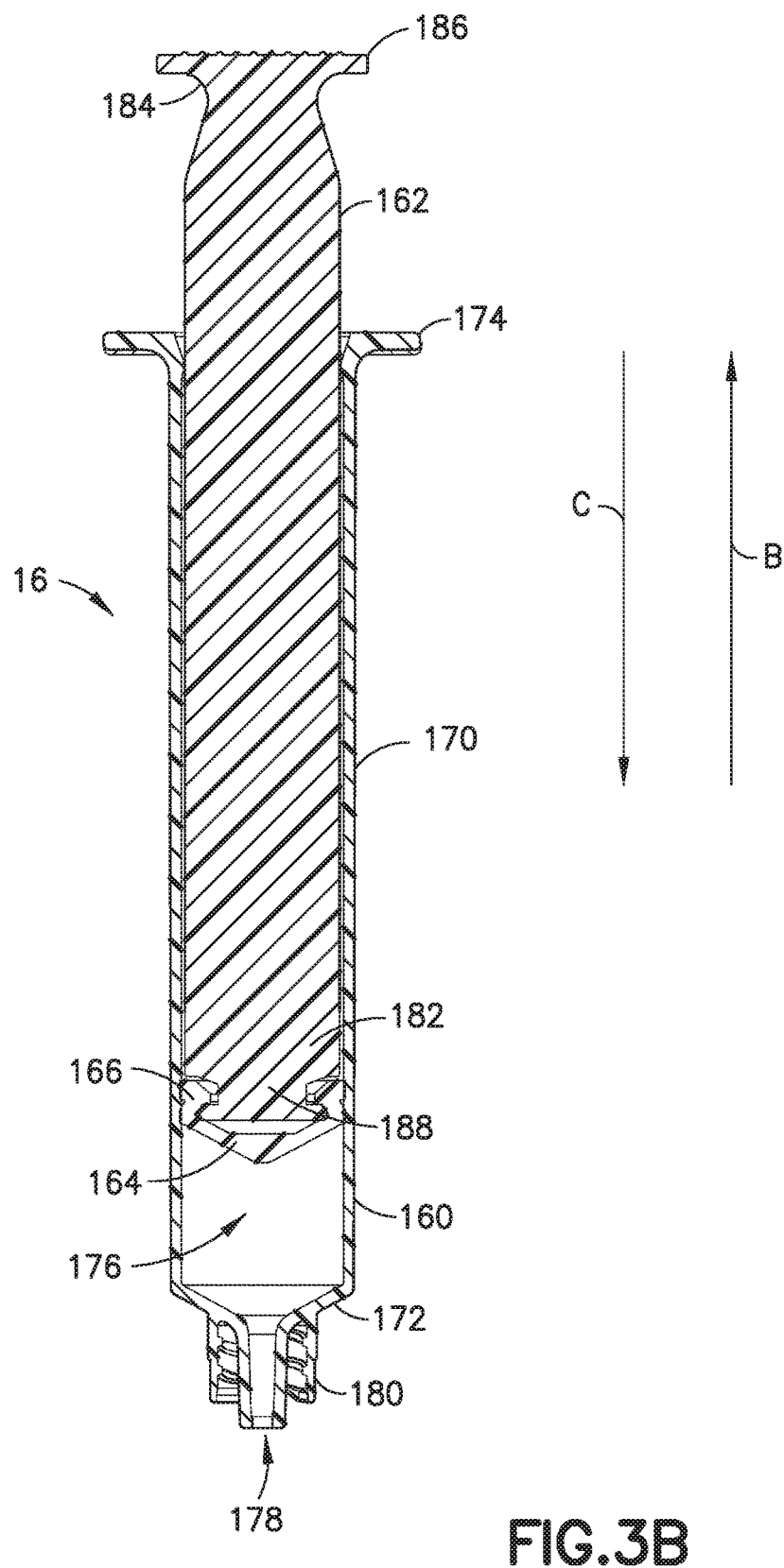
FIG. 3B is a cross-sectional view of the barrel assembly of FIG. 3A with a stopper slidably disposed within a barrel and a plunger rod engaged with a portion of the stopper in accordance with an embodiment of the present invention.

Referring to FIGS. 3A and 3B, barrel assembly 16 includes barrel 160, a plunger rod 162, and a stopper 164. Barrel assembly 16 may be adapted for the dispensing and delivery of a fluid and/or collection of a fluid. For example, barrel assembly 16 may be used for injection or infusion of fluid such as a medication into a patient. Barrel assembly 16 is contemplated for use in connection with a needle, such as by connecting barrel assembly 16 to cannula 20 as described, connecting barrel assembly 16 to a separate needle assembly (not shown), or alternatively for connection with an intravenous (IV) connection assembly such as IV line adapter 18. It can be appreciated that the present disclosure can be used with any type of syringe assembly, including, but not limited to, metered dose syringes, aspiration syringes for withdrawing fluid from a patient or medication from a container or vial, and the like.

Referring to FIGS. 3A and 3B, barrel 160 generally includes a barrel body or sidewall 170 extending between a first or distal end 172 and a second or proximal end 174. Sidewall 170 defines an elongate aperture or barrel chamber 176 of barrel 160. In one embodiment, barrel chamber 176 may span the extent of barrel 160 so that barrel 160 is cannulated along its entire length. In one embodiment, barrel 160 may be in the general form of an elongated cylindrical barrel as is known in the art in the general shape of a hypodermic syringe. In alternative embodiments, barrel 160 may be in other forms for containing a fluid for delivery, such as in the general form of an elongated rectangular barrel, for example. Barrel 160 may be formed of glass, or may be injection molded from thermoplastic material such as polypropylene and polyethylene according to techniques known to those of ordinary skill in the art, though it is to be appreciated that barrel 160 may be made from other suitable materials and according to other applicable techniques.

Referring to FIGS. 3A and 3B, distal end 172 of barrel 160 includes an outlet opening 178 which is in fluid communication with barrel chamber 176. Outlet opening 178 may be sized and adapted for engagement with a separate device, such as cannula 20, a needle assembly, or an IV connection assembly and, therefore, may include a mechanism for such engagement and as is conventionally known. For example, distal end 172 may include a generally-tapered luer tip for engagement with an optional separate tapered luer mating surface of such a separate device for attachment therewith, such as barrel connecting portion 54 of the syringe adapter 12. Distal end 172 of barrel 160 also includes a mechanism for locking engagement with needle hub 26, such as a needle hub connection portion 180. In one embodiment, needle hub connection portion 180 is a threaded portion. Referring to FIGS. 11-16, needle hub 26 is attached to barrel 160 by securing barrel connection portion 54 of needle hub 26 to needle hub connection portion 180 of barrel 160.

Proximal end 174 of barrel 160 is generally open-ended, but is intended to be closed off to the external environment as will be discussed herein. Barrel 160 may also include fill lines, such as graduations located on sidewall 170, for providing an indication as to the level or amount of fluid contained within barrel chamber 176 of barrel 160. Such markings may be provided on an external surface of sidewall 170, an internal surface of sidewall 170, or integrally formed or otherwise within sidewall 170. In other embodiments, alternatively, or in addition thereto, the markings may also provide a description of the contents of the syringe or other identifying information such as maximum and/or minimum fill lines.

Referring to FIGS. 3A and 3B, barrel assembly 16 includes stopper 164 which is movably or slidably disposed within barrel chamber 176, and in sealing contact with the internal surface of sidewall 170 of barrel 160. Stopper 164 is sized relative to barrel 160 to provide sealing engagement with the interior surface of sidewall 170 of barrel 160. Additionally, stopper 164 may include one or more annular ribs extending around the periphery of stopper 164 to increase the sealing engagement between stopper 164 and the interior surface of sidewall 170 of barrel 160.

Referring to FIGS. 3A and 3B, in one embodiment, stopper 164 also includes an engagement portion 166 for securing plunger rod 162 to stopper 164. In one embodiment, engagement portion 166 of stopper 164 may include a threaded portion for engagement with a threaded portion of plunger rod 162. In other embodiments, engagement portion 166 of stopper 164 may include a snap fit mechanism, a ball detent, locking tabs, spring loaded locking mechanism, latch, adhesive, or other similar mechanism. In another embodiment, plunger rod 162 and stopper 164 may be co-formed such as by co-extrusion.

Referring to FIGS. 3A and 3B, barrel assembly 16 includes plunger rod 162 which provides a mechanism for dispensing fluid contained within barrel chamber 176 of barrel 160 through outlet opening 178 to cannula 20 upon connection of plunger rod 162 to barrel 160 via stopper 164. Plunger rod 162 is adapted for advancing stopper 164. In one embodiment, plunger rod 162 is sized for movement within barrel chamber 176 of barrel 160 to actuate stopper 164 between a first position adjacent distal end 172 of barrel 160 and a second position adjacent proximal end 174 of barrel 160. Referring to FIGS. 3A and 3B, plunger rod 162 includes a distal end 182, a proximal end 184, a flange portion 186 disposed at proximal end 184, and a securement feature or engagement portion 188 for securing plunger rod 162 to stopper 164 as described above.

Figure 4C:
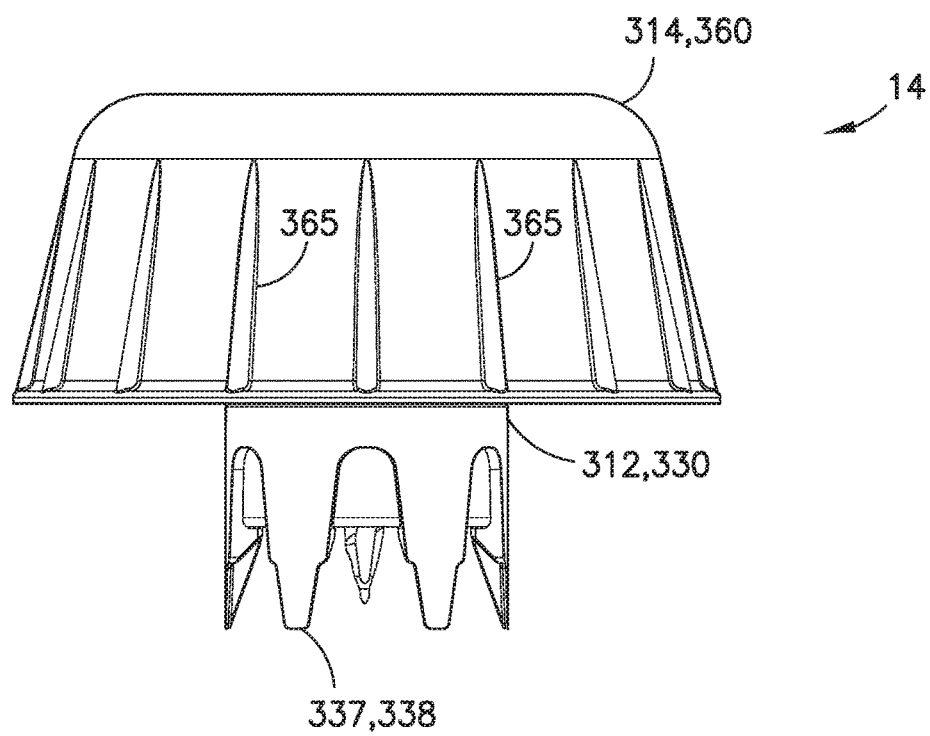
FIG. 4C is a side, perspective view of a vial adapter in accordance with an embodiment of the present invention.
Figure 4D:
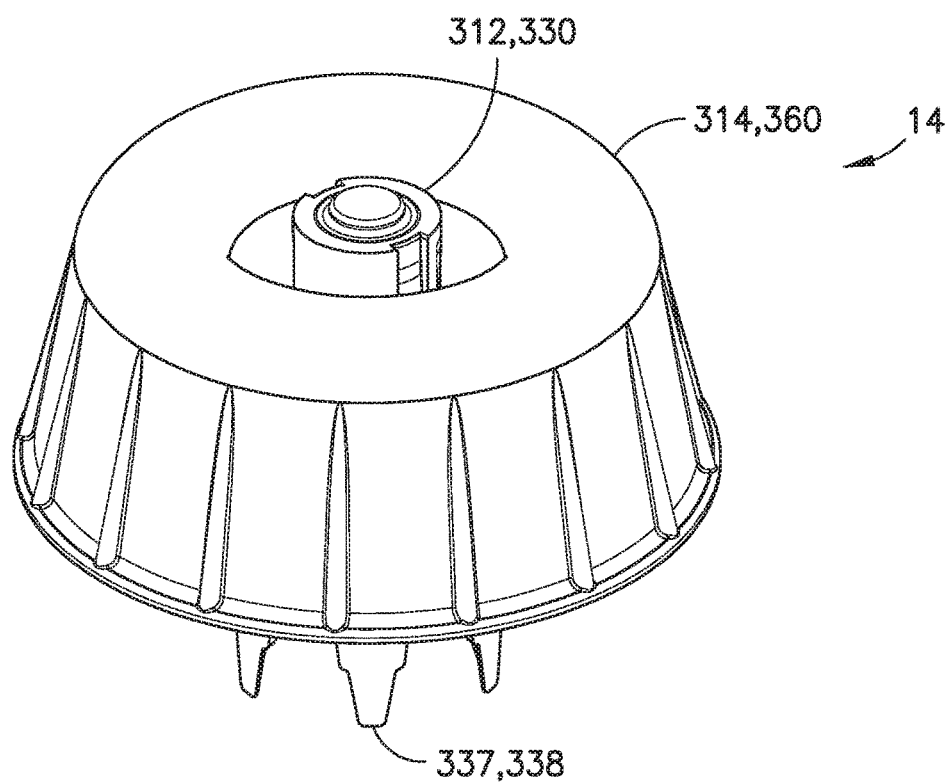
FIG. 4D is a perspective view of a vial adapter in accordance with an embodiment of the present invention.
Figure 4E:
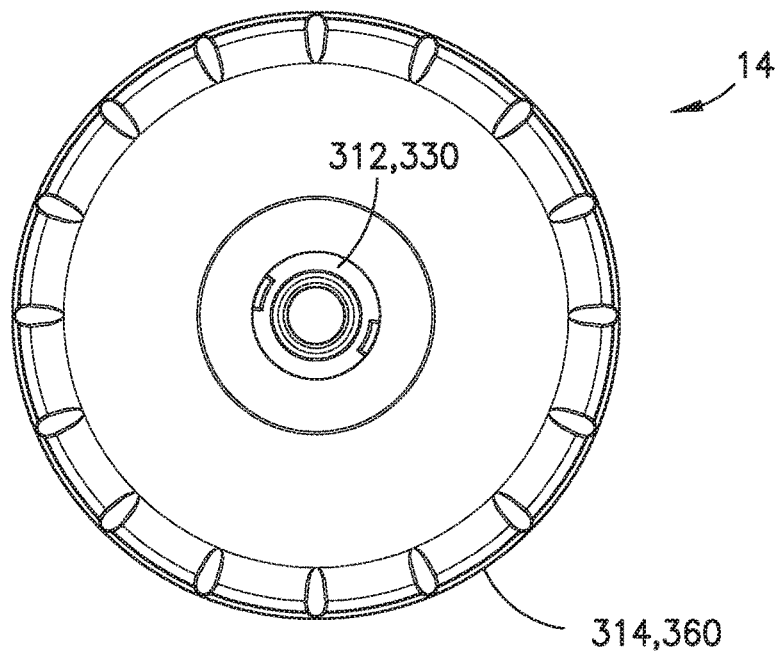
FIG. 4E is a plan view of a vial adapter in accordance with an embodiment of the present invention.
Figure 4F:
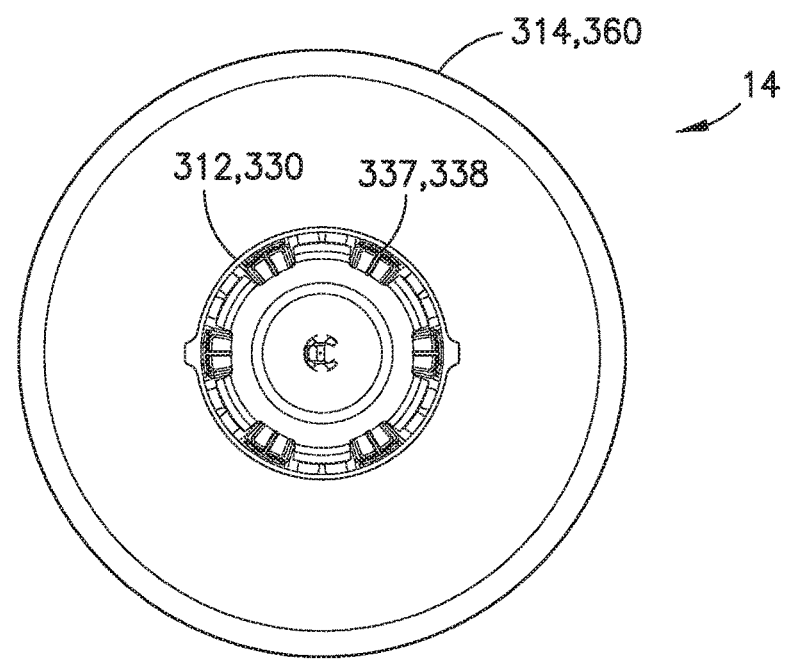
FIG. 4F is a bottom view of a vial adapter in accordance with an embodiment of the present invention.
Figure 4G:
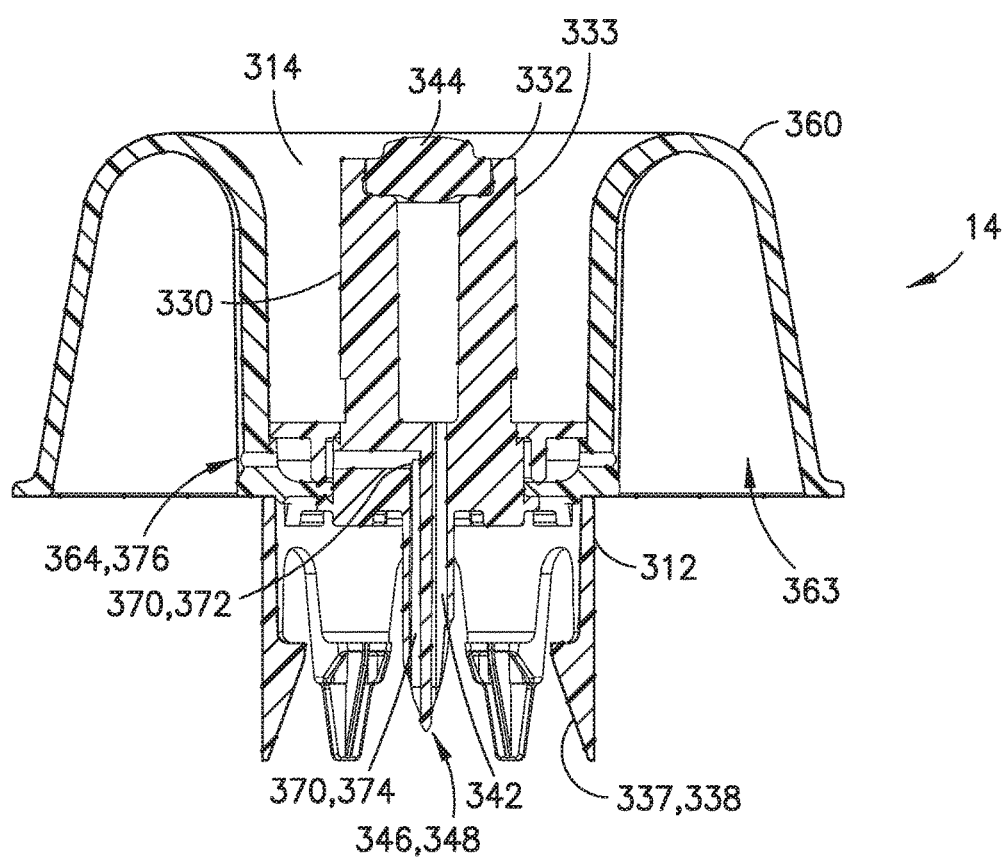
FIG. 4G is a cross-sectional view of the vial adapter of FIG. 4C in accordance with an embodiment of the present invention.
Figure 4H:
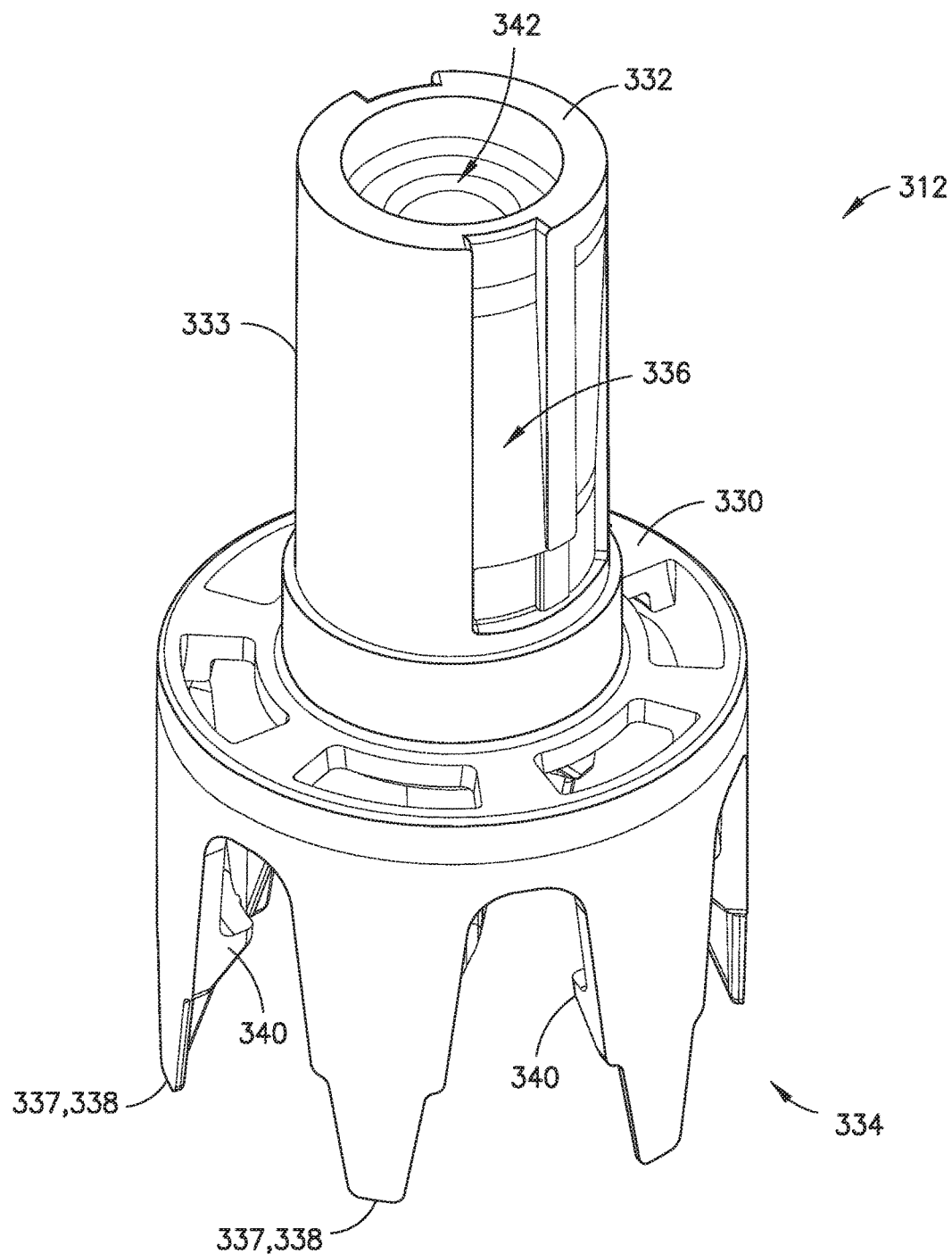
FIG. 4H is a perspective view of a vial access system in accordance with an embodiment of the present invention.
Figure 4I:
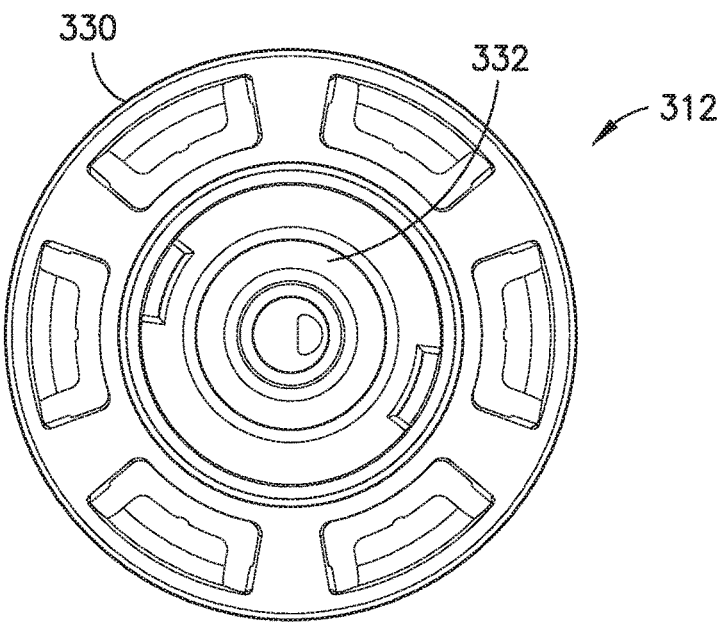
FIG. 4I is a plan view of a vial access system in accordance with an embodiment of the present invention.
Figure 4J:
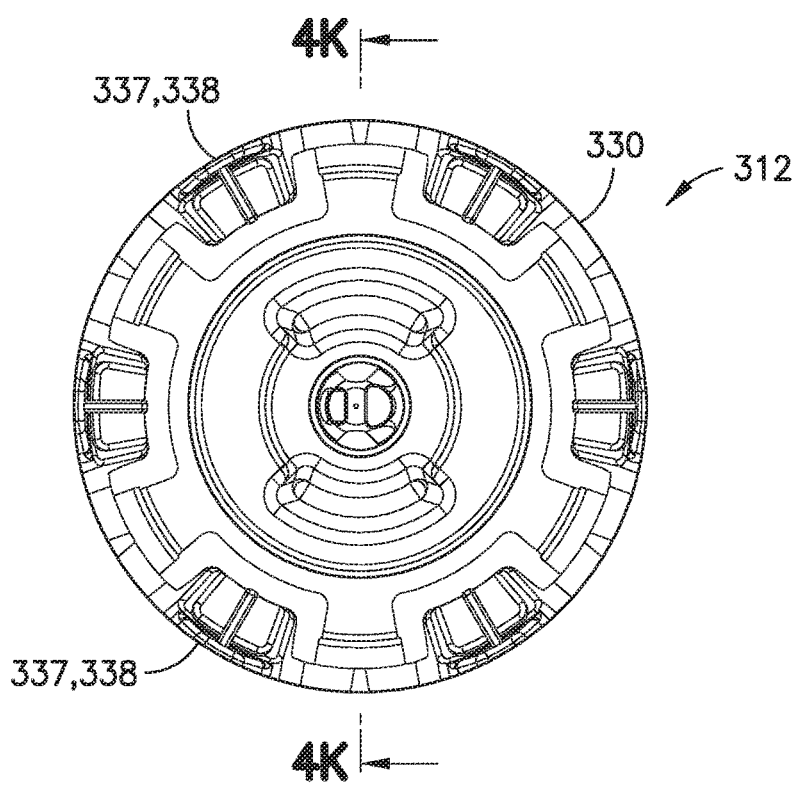
FIG. 4J is a bottom view of a vial access system in accordance with an embodiment of the present invention.
Figure 4K:
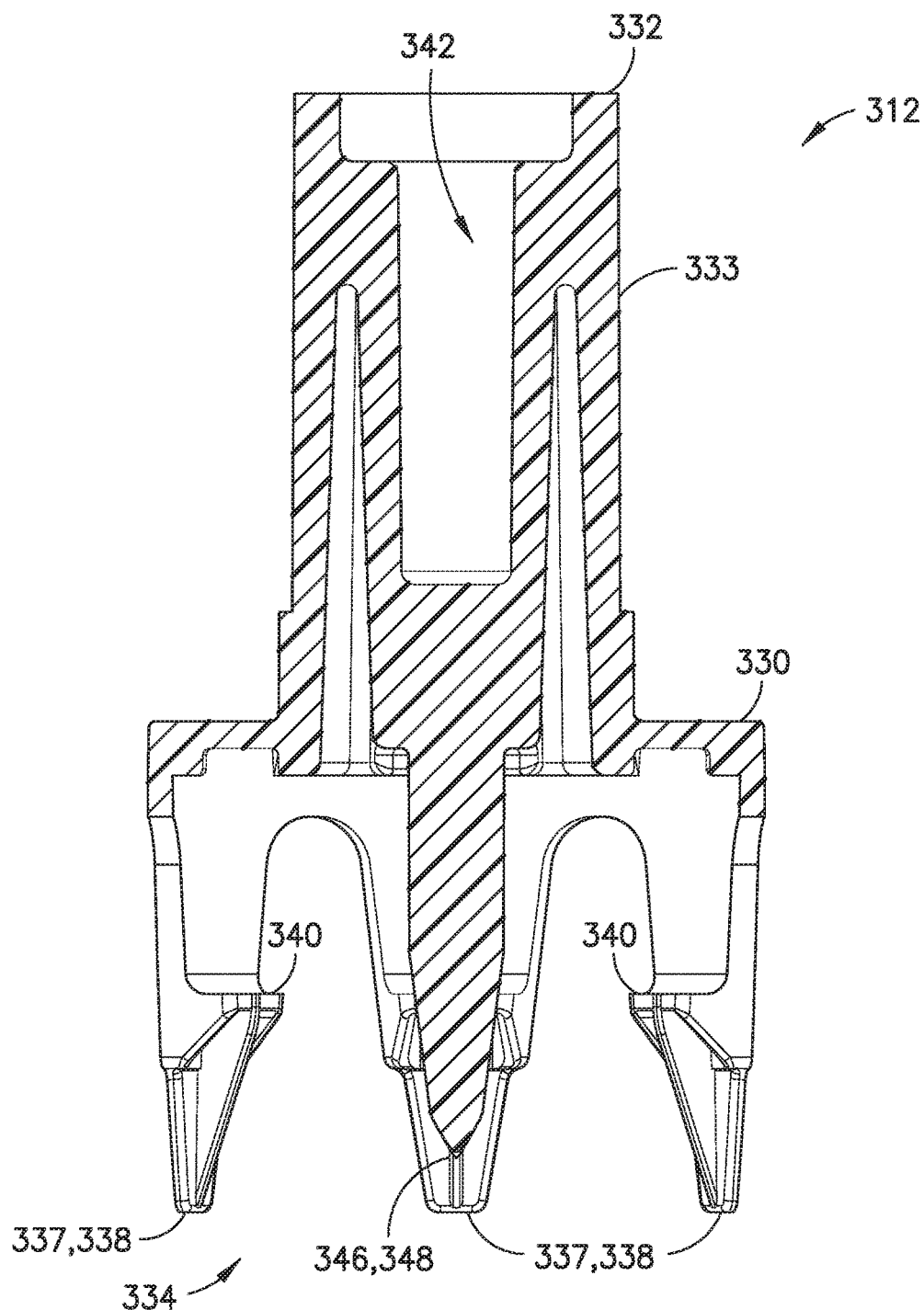
FIG. 4K is a cross-sectional view of a vial access system taken along line 4K-4K of FIG. 4J in accordance with an embodiment of the present invention.
Figure 4L:
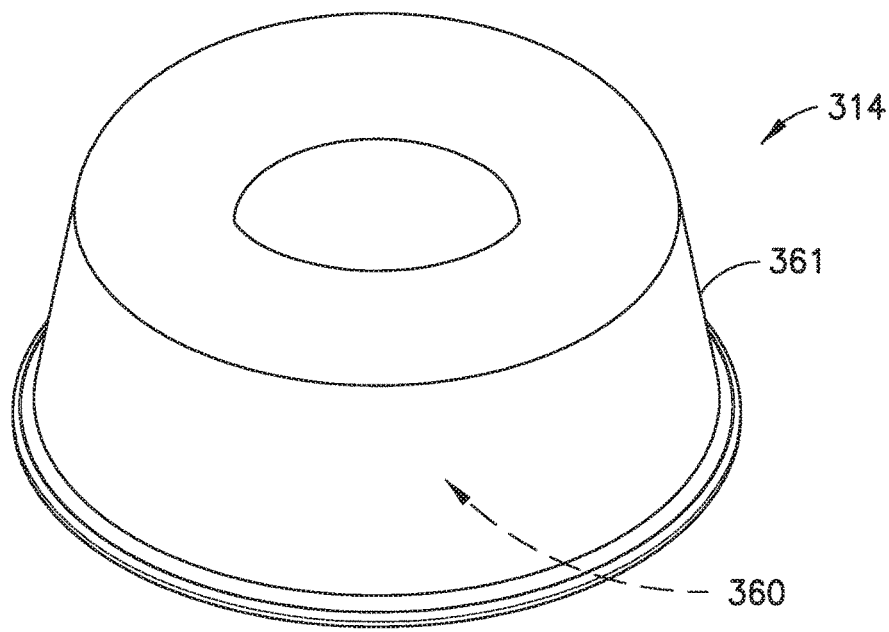
FIG. 4L is a perspective view of a pressure equalization system in accordance with an embodiment of the present invention.
Figure 4M:
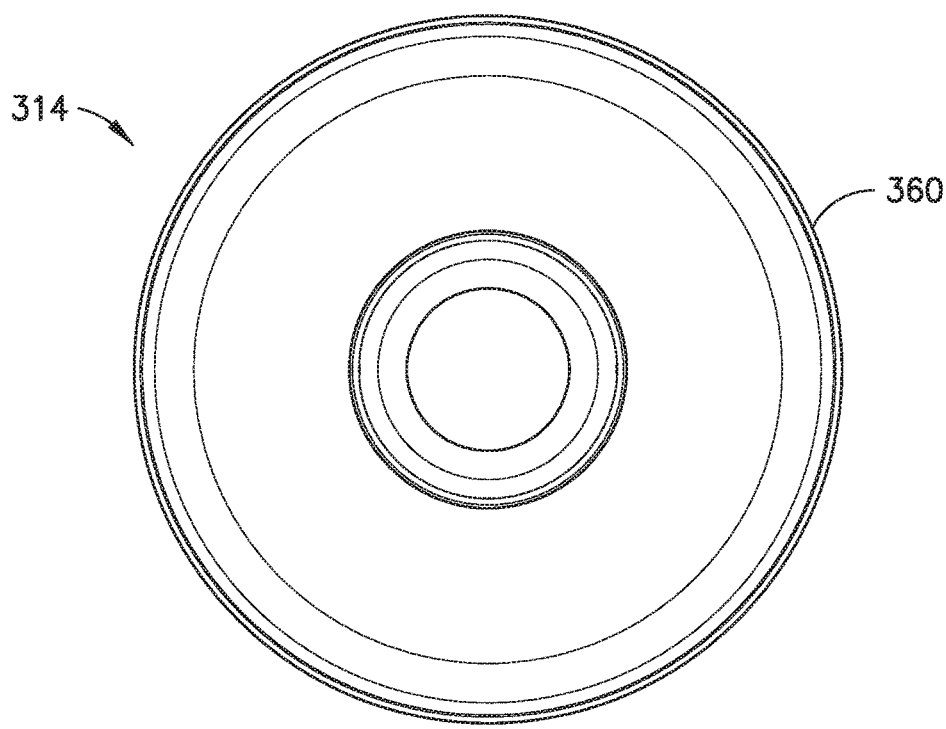
FIG. 4M is a plan view of a pressure equalization system in accordance with an embodiment of the present invention.
Figure 4N:
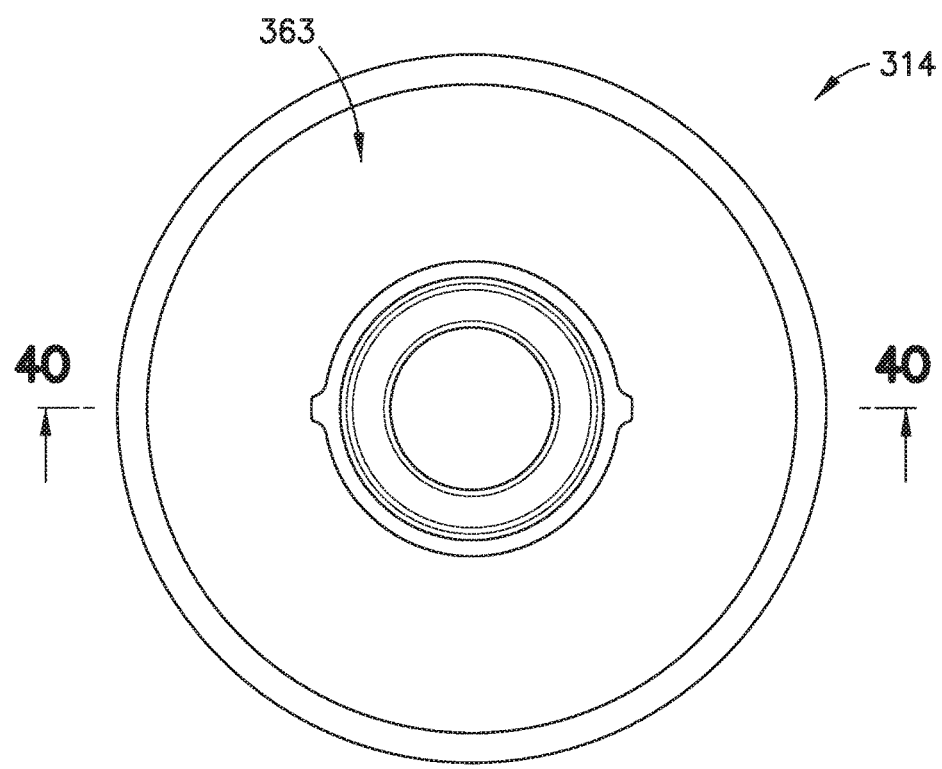
FIG. 4N is a bottom view of a pressure equalization system in accordance with an embodiment of the present invention.
Figure 4O:
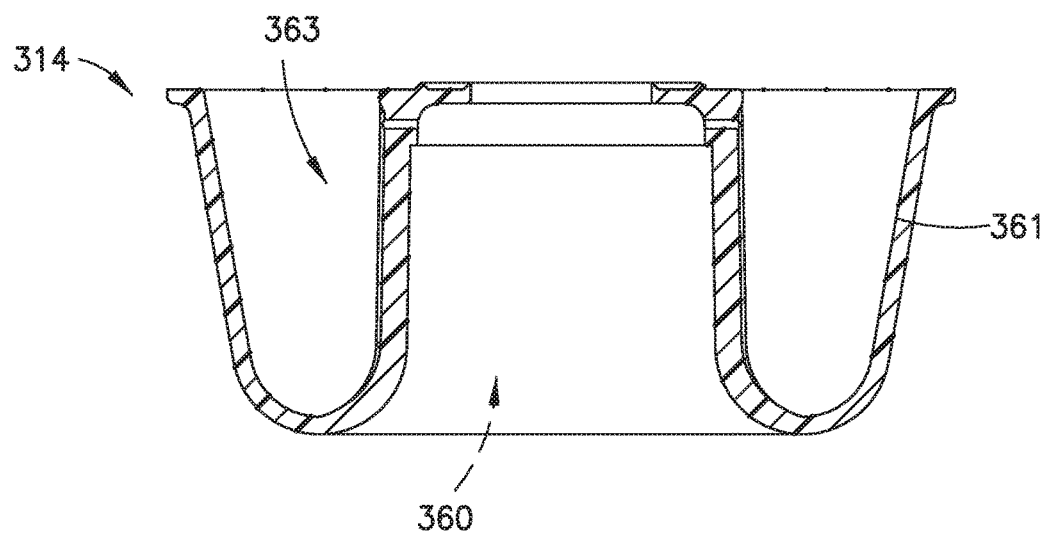
FIG. 4O is a cross-sectional view of a pressure equalization system taken along line 4O-4O of FIG. 4N in accordance with an embodiment of the present invention.
Figure 5:
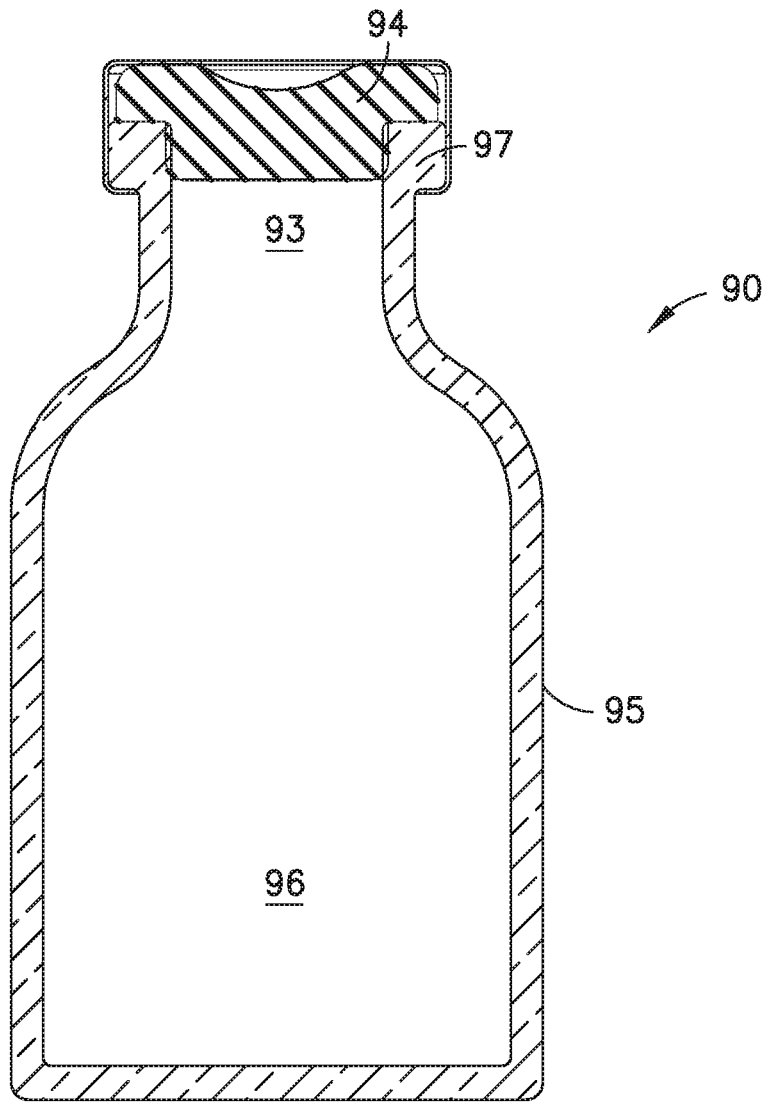
FIG. 5 is a cross-sectional view of a vial in accordance with an embodiment of the present invention.

Referring to FIGS. 4A-4O, vial adapter 14 includes a vial access system 312 and a pressure equalization system 314. Vial adapter 14 is configured to establish fluid communication between a first container and a second container. For example, vial adapter 14 is attachable to a vial 90. Referring to FIG. 5, vial 90 may be a standard drug vial of any type having an open head portion 93 covered by a pierceable septum 94 of an elastomeric material. Walls 95 of vial 90 define vial chamber 96 for containing a substance 98. Vial septum 94 is engaged with head portion 93 of vial 90 to seal the substance 98 within vial chamber 96.

As shown in FIGS. 4A-4G, with pressure equalization system 314 secured to vial access system 312, vial adapter 14 includes first end 302, opposing second end 303, and wall 304 extending between first end 302 and second end 303. Wall 304 defines an exterior profile 306. With vial adapter 14 attached to a vial 90, the vial adapter 14 provides a leak-proof seal and pressure equalization system that prevents any substance contained within a chamber of the vial from being exposed to a health care provider reconstituting, transporting, or administering a drug.

The fit between vial adapter 14 and the packaging member provides a secure fit therebetween, such that, with vial adapter 14 received within the packaging member, the packaging member can be used as an interface between the hand of a user and vial adapter 14 so that vial adapter 14 can be placed onto a vial 90 without taking vial adapter 14 out of the packaging member.

Referring to FIGS. 4H-4K, vial access system 312 of vial adapter 14 includes vial access housing 330 having first end 332 and opposing second end 334. First end 332 of vial access housing 330 includes a first connection element or connection system 336. First connection element 336 is engageable with a connection element 120, 122 of a syringe adapter 12 to secure the syringe adapter 12 to vial adapter 14. In one embodiment, first end 332 of vial access housing 330 includes a second connection element or second connection system 339. Second connection element 339 is spaced a distance from first connection element 336. In one embodiment, second connection element 339 is spaced approximately 180 degrees (180°) from first connection element 336. Second connection element 339 is engageable with a connection element 120, 122 of a syringe adapter 12 to secure the syringe adapter 12 to vial adapter 14 such that significant relative movement between syringe adapter 12 and vial adapter 14 is prevented.

First end 332 of vial access housing 330 is substantially formed by a neck portion 333. In one embodiment, neck portion 333 may include a guiding groove arranged therein to guide corresponding guiding protrusions on a cannula adapter or syringe assembly, for example, to establish a secure attachment between the cannula adapter or syringe assembly and vial adapter 14 after which fluid communication can be established.

Figure 7A:
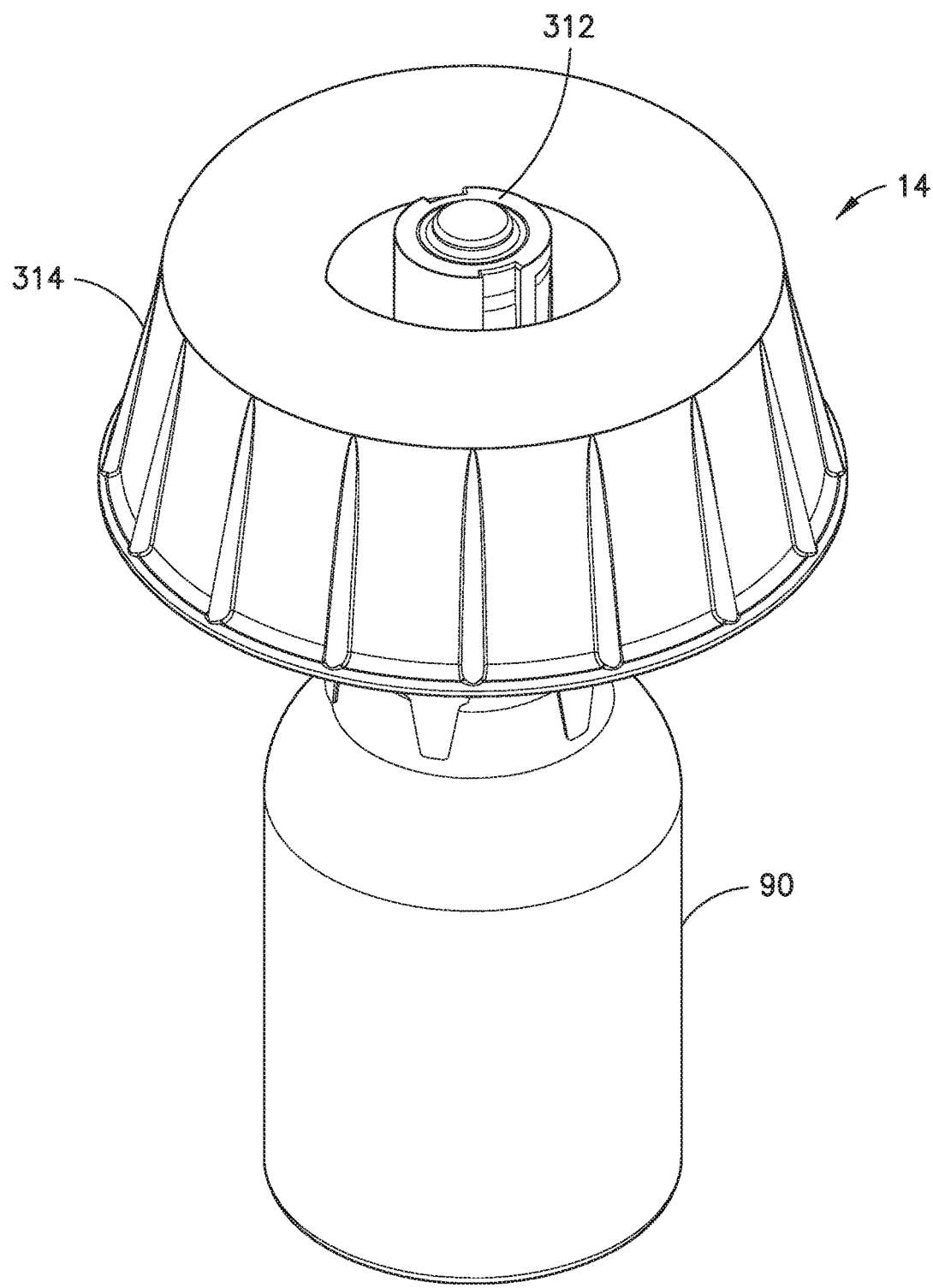
FIG. 7A is a perspective view of a vial adapter connected to a vial in accordance with an embodiment of the present invention.
Figure 7B:
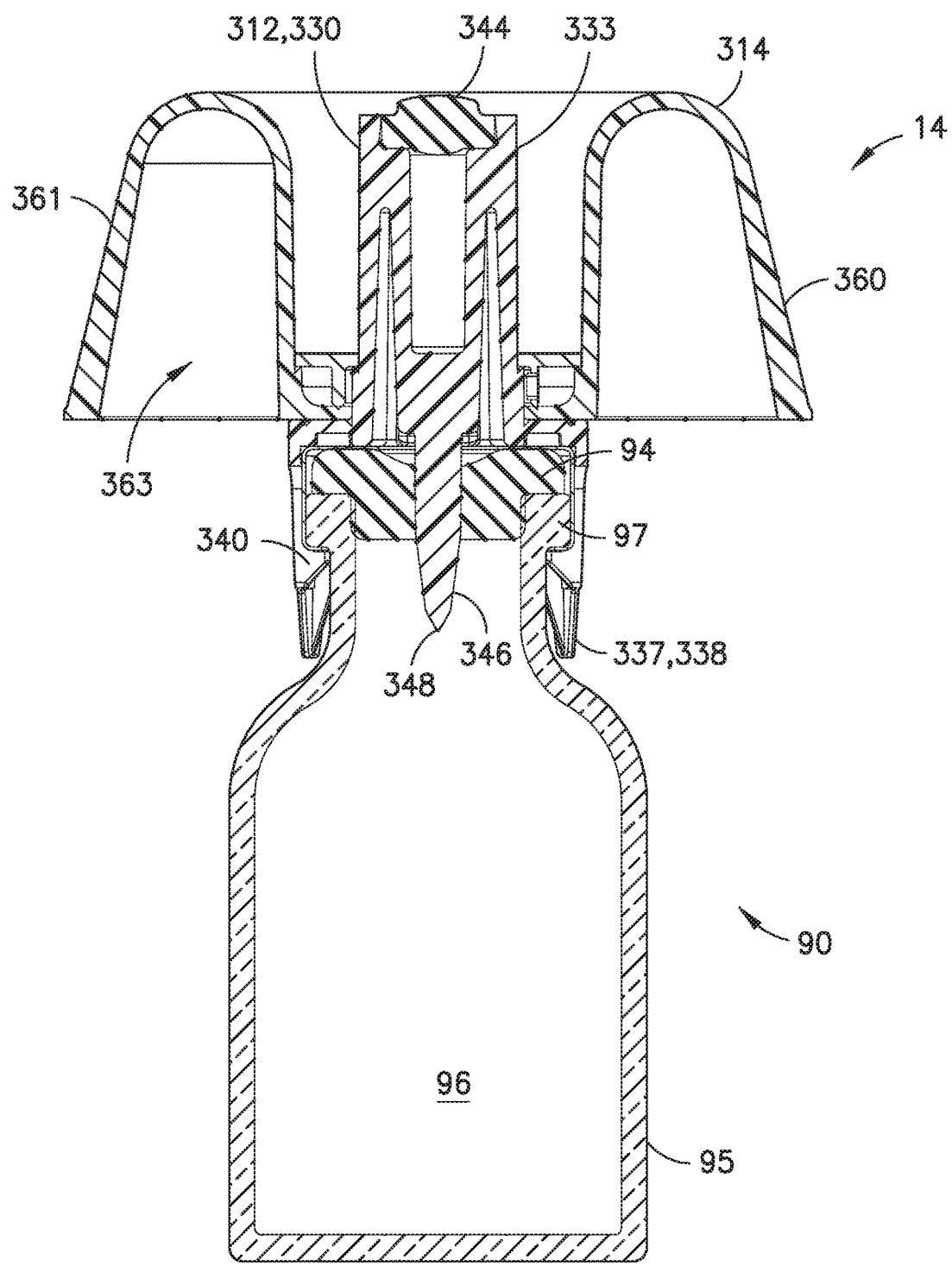
FIG. 7B is a cross-sectional view of the vial adapter connected to the vial of FIG. 7A in accordance with an embodiment of the present invention.
Figure 8:
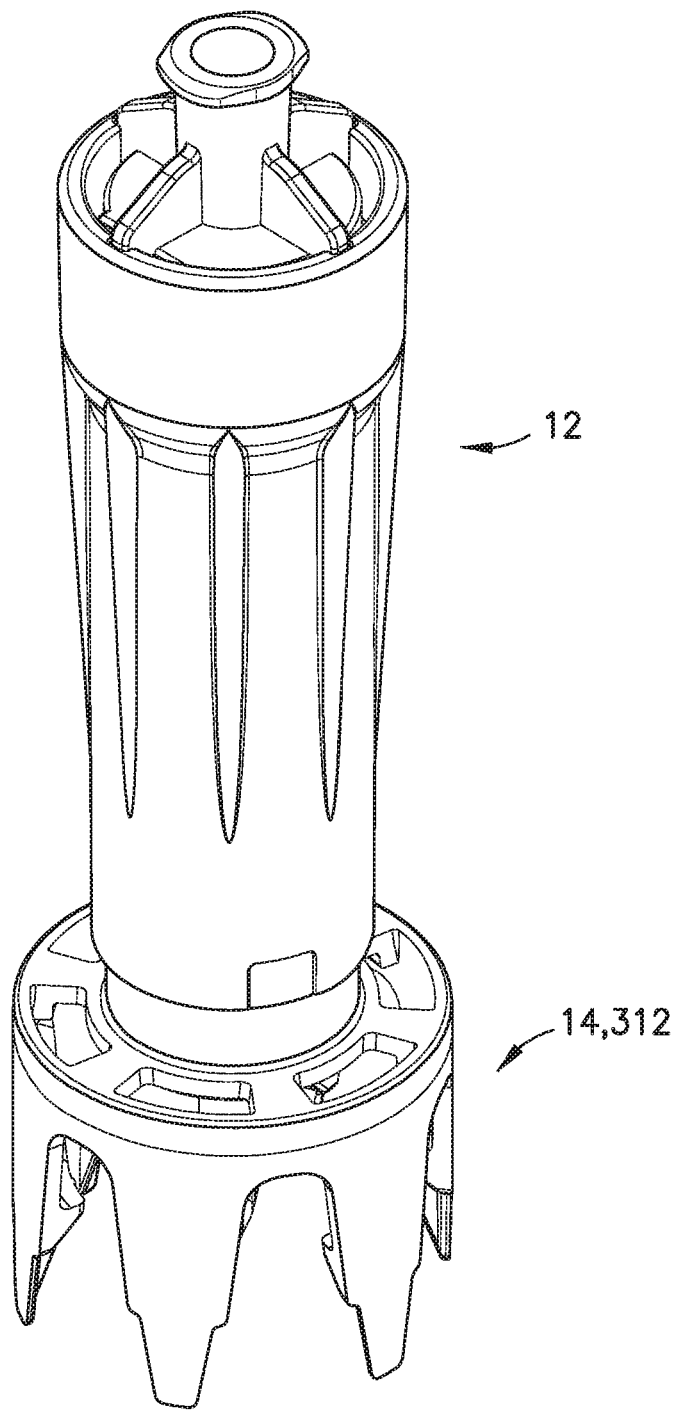
FIG. 8 is a perspective view of a syringe adapter connected to a portion of a vial adapter in accordance with an embodiment of the present invention.
Figure 9A:
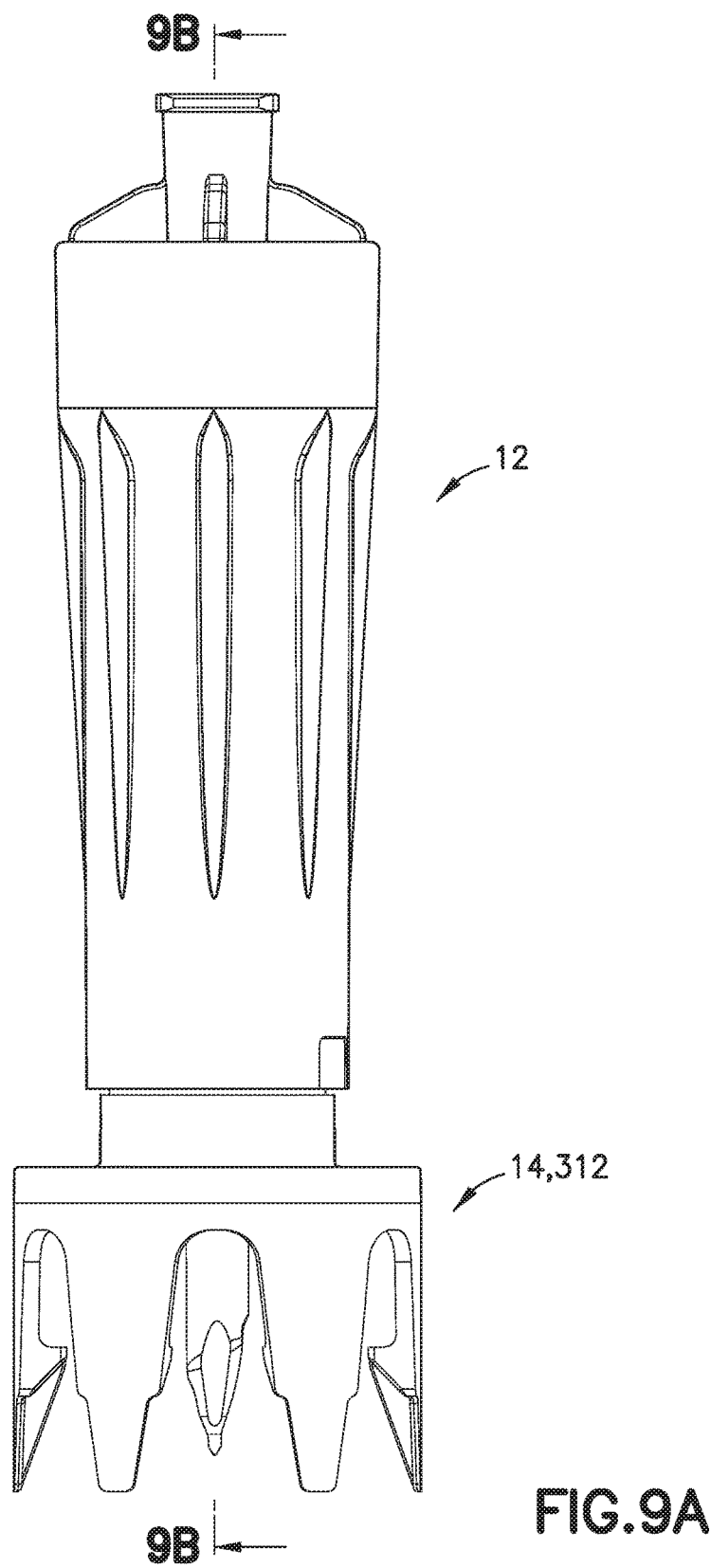
FIG. 9A is a perspective view of a syringe adapter connected to a portion of a vial adapter in accordance with an embodiment of the present invention.
Figure 9B:
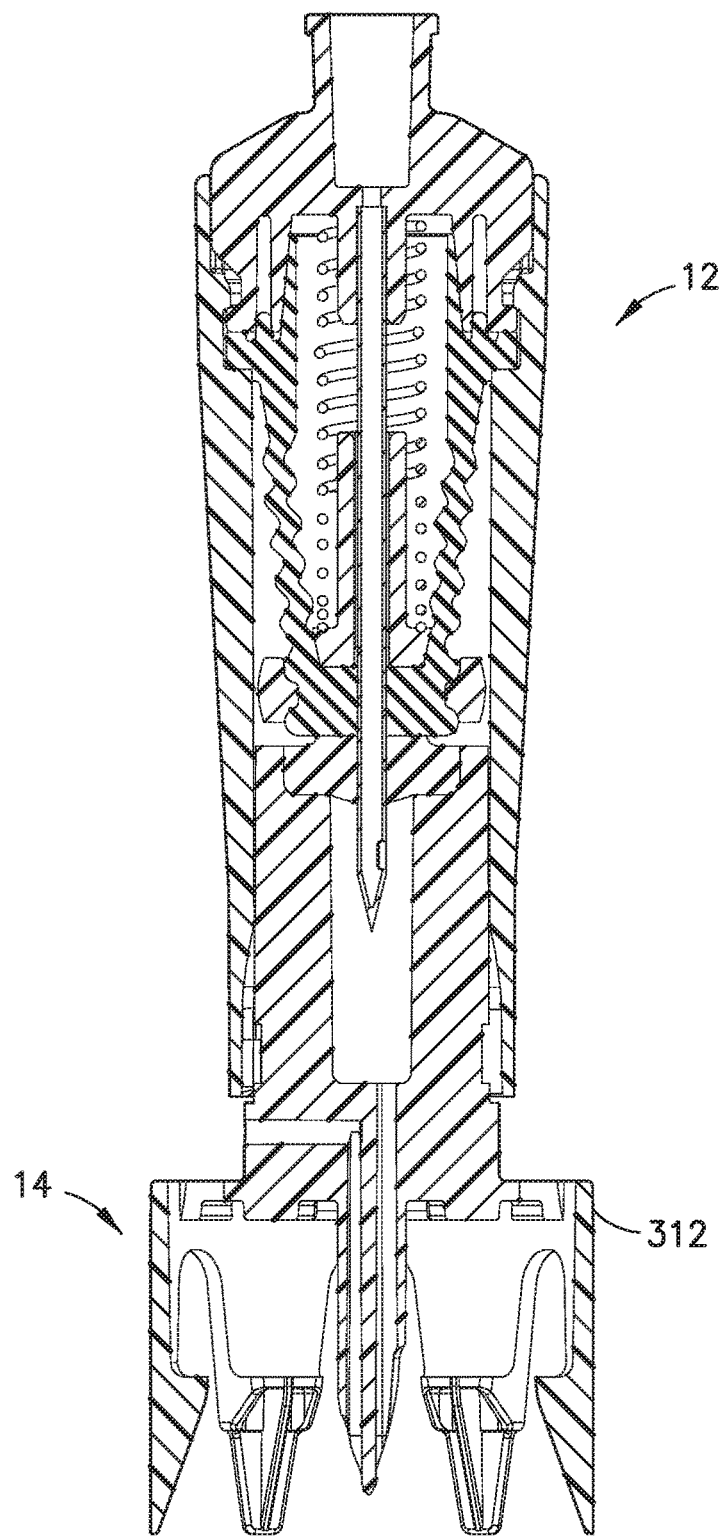
FIG. 9B is a cross-sectional view of the syringe adapter connected to a portion of the vial adapter taken along line 9B-9B of FIG. 9A in accordance with an embodiment of the present invention.
Figure 10:
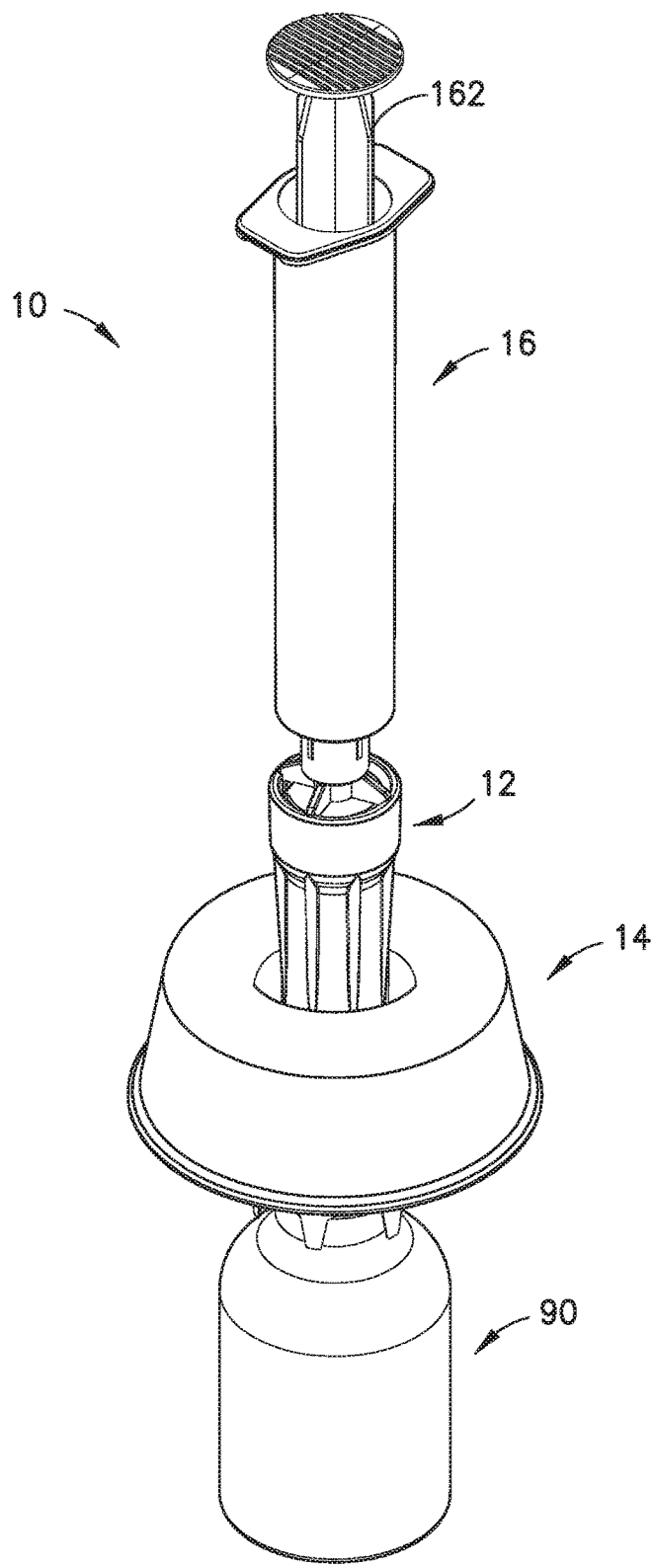
FIG. 10 is an assembled, perspective view of a system in accordance with an embodiment of the present invention.

Referring to FIGS. 4H-4K, a vial connection member or vial engagement member 337 is disposed at second end 334 of vial access housing 330. In one embodiment, vial connection member 337 includes a plurality of vial grip members 338 that are disposed at second end 334 of vial access housing 330. Vial grip members 338 are attachable to a vial 90 to secure vial adapter 14 to the vial 90. Each vial grip member 338 includes a hook protrusion 340 arranged to engage a corresponding flange on a container such as a vial 90 as shown in FIGS. 7A and 7B. Vial connection member 337 of vial access housing 330 may be dimensioned to be attached to containers of any size and volume. In other embodiments, vial connection member 337 of vial access housing 330 may include other connection mechanisms for securing vial adapter 14 to vial 90 such as a threaded portion, a snap fit mechanism, locking tabs, or other similar mechanism.

A fluid transfer channel 342 extends substantially between first end 332 and second end 334 of vial access housing 330. The purpose of fluid transfer channel 342 is to permit a needle cannula to extend through vial access housing 330 of vial adapter 14 and to thereby permit fluid to be transferred through vial adapter 14.

Figure 13:
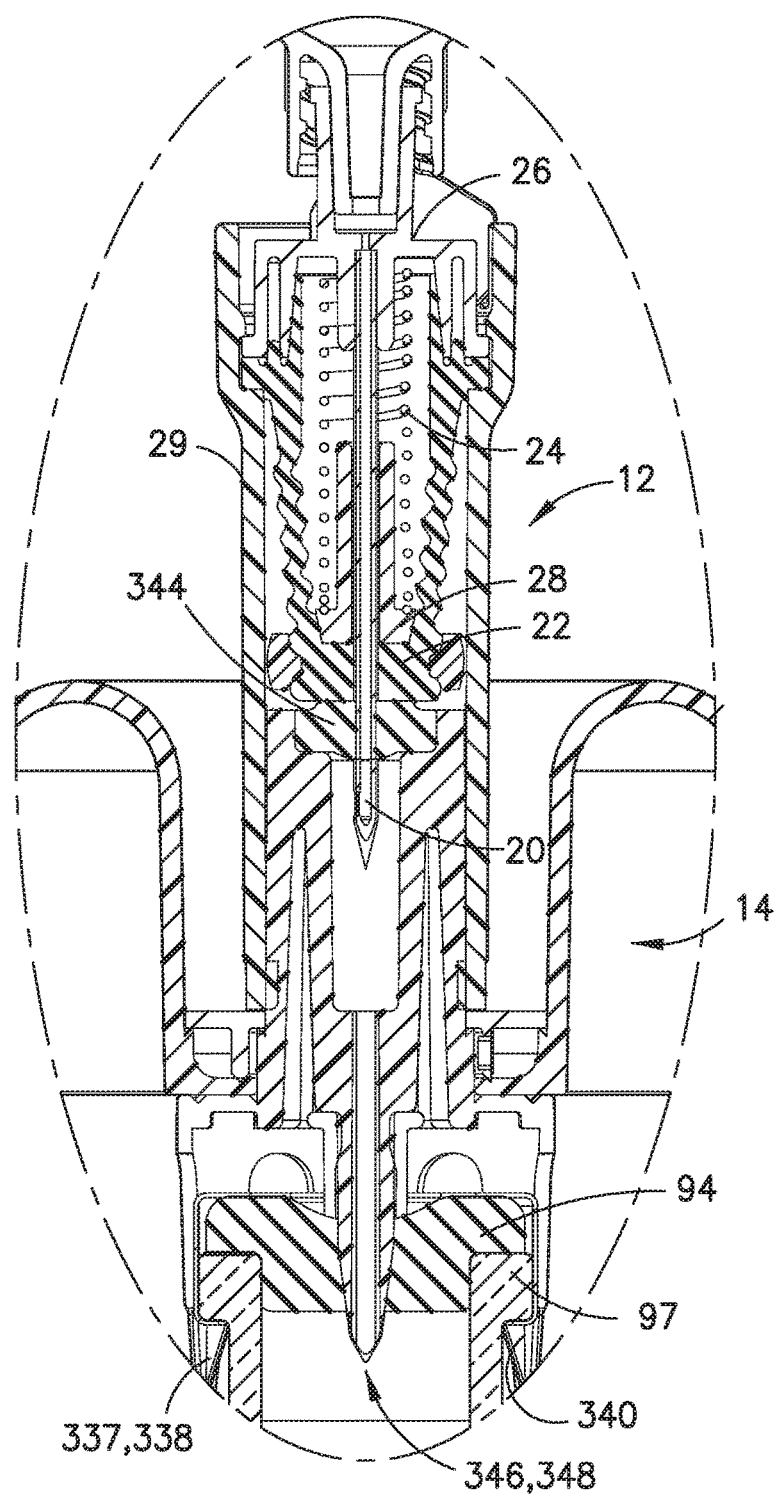
FIG. 13 is a detailed, fragmentary view of FIG. 12B in accordance with an embodiment of the present invention.
Figure 14:
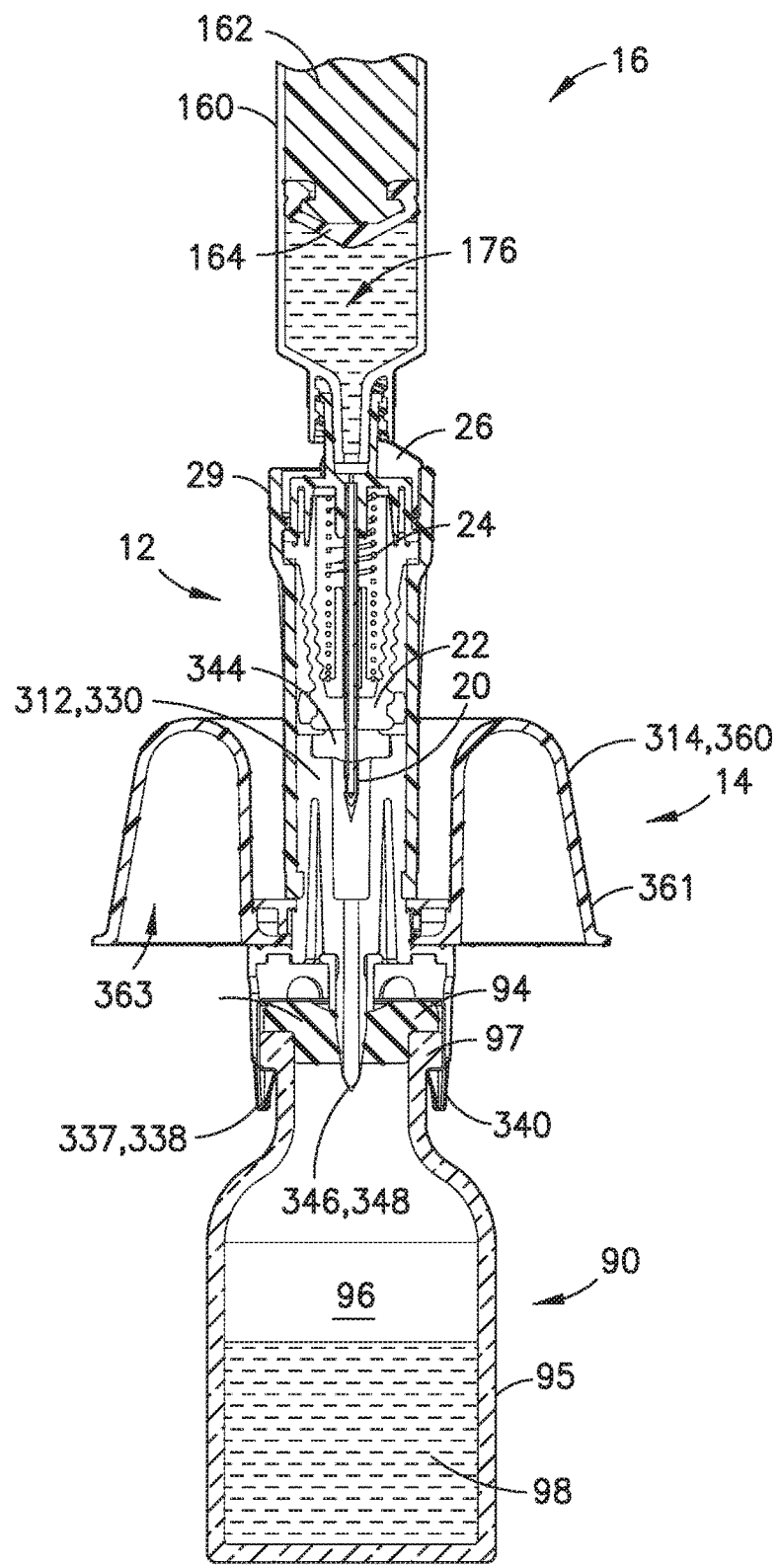
FIG. 14 is a cross-sectional view of the system of FIG. 10 with the cannula seal in communication with the vial seal in accordance with an embodiment of the present invention.

Referring to FIG. 7B, a pierceable barrier member or vial seal membrane 344 is arranged in the fluid transfer channel 342 at first end 332 of vial access housing 330. The pierceable barrier member 344 provides for a liquid and gas tight seal between a piercing member and the pierceable barrier member 344 during fluid transfer so to minimize leakage and thereby prevent exposure of hazardous medicaments to a user. Vial seal membrane 344 provides a self-sealing seal that, with vial adapter 14 attached to vial 90 such that vial seal membrane 344 is aligned with vial septum 94, provides a leak-proof seal preventing any substance contained within vial chamber 96 from being exposed to a health care provider reconstituting, transporting, or administering a drug using system 10. Referring to FIGS. 13-15, vial seal membrane 344, vial sleeve seal 350, and cannula seal 22 provide a leak-proof seal that is liquid tight and airtight preventing any substance residue from being exposed to a health care provider while reconstituting or withdrawing substance 98 from vial 90 to barrel 160 via cannula 20 as will be described in more detail below.

In one embodiment, vial seal membrane 344 comprises a resilient material. For example, vial seal membrane 344 is preferably a unitary device molded of any flexible, elastomeric material conventionally used for fabricating gas-proof closures. Vial seal membrane 344 may be formed of a natural rubber material, polyurethane elastomers, butyl rubbers, or similar materials. It is contemplated that vial seal membrane 344 is formed of a material having a Shore A hardness of approximately 10 to 50. It is also envisioned that vial seal membrane 344 can have other material hardness values that would provide an appropriate self-sealing material to provide a leak-proof seal with vial septum 94 of vial 90 and cannula seal 22, thereby preventing any liquid or medication residue from being exposed to a health care provider reconstituting, transporting, or administering a drug using system 10.

Protruding out from vial access housing 330 at second end 334 is a piercing member or spike member 346 which includes piercing tip 348. In one embodiment, fluid transfer channel 342 extends inside of spike member 346. The spike member 346 extends in a direction substantially parallel with the plurality of vial grip members 338 and serves the purpose of piercing a fluid container such as a vial 90 during assembly of vial adapter 14 to a vial 90 as is shown in greater detail in FIG. 7B.

In one embodiment, a vial sleeve seal 350 is disposed over the spike member 346. The vial sleeve seal 350 provides a seal between vial adapter 14 and a vial 90 with the piercing tip 348 of spike member 346 engaged with the vial 90. In one embodiment, vial sleeve seal 350 comprises a rubber spike sleeve.

Referring to FIGS. 4L-4O, pressure equalization system 314 includes pressure equalization housing 360 and toroidal expandable balloon 362 which includes an expansion chamber 366. Pressure equalization housing 360 defines a tapered exterior wall portion 361 and an interior annular ring cavity portion 363. In one embodiment, tapered exterior wall portion 361 includes a plurality of stabilizing ribs 365. In one embodiment, stabilizing ribs 365 may extend in an axial direction along tapered exterior wall portion 361 of pressure equalization housing 360 and the ribs 365 may be spaced around a periphery of pressure equalization housing 360. Expandable balloon 362 includes a variable volume. Pressure equalization housing 360 comprises a relatively rigid material and expandable balloon 362 comprises a relatively flexible material. In one embodiment, expandable balloon 362 comprises a thin, transparent plastic film that is attached to pressure equalization housing 360 in a gastight manner. In one embodiment, expandable balloon 362 is designed as a bellow which is compressible and extendable and, thus, the volume of the expansion chamber 366 of expandable balloon 362 can thereby be increased and decreased. In one embodiment, interior annular ring cavity portion 363 of pressure equalization housing 360 extends radially around vial access housing 330 and expandable balloon 362 extends radially around vial access housing 330.

Pressure equalization housing 360 provides a barrier wall member that protects expandable balloon 362 from being torn during engagement of a cannula with a vial 90, during transfer of a substance from a vial chamber to a barrel chamber via the cannula 20, and during disengagement of the cannula 20 from the vial 90. In one embodiment, by having expandable balloon 362 extending radially around the entirety of vial access housing 330, the vial adapter 14 is balanced such that a center of mass is positioned at about a longitudinal axis of vial adapter 14. In one embodiment, expandable balloon 362 extends three-hundred and sixty degrees (360°) radially around vial access housing 330. In one embodiment, a portion of toroidal expandable balloon 362 is not covered by pressure equalization housing 360. In this manner, expandable balloon 362 is capable of expanding in an axial direction.

In one embodiment, pressure equalization housing 360 and vial access housing 330 are a single integral component. In another embodiment, pressure equalization housing 360 and vial access housing 330 are separate components and pressure equalization housing 360 is attachable to vial access housing 330 such that significant relative movement between pressure equalization housing 360 and vial access housing 330 is prevented.

Referring to FIG. 4G, a pressure normalization channel 370 extends from second end 334 of vial access housing 330 to exit aperture 364 of pressure equalization housing 360. Pressure normalization channel 370 is arranged to provide gas communication between the expandable balloon 362 and the interior of a vial 90 when the vial adapter 14 is connected to a vial 90. With vial adapter 14 connected to a vial 90, a syringe or cannula assembly may be used to inject fluid into the vial 90 or to withdraw fluid therefrom as described in more detail below. In one embodiment, pressure normalization channel 370 extends from a portion of piercing tip 348 of spike member 346 and substantially parallel with fluid transfer channel 342 inside spike member 346. The pressure normalization channel 370 diverts in a direction perpendicular to fluid transfer channel 342 substantially at shoulder portion 372 of pressure normalization channel 370. The pressure normalization channel 370 includes an inlet opening 374 arranged substantially at a portion of piercing tip 348 of spike member 346 and an outlet opening 376 positioned substantially at exit aperture 364 of pressure equalization housing 360.

Referring to FIGS. 4A and 4G, in one embodiment, the pressure normalization channel 370 comprises a filter 380 arranged to cover a region of the pressure normalization channel 370. The filter 380 serves the purpose of preventing any fluid from a container such as a vial from reaching expansion chamber 366 of expandable balloon 362. In one embodiment, the filter 380 is preferably a hydrophobic filter which permits gas to pass but prevents liquid to pass. The filter 380 may be secured within pressure equalization housing 360 via filter holder 382.

In one embodiment, vial adapter 14 may also include a valve arrangement positioned in the proximity of outlet opening 376 of the pressure normalization channel 370. Such a valve arrangement prevents clogging of the filter 380 by providing a cracking pressure to the valve arrangement for the fluid which flows in a direction from the inlet opening 374 to the outlet opening 376 of the pressure normalization channel 370 while permitting preferably a minimal cracking pressure in the opposite direction.

The function and advantages of vial adapter 14 according to the present disclosure will be described in greater detail. When preparing and administering drugs care has to be taken to minimize, or preferably eliminate the risk of exposing people, such as medical and pharmacological personnel, to toxic substances. Some drugs must be dissolved or diluted before they are administered, which involves transferring a solvent from one container to a sealed vial containing the drug in powder or liquid form, by means of a needle, for example. Drugs may be inadvertently released into the atmosphere in gas form or by way of aerosolization, during the withdrawal of the needle from the vial and while the needle is inside the vial if any pressure differential between the interior of the vial and surrounding atmosphere exists. Vial adapter 14 of the present disclosure eliminates this problem by using pressure equalization system 314 of vial adapter 14 that may be attached to a vial during the preparation of drugs. The pressure equalization system 314 includes an expandable balloon 362 which is in communication with the interior of the vial 90 ensures that neither an increased pressure nor a vacuum can occur inside the vial 90 when gas or liquid is injected into or withdrawn from the vial 90. In one embodiment, the expandable balloon 362 may be filled with cleaned or sterilized air prior to its use to ensure that the contents of the vial 90 do not become contaminated with air-borne particles such as dust, pollen, mold or bacteria, or other undesirable substances.

Referring to FIGS. 12-15, the vial adapter 14 is assembled via its connection element 336 of vial access housing 330 to a cannula 20 of syringe adapter 12 which in turn can be connected to a fluid container, such as barrel assembly 16, and the vial adapter 14 is also assembled via its vial connection members 337 with a second fluid container, such as a vial 90. As vial adapter 14 is assembled with the vial 90, the piercing tip 348 of the spike member 346 is pierced through a septum 94 of the vial 90. Vial 90 may be a standard drug vial of any type having an open head portion covered by a pierceable septum of an elastomeric material. The walls 95 of vial 90 define a vial chamber 96 for containing a substance 98. The vial septum 94 is engaged with the head portion 93 of vial 90 to seal a substance within vial chamber 96. The plurality of vial grip members 338 fixedly connect vial adapter 14 to the vial 90 as the hook protrusions 340 of vial grip members 338 engage the corresponding flange 97 on vial 90 as shown in FIG. 7B. After assembly, a user is able to insert fluid into the vial 90, or optionally, to retract fluid from the vial 90.

Figure 18A:
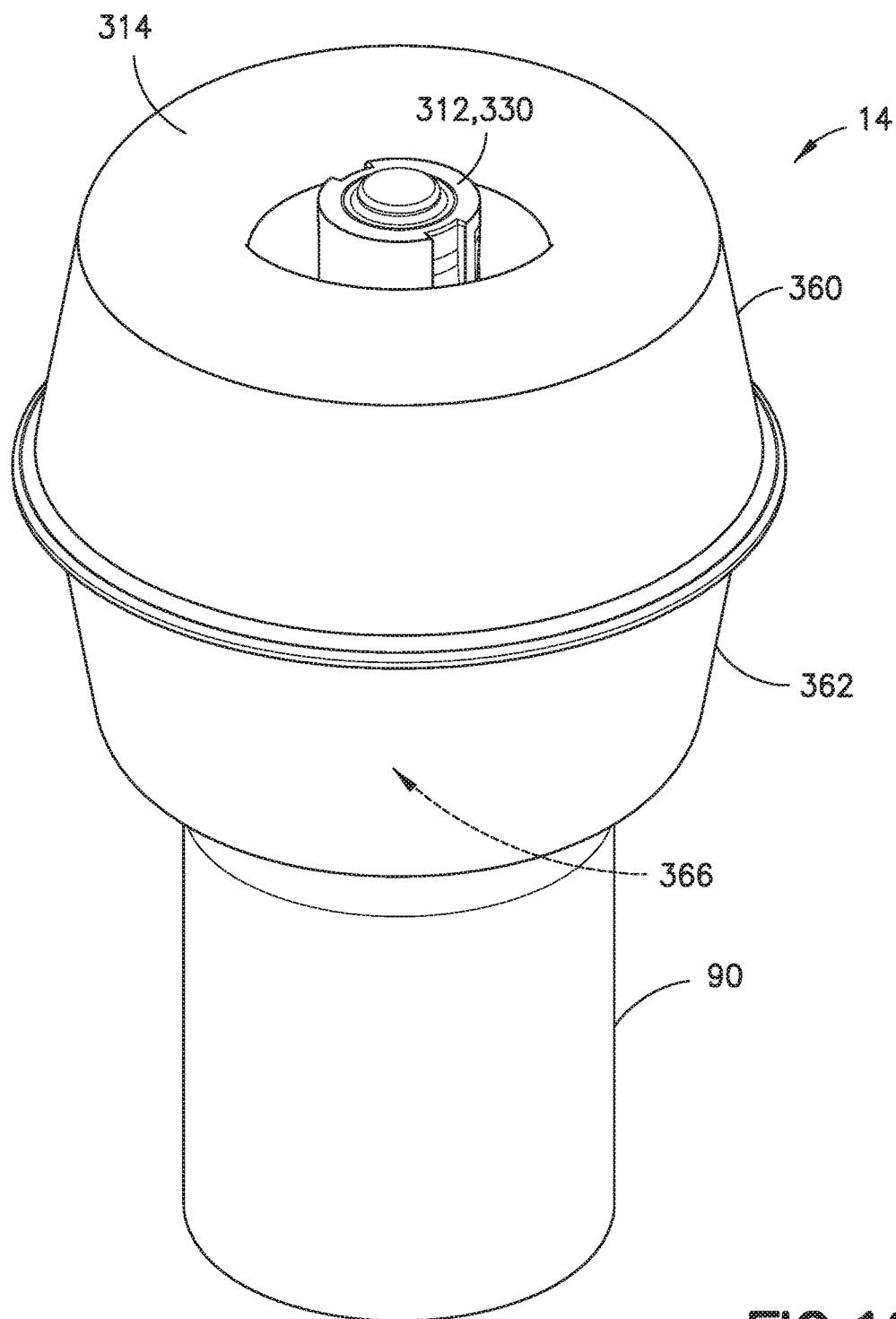
FIG. 18A is a perspective view of a vial adapter connected to a vial in accordance with an embodiment of the present invention.
Figure 18B:
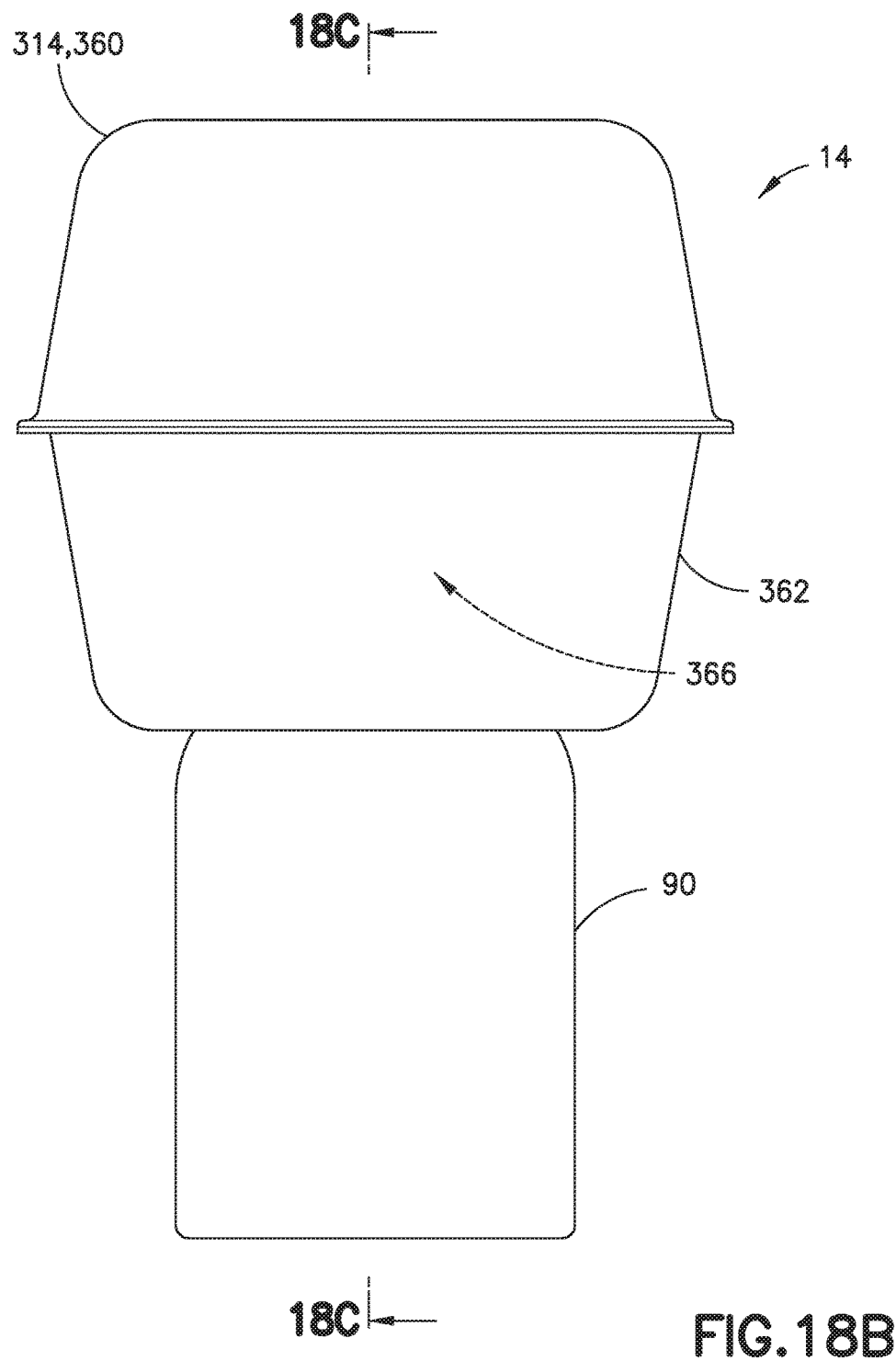
FIG. 18B is another perspective view of a vial adapter connected to a vial in accordance with an embodiment of the present invention.
Figure 18C:
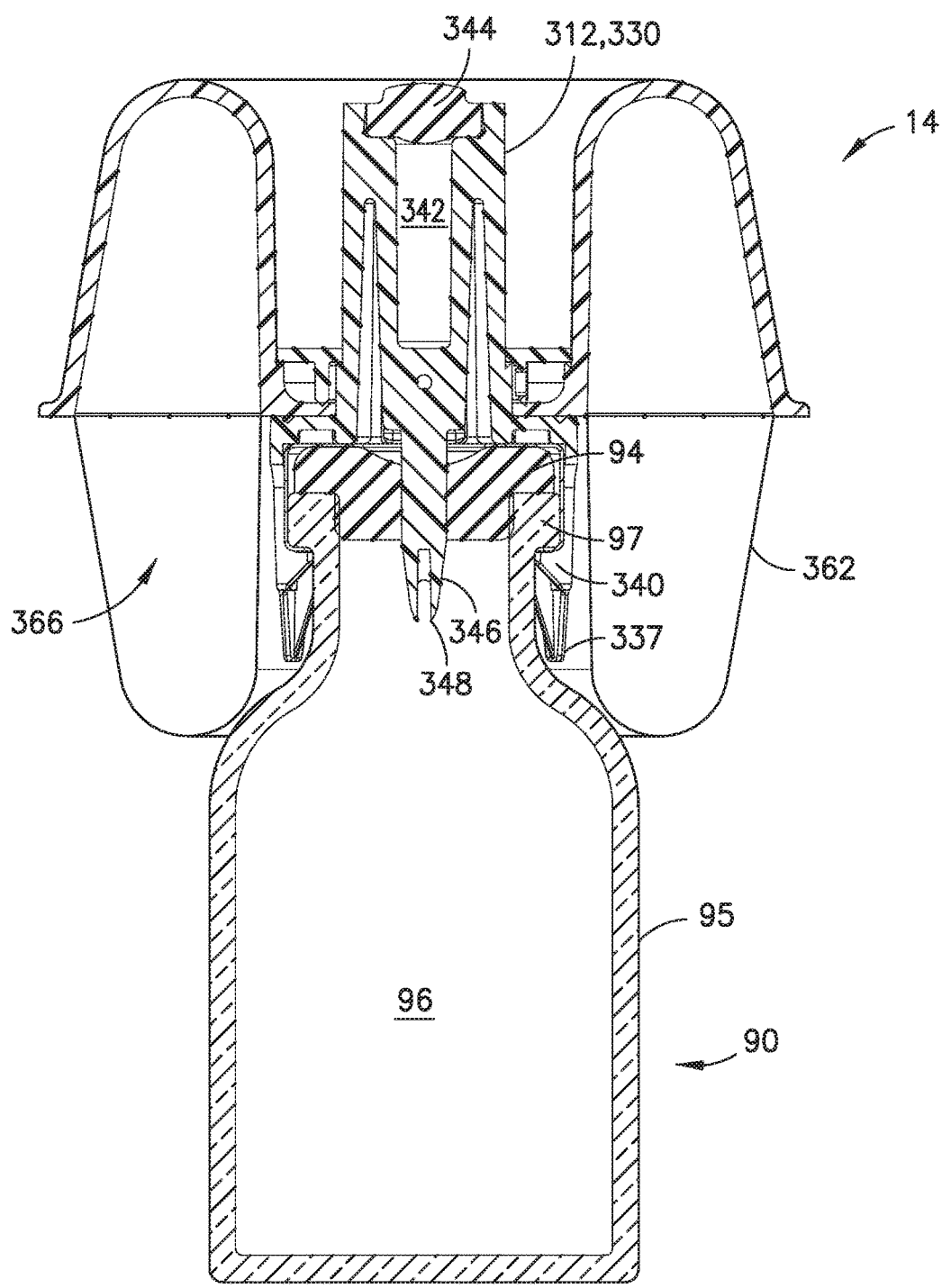
FIG. 18C is a cross-sectional view of a vial adapter connected to a vial taken along line 18C-18C of FIG. 18B in accordance with an embodiment of the present invention.
Figure 20A:
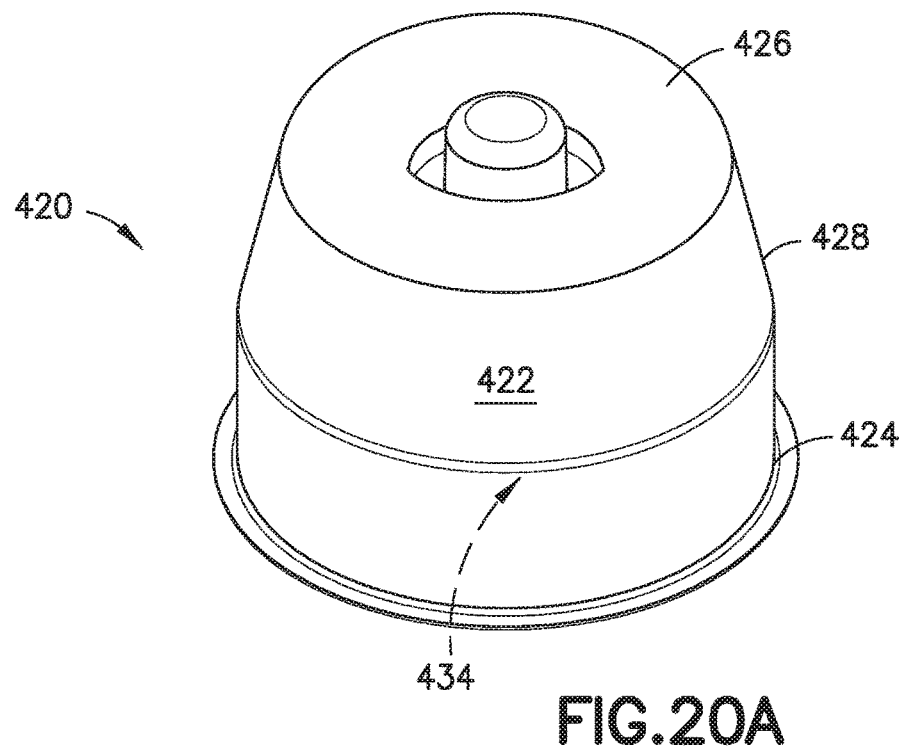
FIG. 20A is a perspective view of a packaging member in accordance with an embodiment of the present invention.
Figure 20B:
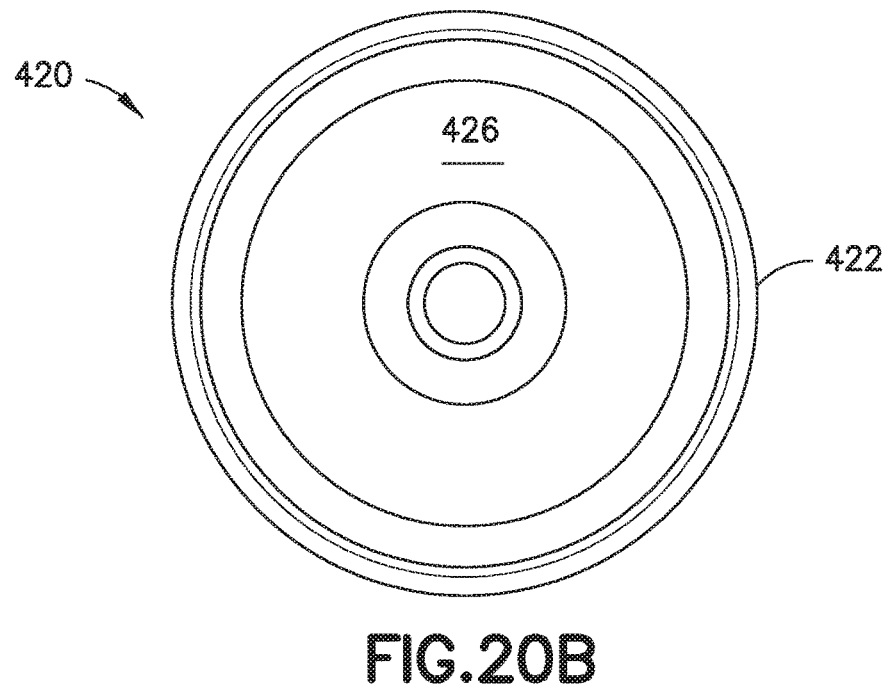
FIG. 20B is a bottom view of a packaging member in accordance with an embodiment of the present invention.
Figure 20C:
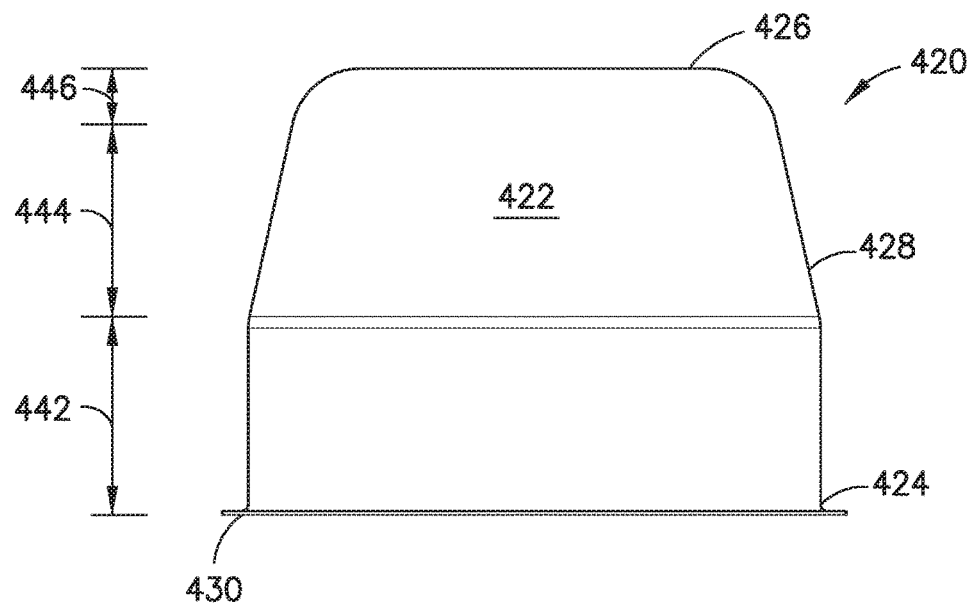
FIG. 20C is a side elevation view of a packaging member in accordance with an embodiment of the present invention.
Figure 20D:
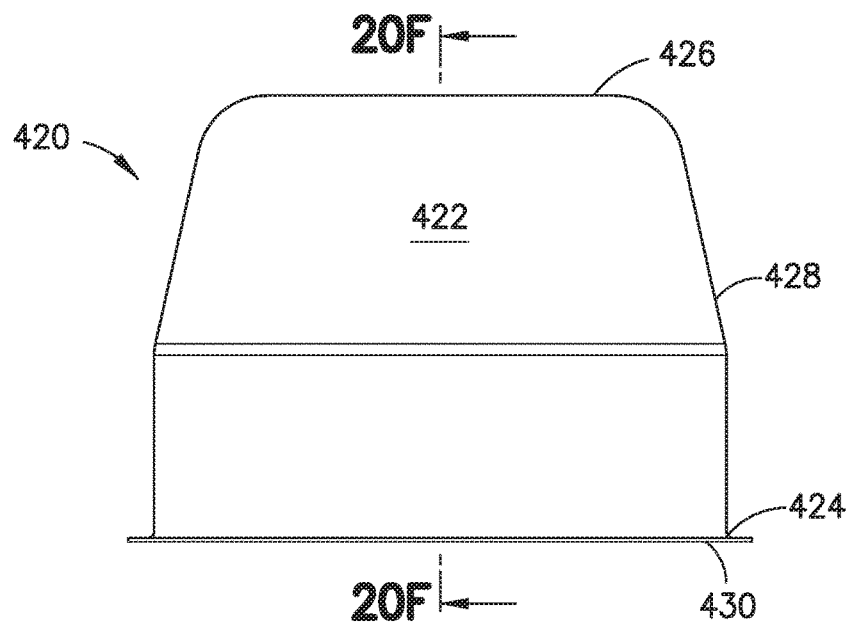
FIG. 20D is another side elevation view of a packaging member in accordance with an embodiment of the present invention.
Figure 20E:
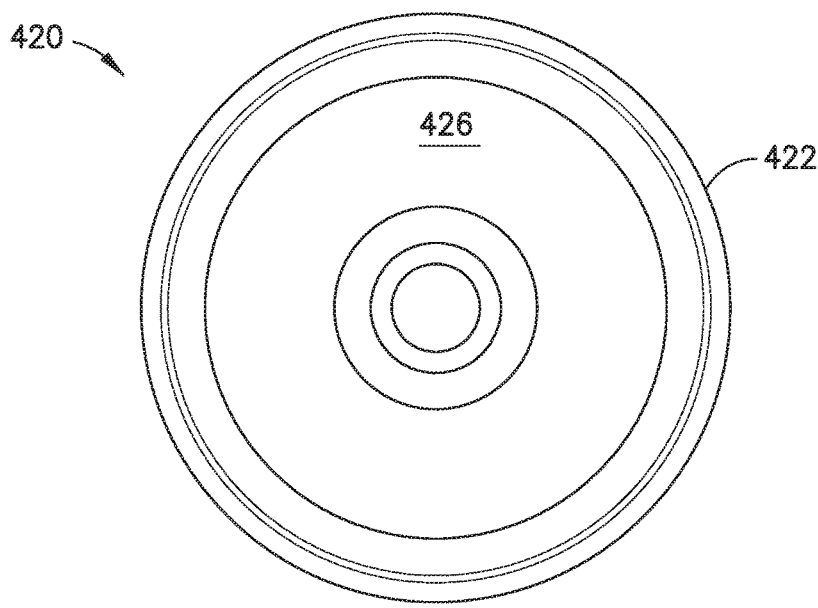
FIG. 20E is another bottom view of a packaging member in accordance with an embodiment of the present invention.
Figure 20F:
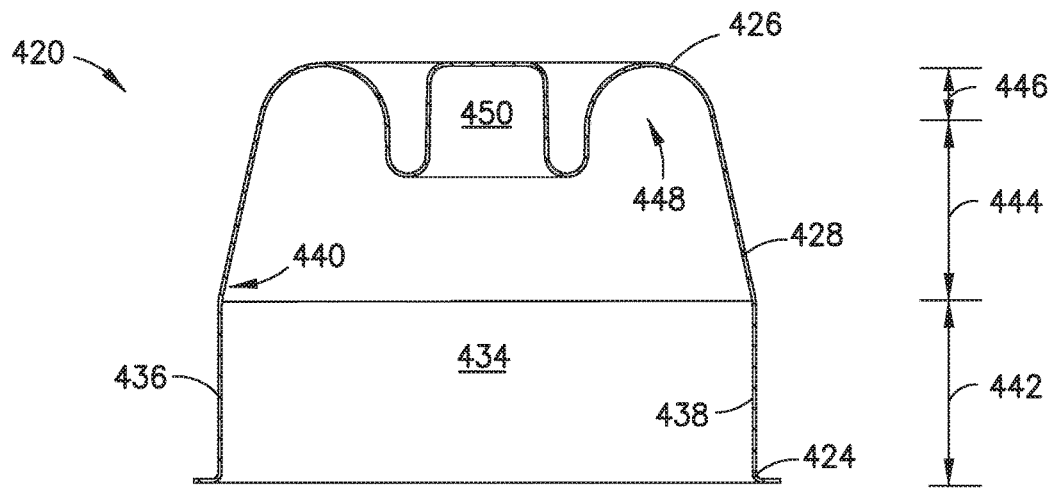
FIG. 20F is a cross-sectional view of a packaging member taken along line 20F-20F of FIG. 20D in accordance with an embodiment of the present invention.

As a fluid is inserted into the vial 90, using the cannula 20 and barrel assembly 16, an overpressure is created inside the vial 90. Pressure equalization system 314 of vial adapter 14 permits pressure equalization between the vial 90 and the expandable balloon 362. The pressure normalization channel 370 normalizes the pressure inside the vial 90 by relieving the pressure inside the vial 90 to the expansion chamber 366 of the expandable balloon 362 as shown in FIGS. 18A-18C.

In other words, FIGS. 12-16 and 18A-18C show the vial adapter 14 attached to the vial 90 and with cannula 20 inserted through the vial adapter 14 and into the interior of the vial 90. As a fluid is injected into the vial 90 or withdrawn from the vial 90, the pressure normalization channel 370 of the pressure equalization system 314 of vial adapter 14 permits gas to flow from the interior of the vial 90 into the expandable balloon 362 or from the expansion chamber 366 of the expandable balloon 362 to the vial 90, and thereby equalizes the pressure in the interior of the vial 90. Gas may enter the expandable balloon 362 via outlet opening 376, however, gas cannot exit from the expandable balloon 362. This eliminates, or at least reduces the risk, of any substance inside the vial 90 from being released into the atmosphere in gas form or by way of aerosolization during the insertion or withdrawal of a needle from the vial 90 or while a needle is inserted in the vial 90. It also eliminates, or reduces, the risk of the vial 90 deforming due to the increased pressure inside the vial 90, whereby such deformation may cause leakage of the vial's contents due to separation of the septum 94 of the vial 90 from the walls 95 of the vial 90, for example.

Figure 6:
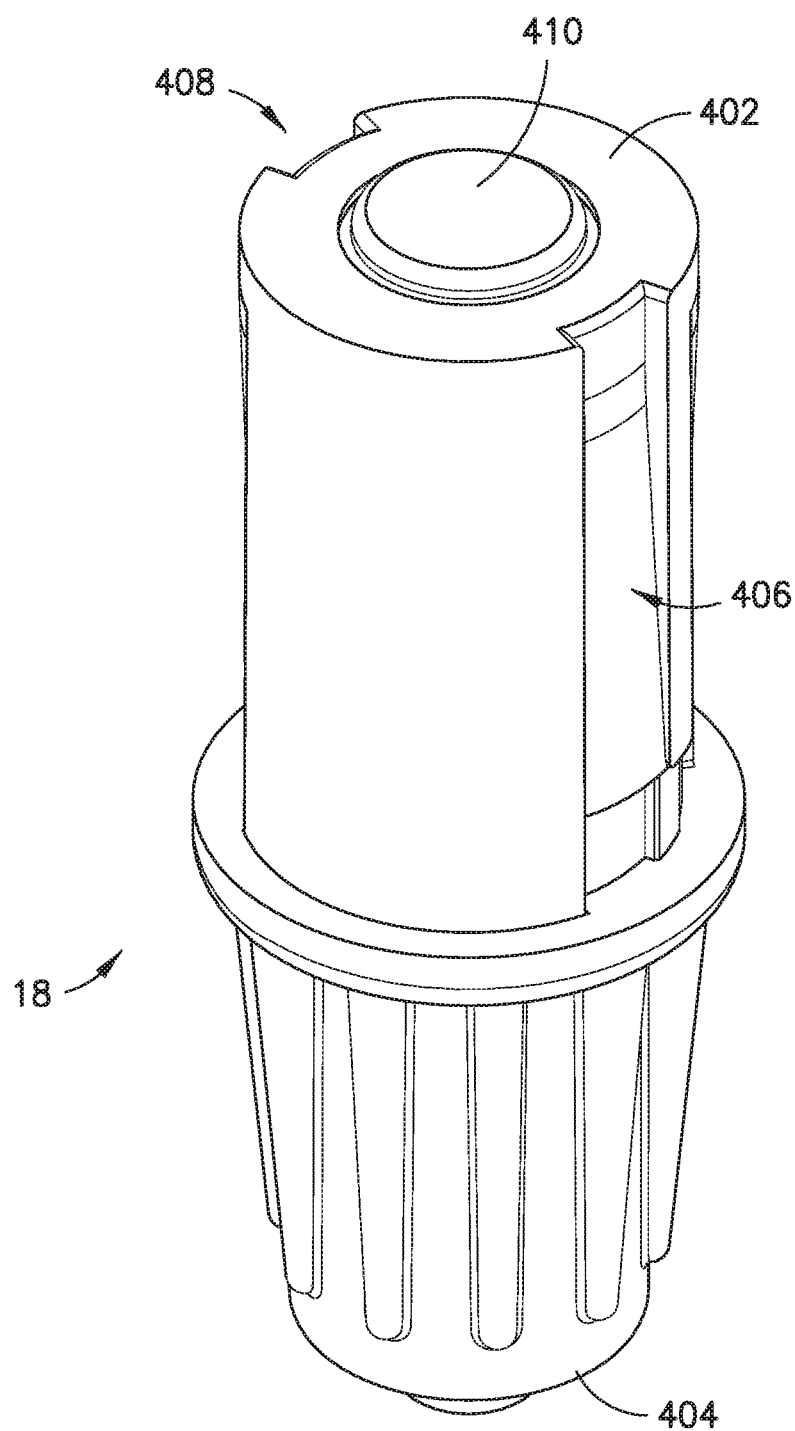
FIG. 6 is a perspective view of an intravenous line adapter in accordance with an embodiment of the present invention.

Referring to FIG. 6, IV line adapter 18 includes first end 402 and opposing second end 404. IV line adapter 18 provides a compact and accessible connector for connecting a cartridge or barrel containing a drug to an intravenous line or an injection apparatus for administering the drug to a patient.

First end 402 of IV line adapter 18 includes a connection element or connection system 406. First connection element 406 is engageable with a connection element 120, 122 of a syringe adapter 12 to secure the syringe adapter 12 to IV line adapter 18. In one embodiment, first end 402 of IV line adapter 18 includes a second connection element or second connection system 408. Second connection element 408 is spaced a distance from first connection element 406. In one embodiment, second connection element 408 is spaced approximately 180 degrees) (180° from first connection element 406. Second connection element 408 is engageable with a connection element 120, 122 of an syringe adapter 12 to secure the syringe adapter 12 to IV line adapter 18 such that significant relative movement between syringe adapter 12 and IV line adapter 18 is prevented.

First end 402 of IV line adapter 18 includes a pierceable barrier membrane 410. The pierceable barrier membrane 410 provides for a liquid and gas tight seal between a piercing member of a barrel assembly and the pierceable barrier membrane 410 during fluid transfer of a medication to a patient so to minimize leakage and thereby prevent exposure of hazardous medicaments to a user. Barrier membrane 410 provides a self-sealing seal that, with a barrel assembly attached to IV line adapter 18, provides a leak-proof seal preventing any substance being administered to a patient from being exposed to a health care provider administering the medication. In one embodiment, barrier membrane 410 comprises a resilient material. For example, barrier membrane 410 is preferably a unitary device molded of any flexible, elastomeric material conventionally used for fabricating gas-proof closures. Barrier membrane 410 may be formed of a natural rubber material, polyurethane elastomers, butyl rubbers, or similar materials.

Referring to FIGS. 10-18C, the use of system 10 to withdraw a medication such as substance 98 from vial 90 using a barrel assembly 16 such as a syringe will now be described. Initially, referring to FIG. 11, with vial adapter 14 attached to vial 90 as described above, a health care provider brings syringe adapter 12 attached to barrel assembly 16 to a position adjacent vial adapter 14. Next, referring to FIGS. 12B-14, with cannula seal 22 in communication with vial seal membrane 344 of vial adapter 14, cannula 20 pierces cannula seal 22 and vial seal membrane 344. Because cannula seal 22 is in communication with vial seal membrane 344, as cannula 20 pierces cannula seal 22, cannula 20 enters vial seal membrane 344. In this manner, cannula 20 is maintained in a leak-proof sealing system throughout the process of engaging cannula 20 with vial adapter 14 and vial 90.

For cannula 20 to pierce cannula seal 22, a force is applied to barrel assembly 16 in a direction generally along arrow A (FIG. 11). As cannula 20 is brought into contact with vial adapter 14, spring 24 and annular ribbed members 46 of cannula seal 22 are compressed as cannula 20 pierces cannula seal 22 and vial seal membrane 344. Compression of spring 24 creates a spring biasing force that is exerted on cannula seal 22 to elastically enclose cannula 20 simultaneously with cannula 20 exiting vial seal membrane 344 as discussed below. Furthermore, compression of annular ribbed members 46 of cannula seal 22 creates a cannula seal biasing force that is exerted on cannula seal 22 to elastically enclose cannula 20 simultaneously with cannula 20 exiting vial seal membrane 344 as discussed below.

As syringe adapter 12 is brought into engagement with vial adapter 14 as a force is applied to syringe adapter 12 in a direction generally along arrow A (FIG. 11), connection elements 120, 122 of syringe adapter 12 are snapped into engagement with connection system 336 of vial adapter 14. The connection between connection elements 120, 122 of syringe adapter 12 and connection system 336 of vial adapter 14 provides for quick and intuitive coupling and decoupling of syringe adapter 12 and vial adapter 14 through the use of a connection path and a disconnection path, the connection path being separate and distinct from the disconnection path. Furthermore, as connection elements 120, 122 of syringe adapter 12 are snapped into engagement with connection system 336 of vial adapter 14, the connection system provides audible and tactile connection feedback through the use of elastically deformable connection elements.

Next, referring to FIGS. 12B-15, cannula 20 pierces vial seal membrane 344 and vial septum 94 to place vial chamber 96 in fluid communication with barrel chamber 176 via cannula 20. Referring to FIG. 15, with vial chamber 96 in fluid communication with barrel chamber 176 via cannula 20, system 10 is inverted so that substance 98 contained within vial chamber 96 is brought into fluid communication with cannula 20 so that substance 98 may be transferred from vial chamber 96 to barrel chamber 176 via cannula 20.

With system 10 in the position shown in FIG. 15, stopper 164 is located adjacent distal end 172 of barrel 160 (as shown in FIG. 3B). When it is desired to aspirate or pull the fluid, such as substance 98, into barrel chamber 176 of barrel 160, a user moves flange portion 186 of plunger rod 162 in a direction generally along arrow B (FIG. 3B) and away from proximal end 174 of barrel 160 until the desired amount of substance 98 is pulled into barrel chamber 176 of barrel 160. In this manner, movement of plunger rod 162 actuates stopper 164 from a position adjacent distal end 172 of barrel 160 (as shown in FIG. 3B) towards a position adjacent proximal end 174 of barrel 160 to withdraw substance 98 from vial chamber 96 to barrel chamber 176 via cannula 20.

In this manner, movement of stopper 164 in the direction generally along arrow B (FIG. 3B) creates a vacuum inside barrel chamber 176. As the user moves stopper 164, via plunger rod 162 in the direction generally along arrow B, the user actively increases the volume within barrel chamber 176. Because the stopper 164 is sized relative to barrel 160 to provide sealing engagement with the interior wall of barrel 160, as described above, and because cannula 20 locked to distal end 172 of barrel 160 via needle hub 26 is placed in vial 90 containing fluid, no air can enter into barrel chamber 176 and, thus, the same number of air molecules are located within barrel chamber 176 as the user actively increases the volume within barrel chamber 176. This decreases the pressure in barrel chamber 176 relative to the air pressure outside of barrel 160. Therefore, a vacuum, i.e., a space of lower air pressure, is created to pull the fluid, such as substance 98, into barrel chamber 176. Advantageously, barrel assembly 16 can be used to collect a fluid into barrel chamber 176 or to expel a fluid out of barrel chamber 176 as will be described below.

In order to avoid creating a negative pressure within the vial chamber 96, air may be aspirated into the barrel chamber 176 prior to connection of the syringe adapter 12 with the vial adapter 14. In particular, when the plunger rod 162 is withdrawn, air will be drawn into the cannula 20 from the outside environment by passing through the intake filter 234, through an opening or passageway 242 in the needle hub 26 and thereby causing the extension 244 of the cannula seal 22 to deflect radially inward. After passing the extension 244 of the cannula seal 22, which acts as one-way valve 232, the air moves through the cannula seal 22, into the cannula 20, and then into the barrel chamber 176. After connection of the syringe adapter 12 to the vial adapter 14, as described above, the air within the barrel chamber 176 is injected into the vial chamber 96, passes through the pressure normalization channel 370 of the vial adapter 14, and into the expansion chamber 366 thereby causing the expandable balloon 362 to expand. Upon withdrawal of the fluid or substance 98 from the vial chamber 96, the air will be drawn from the expansion chamber 366 into the vial chamber 96, which prevents a negative pressure from being created within the vial chamber 96. The expandable balloon 362 will return to its unexpanded state when air is drawn back into the vial chamber 96. The volume of air aspirated into the barrel chamber 176 for injection into the vial chamber 96 preferably corresponds to the volume fluid intended to be removed from the vial chamber 96.

With the desired amount of substance 98 pulled into barrel chamber 176 of barrel 160, a user may now disengage cannula 20 from vial 90 as shown in FIG. 16.

Once it is desired to disconnect syringe adapter 12 from vial adapter 14, connection elements 120, 122 of syringe adapter 12 can be rotated in a counter-clockwise direction out of engagement with connection system 336 of vial adapter 14. With connection elements 120, 122 rotated out of engagement with connection system 336 of vial adapter 14, a pulling force may be exerted on syringe adapter 12 in a direction away from vial adapter 14 to pull syringe adapter 12 out from vial adapter 14.

System 10 of the present disclosure allows a user to disengage cannula 20 from vial 90 maintaining a leak-proof sealing. As discussed above, as cannula 20 is brought into contact with vial adapter 14, spring 24 and annular ribbed members 46 of cannula seal 22 are compressed as cannula 20 pierces cannula seal 22 and vial seal membrane 344. Compression of spring 24 creates a spring biasing force that is exerted on cannula seal 22 and compression of annular ribbed members 46 of cannula seal 22 creates a cannula seal biasing force that is exerted on cannula seal 22. Because cannula seal 22 is in communication with vial seal membrane 344 throughout a process of transferring substance 98 from vial chamber 96 to barrel chamber 176 via cannula 20, as cannula 20 is removed from vial 90 and vial seal membrane 344, the spring biasing force of spring 24 and the cannula seal biasing force of annular ribbed members 46 of cannula seal 22 are exerted on cannula seal 22 to elastically enclose cannula 20 simultaneously with cannula 20 exiting vial seal membrane 344. Advantageously, system 10 maintains a leak-proof seal enclosing cannula 20 at all times during engagement of cannula 20 with vial 90, during transfer of the substance 98 from vial chamber 96 to barrel chamber 176 via cannula 20, and during disengagement of cannula 20 from vial 90 to substantially prevent leakage of liquid or air from the system 10.

As discussed above, system 10 is also compatible with a drug reconstitution system. Certain drugs are preferably provided in powder or dry form (such as a lyophilized form), and require reconstitution prior to administration. Lyophilized drugs, for example, typically are supplied in a freeze-dried form that needs to be mixed with a diluent to reconstitute the substance into a form that is suitable for injection. In addition, drugs may be provided as multipart systems which require mixing prior to administration. For example, one or more liquid components, such as flowable slurries, and one or more dry components, such as powdered or granular components, may be provided in separate containers which require mixing prior to administration.

In one embodiment, barrel 160 contains a first substance or flowable substance (e.g., slurry or liquid) such as a diluent, and vial 90 contains a second substance, such as a powdered or granular substance intended for reconstitution. For example, barrel chamber 176 of barrel 160 may be adapted to contain a flowable material, such as a liquid diluent or other substance intended for drug reconstitution therein. The flowable material may be a liquid or slurry component of a drug or medicament. It is further understood that the flowable material may include one or more constituent elements (e.g., two different types of drug components) containing one or more pharmacologically active agents. Alternatively, the flowable material may serve solely as a diluent for a dry drug and contain no pharmacologically active elements.

In one embodiment, barrel chamber 176 of barrel 160 may be pre-filled with the liquid diluent or other substance intended for drug reconstitution. In this manner, barrel 160 can be manufactured, pre-filled with a diluent, sterilized, and packaged in appropriate packaging for delivery, storage, and use by the end user.

Vial 90 contains the second component of the drug to be reconstituted. The second drug component may be provided in powdered or granular form (e.g., a lyophilized powder). Alternatively, the second component is provided in a wet form, such as a liquid or slurry, for combination with the flowable material in barrel 160.

Referring to FIGS. 10-18C, the use of system 10 to reconstitute a first substance or liquid contained within barrel chamber 176 of barrel 160 with a second substance or powder contained within vial 90 will now be described. Initially, referring to FIG. 11, with vial adapter 14 attached to vial 90, a health care provider brings syringe adapter 12 attached to barrel assembly 16 to a position adjacent vial adapter 14. Next, referring to FIGS. 12B-14, with cannula seal 22 in communication with vial seal membrane 344 of vial adapter 14, cannula 20 pierces cannula seal 22 and vial seal membrane 344. Because cannula seal 22 is in communication with vial seal membrane 344, as cannula 20 pierces cannula seal 22, cannula 20 enters vial seal membrane 344. In this manner, cannula 20 is maintained in a leak-proof sealing system throughout the process of engaging cannula 20 with vial adapter 14 and vial 90.

As syringe adapter 12 is brought into engagement with vial adapter 14 as a force is applied to syringe adapter 12 in a direction generally along arrow A (FIG. 11), connection elements 120, 122 of syringe adapter 12 are snapped into engagement with connection system 336 of vial adapter 14. The connection between connection elements 120, 122 of syringe adapter 12 and connection system 336 of vial adapter 14 provides for quick and intuitive coupling and decoupling of syringe adapter 12 and vial adapter 14 through the use of a connection path and a disconnection path, the connection path being separate and distinct from the disconnection path. Furthermore, as connection elements 120, 122 of syringe adapter 12 are snapped into engagement with connection system 336 of vial adapter 14, the connection system provides audible and tactile connection feedback through the use of elastically deformable connection elements.

For cannula 20 to pierce cannula seal 22, a force is applied to barrel assembly 16 in a direction generally along arrow A (FIG. 11). As cannula 20 is brought into contact with vial adapter 14, spring 24 and annular ribbed members 46 of cannula seal 22 are compressed as cannula 20 pierces cannula seal 22 and vial seal membrane 344. Compression of spring 24 creates a spring biasing force that is exerted on cannula seal 22 to elastically enclose cannula 20 simultaneously with cannula 20 exiting vial seal membrane 344 as discussed below. Furthermore, compression of annular ribbed members 46 of cannula seal 22 creates a cannula seal biasing force that is exerted on cannula seal 22 to elastically enclose cannula 20 simultaneously with cannula 20 exiting vial seal membrane 344.

Next, referring to FIGS. 12B-15, cannula 20 pierces vial seal membrane 344 and vial septum 94 to place vial chamber 96 in fluid communication with barrel chamber 176 via cannula 20. At this point, the user presses down on plunger rod 162 in a direction generally along arrow C (FIG. 3B) advancing stopper 164 within barrel 160 from a position adjacent proximal end 174 of barrel 160 towards a position adjacent distal end 172 of barrel 160 to expel the liquid from barrel chamber 176 of barrel 160 and into vial 90 via cannula 20. As the liquid is expelled from barrel chamber 176 into the vial chamber 96, air within the vial chamber 96 is displaced by the incoming fluid and flows through the pressure normalization channel 370 of the vial adapter 14, and into the expansion chamber 366 thereby causing the expandable balloon 362 to expand. The expansion of the expandable balloon 362 prevents an increase in pressure within the vial chamber 96. Once the liquid is entirely injected into vial 90, the user may shake vial 90 to mix the dry and liquid components of the drug. In some embodiments, mixing may be accomplished in a matter of seconds whereas, in other embodiments, mixing can take as long as 20 minutes. The user can tell that all fluid has been expelled from barrel 160 when stopper 164 is at the base of barrel 160 and plunger rod 162 cannot be further advanced. The amount of mixing required is based on the composition, solubility, and viscosity of the dry and liquid components initially present in vial 90 and barrel 160 to be reconstituted.

Referring to FIG. 15, after the dry and liquid components are reconstituted in vial 90 and with vial chamber 96 in fluid communication with barrel chamber 176 via cannula 20, system 10 is inverted so that the reconstituted substance 98 contained within vial chamber 96 is brought into fluid communication with cannula 20 so that reconstituted substance 98 may be transferred from vial chamber 96 to barrel chamber 176 via cannula 20.

With system 10 in the position shown in FIG. 15, stopper 164 is located adjacent distal end 172 of barrel 160 (as shown in FIG. 3B). When it is desired to aspirate or pull the reconstituted substance 98 into barrel chamber 176 of barrel 160, a user moves flange portion 186 of plunger rod 162 in a direction generally along arrow B (FIG. 3B) and away from proximal end 174 of barrel 160 until the desired amount of reconstituted substance 98 is pulled into barrel chamber 176 of barrel 160. In this manner, movement of plunger rod 162 actuates stopper 164 from a position adjacent distal end 172 of barrel 160 (as shown in FIG. 3B) towards a position adjacent proximal end 174 of barrel 160 to withdraw reconstituted substance 98 from vial chamber 96 to barrel chamber 176 via cannula 20. Upon withdrawal of the substance 98 from the vial chamber 96, the air within the expansion chamber that was previously displaced by the fluid entering the vial chamber 96 will be drawn into the vial chamber 96, which prevents a negative pressure from being created within the vial chamber 96. The expandable balloon 362 will return to its unexpanded state when air is drawn back into the vial chamber 96.

With the desired amount of reconstituted substance 98 pulled into barrel chamber 176 of barrel 160, a user may now disengage cannula 20 from vial 90 as shown in FIG. 16. System 10 of the present disclosure allows a user to disengage cannula 20 from vial 90 maintaining a leak-proof sealing. As discussed above, as cannula 20 is brought into contact with vial adapter 14, spring 24 and annular ribbed members 46 of cannula seal 22 are compressed as cannula 20 pierces cannula seal 22 and vial seal membrane 344. Compression of spring 24 creates a spring biasing force that is exerted on cannula seal 22 and compression of annular ribbed members 46 of cannula seal 22 creates a cannula seal biasing force that is exerted on cannula seal 22. Because cannula seal 22 is in communication with vial seal membrane 344 throughout a process of transferring substance 98 from vial chamber 96 to barrel chamber 176 via cannula 20, as cannula 20 is removed from vial 90 and vial seal membrane 344, the spring biasing force of spring 24 and the cannula seal biasing force of annular ribbed members 46 of cannula seal 22 are exerted on cannula seal 22 to elastically enclose cannula 20 simultaneously with cannula 20 exiting vial seal membrane 344. Advantageously, system 10 maintains a leak-proof seal enclosing cannula 20 at all times during engagement of cannula 20 with vial 90, during transfer of the substance 98 from vial chamber 96 to barrel chamber 176 via cannula 20, and during disengagement of cannula 20 from vial 90 to substantially prevent leakage of liquid or air from the system 10.

When using system 10 to withdraw a medication such as substance 98 from vial 90 using a barrel assembly 16 and when using system 10 for a drug reconstitution procedure, as described above, care has be taken to minimize, or preferably eliminate, the risk of exposing people, such as medical and pharmacological personnel, to toxic substances. When preparing and administering drugs, drugs may be inadvertently released into the atmosphere in gas form or by way of aerosolization, during the withdrawal of the needle from the vial and while the needle is inside the vial if any pressure differential between the interior of the vial and surrounding atmosphere exists. As discussed above, vial adapter 14 of the present disclosure eliminates this problem by using pressure equalization system 314 of vial adapter 14 that may be attached to a vial during the preparation of drugs. The pressure equalization system 314 includes the expandable balloon 362 which in communication with the interior of the vial 90 ensures that neither an increased pressure nor a vacuum can occur inside the vial 90 when gas or liquid is injected into or withdrawn from the vial 90 as described above.

Referring to FIGS. 12-15, the vial adapter 14 is assembled to a cannula 20 of syringe adapter 12 which in turn is connected to barrel assembly 16 and the vial adapter 14 is also assembled to vial 90 as previously discussed. After assembly, a user is able to insert fluid into the vial 90, or optionally, to retract fluid from the vial 90. As a fluid is inserted into the vial 90, using the cannula 20 and barrel assembly 16, an overpressure is created inside the vial 90. Pressure equalization system 314 of vial adapter 14 permits pressure equalization between the vial 90 and the expandable balloon 362. The pressure normalization channel 370 normalizes the pressure inside the vial 90 by relieving the pressure inside the vial 90 to the expansion chamber 366 of the expandable balloon 362 as shown in FIGS. 18A-18C.

With the vial adapter 14 attached to the vial 90 and with cannula 20 inserted through the vial adapter 14 and into the interior of the vial 90, as a fluid is injected into the vial 90 or withdrawn from the vial 90, the pressure normalization channel 370 of the pressure equalization system 314 of vial adapter 14 permits gas to flow from the interior of the vial 90 into the expandable balloon 362 or from the expansion chamber 366 of the expandable balloon 362 to the vial 90, and thereby equalizes the pressure in the interior of the vial 90 and in the expansion chamber 366 of the expandable balloon 362. Gas may enter the expandable balloon 362 via outlet opening 376, however, gas cannot exit from the expandable balloon 362. This eliminates, or at least reduces, the risk of any substance inside the vial 90 from being released into the atmosphere in gas form or by way of aerosolization during the insertion or withdrawal of a needle from the vial 90 or while a needle is inserted in the vial 90. It also eliminates, or reduces, the risk of the vial 90 deforming due to the increased pressure inside the vial 90, whereby such deformation may cause leakage of the vial's contents due to separation of the septum 94 of the vial 90 from the walls 95 of the vial 90, for example.

Figure 17:
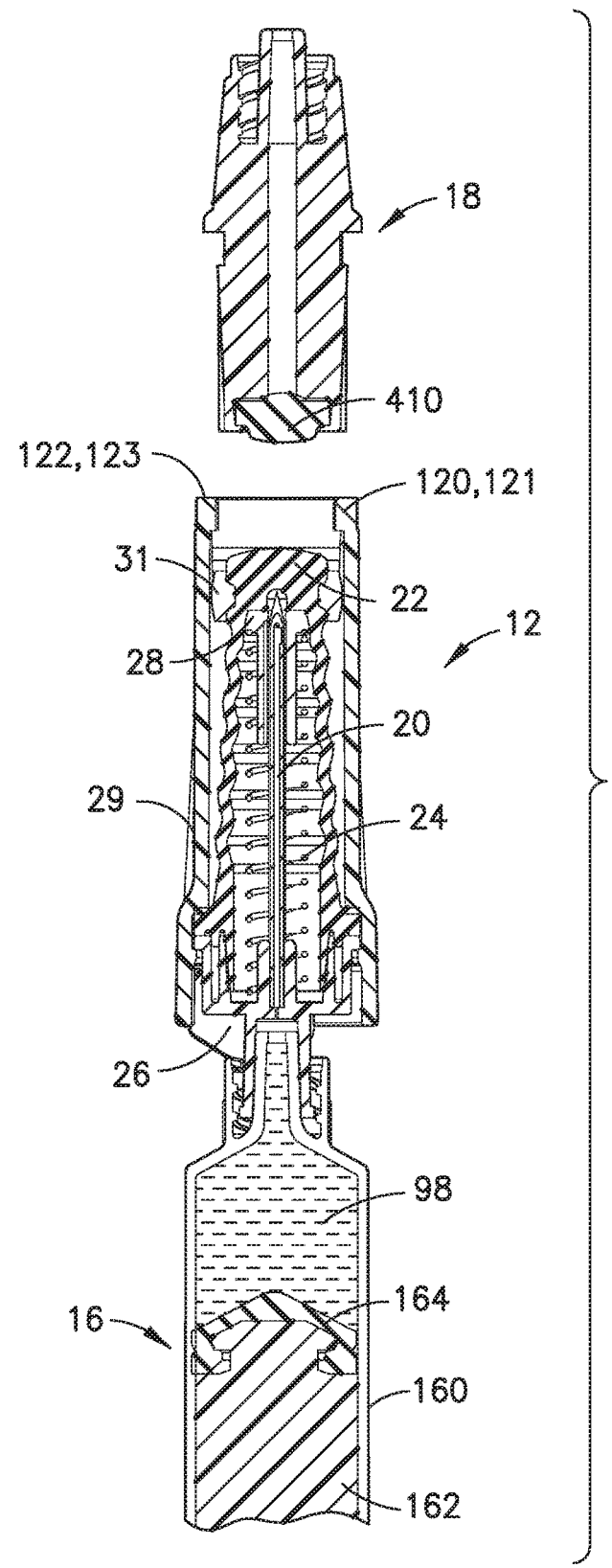
FIG. 17 is a cross-sectional view of the system of FIG. 16 with a portion of a substance contained within a vial chamber transferred to a barrel chamber via a cannula and the syringe adapter positioned adjacent an intravenous line adapter in accordance with an embodiment of the present invention.

After the desired amount of substance 98 is transferred into barrel chamber 176 of barrel assembly 16 and cannula 20 is disengaged from vial 90 as shown in FIGS. 16 and 17, a user may then use IV line adapter 18 to connect barrel assembly 16 containing a drug to an intravenous line or an injection apparatus for administering the drug to a patient.

Furthermore, although not shown, the system of the present disclosure may include a shielding arrangement or safety-lock mechanism to prevent unintended exposure of the cannula 20. The shielding arrangement may include a pivoting shielding member that is hinged to the needle hub 26 or other suitable area to selectively shield the distal end 30 of the cannula 20. The shielding arrangement may also include a cylinder or shielding member that is biased toward the distal end 30 of the cannula 20 to prevent movement of system 10. Any other suitable shielding or safety-lock mechanism may be utilized to prevent the unintended exposure of the cannula 20.

Referring to FIGS. 19-23C, an exemplary embodiment of a packaging system is shown. The present disclosure provides a packaging member for a vial adapter 14 having an exterior profile. The packaging member is sized and adapted to receive the vial adapter 14 therein and includes a sidewall that defines an interior profile, the interior profile of the packaging member being sized and shaped to substantially correspond to the exterior profile of the vial adapter 14. The packaging member of the present disclosure provides for a vial adapter 14 to be secured and contained within the packaging member using a taper lock and an interference connection to provide a secure fit therebetween, such that, with the vial adapter 14 received within the packaging member and with a sealing member removed from the packaging member, the packaging member can be used as an interface between the hand of a user and the vial adapter 14 so that the vial adapter 14 can be placed onto a vial 90 without taking the vial adapter 14 out of the packaging member.

Referring to FIGS. 20A-20F, 21, and 22, a system of the present disclosure further includes a packaging member 420 which is sized to receive vial adapter 14 therein. Packaging member 420 generally includes a packaging member body or shell 422 having a first or proximal end 424, a second or distal end 426, and a sidewall 428 extending between first end 424 and second end 426. First end 424 can be closed and sealed by a sealing member 430. Sealing member 430 includes a gripping area 432 and sealing member 430 is removably attachable to first or proximal end 424 of packaging member 420. Sidewall 428 defines an interior compartment 434 of packaging member 420. Interior compartment 434 is sized and adapted to receive vial adapter 14 therein as described in more detail below. Sidewall 428 includes an exterior wall surface 436 and an interior wall surface 438.

Interior wall surface 438 of sidewall 428 defines an interior profile 440 of packaging member 420. Sidewall 428 of packaging member 420 generally includes a cylindrical portion 442, a tapered portion 444, and a bottom arcuate portion 446, which together generally define a bell-shaped interior profile 440 of packaging member 420. In one embodiment, a set of packaging members 420 can be provided to accommodate vial adapters 14 of different sizes. Bottom arcuate portion 446 defines a pressure equalization system receiving portion 448 for receiving a portion of pressure equalization system 314 of vial adapter 14 and a vial access system receiving portion 450 for receiving a portion of vial access system 312 of vial adapter 14 as will be described in more detail below.

Figure 21:
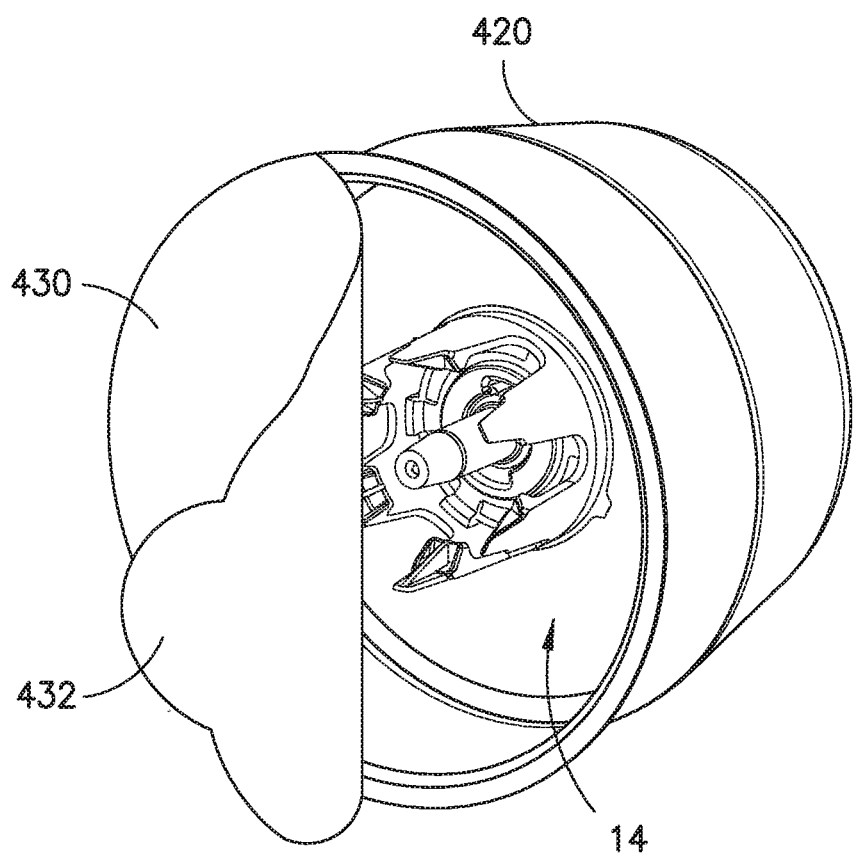
FIG. 21 is a perspective view of a vial adapter contained within a packaging member in accordance with an embodiment of the present invention.
Figure 22:
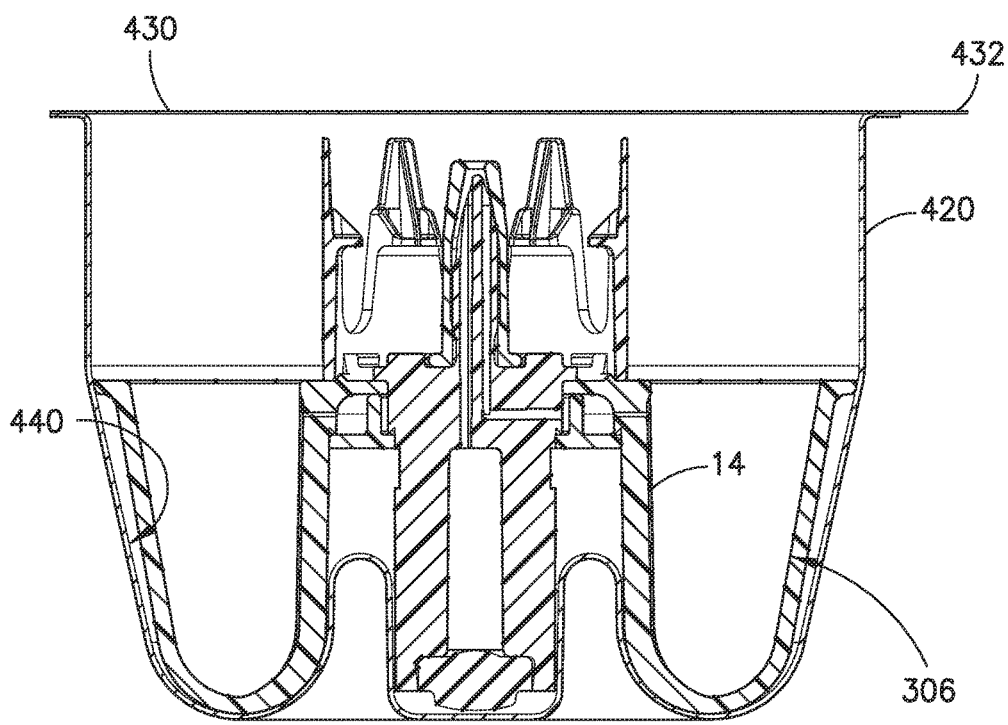
FIG. 22 is a cross-sectional view of a vial adapter contained within a packaging member in accordance with an embodiment of the present invention.

The fit between vial adapter 14 and packaging member 420 with vial adapter 14 received within interior compartment 434 of packaging member 420 will now be described. Referring to FIGS. 21 and 22, in an exemplary embodiment, vial adapter 14 is secured and contained within packaging member 420 using a taper lock and an interference connection to provide a secure fit therebetween, such that, as described below, with vial adapter 14 received within packaging member 420 and with sealing member 430 removed from packaging member 420, packaging member 420 can be used as an interface between the hand of a user and vial adapter 14 so that vial adapter 14 can be placed onto a vial without taking vial adapter 14 out of packaging member 420.

Vial adapter 14 is secured within packaging member 420 by an interference fit. As described above, wall 304 of vial adapter 14 defines an exterior profile 306 and interior wall surface 438 of sidewall 428 defines an interior profile 440 of packaging member 420. Referring to FIGS. 21 and 22, the interior profile 440 of packaging member 420 is sized and shaped to substantially correspond to the exterior profile 306 of vial adapter 14. Referring to FIG. 22, in one embodiment, the interior profile 440 of packaging member 420 is sized and shaped to substantially correspond to the exterior profile 306 of vial adapter 14, i.e., the interior profile 440 of packaging member 420 is sized and shaped to substantially correspond to the outward facing side portions of pressure equalization housing 360 of vial adapter 14, and the portions of packaging member 420 between pressure equalization system receiving portion 448 (FIG. 2F) and vial access system receiving portion 450 (FIG. 20F) do not need to correspond to all portions of vial adapter 14 as shown in FIG. 22. The above-described interference fit between vial adapter 14 and packaging member 420 is achieved by sizing and shaping the two mating parts, i.e., exterior profile 306 of vial adapter 14 and interior profile 440 of packaging member 420 so that interior profile 440 of packaging member 420 only slightly deviates dimensionally from exterior profile 306 of vial adapter 14. This ensures an interference fit which secures vial adapter 14 within packaging member 420 by a friction force after insertion of vial adapter 14 into packaging member 420. The taper lock and interference connection between vial adapter 14 and packaging member 420 is designed to not cause difficulty when removing packaging member 420 from vial adapter 14 after the engagement between vial adapter 14 and vial 90 is complete.

In one embodiment, pressure equalization housing 360 may include a plurality of stabilizing ribs 365 to provide an additional interference fit mechanism between vial adapter 14 and packaging member 420. Stabilizing ribs 365 provide contact with the interior wall surface 438 of packaging member 420 to provide an additional friction force between vial adapter 14 and packaging member 420 after insertion of vial adapter 14 into packaging member 420.

Additionally, vial adapter 14 is secured within packaging member 420 by means of complementary locking tapers on tapered exterior wall portion 361 of pressure equalization housing 360 and tapered portion 444 of packaging member 420. In one embodiment, tapered exterior wall portion 361 of pressure equalization housing 360 and tapered portion 444 of packaging member 420 have approximately equal respective tapers with an approximately equal included angle of taper, i.e., tapered exterior wall portion 361 of pressure equalization housing 360 and tapered portion 444 of packaging member 420 form complementary locking tapers.

Referring to FIGS. 21 and 22, packaging of vial adapter 14 within packaging member 420 will now be described. Initially, vial adapter 14 and packaging member 420 are sterilized according to techniques known to those of ordinary skill in the art. Next, vial adapter 14 is inserted into interior compartment 434 of packaging member 420 such that pressure equalization housing 360 of vial adapter 14 is received within pressure equalization system receiving portion 448 of packaging member 420 and first end 332 of vial access housing 330 is received within vial access system receiving portion 450. As described above, with vial adapter 14 properly positioned within packaging member 420, vial adapter 14 is secured and contained within packaging member 420 using a taper lock and an interference connection to provide a secure fit therebetween.

With vial adapter 14 properly inserted into interior compartment 434 of packaging member 420, sealing member 430 may be secured to first end 424 of packaging member 420 to seal vial adapter 14 within packaging member 420, i.e., sealing member 430 provides a substantially impermeable enclosure with respect to packaging member 420, provides a leak prevention and protection enclosure, protects the contents of vial adapter 14 contained within packaging member 420, and/or maintains a sealed, sterilized environment within packaging member 420. Sealing member 430 of packaging member 420 provides a sufficient seal at a range of temperatures, pressures, and humidity levels. In one embodiment, sealing member 430 provides a seal member that may be penetrated by ethylene oxide gas for product sterilization purposes. In one embodiment, tamper evidence is also provided by use of a tear strip or other indicating means secured to a portion of sealing member 430 and/or packaging member 420 to indicate tampering with the contents of packaging member 420.

Figure 23A:
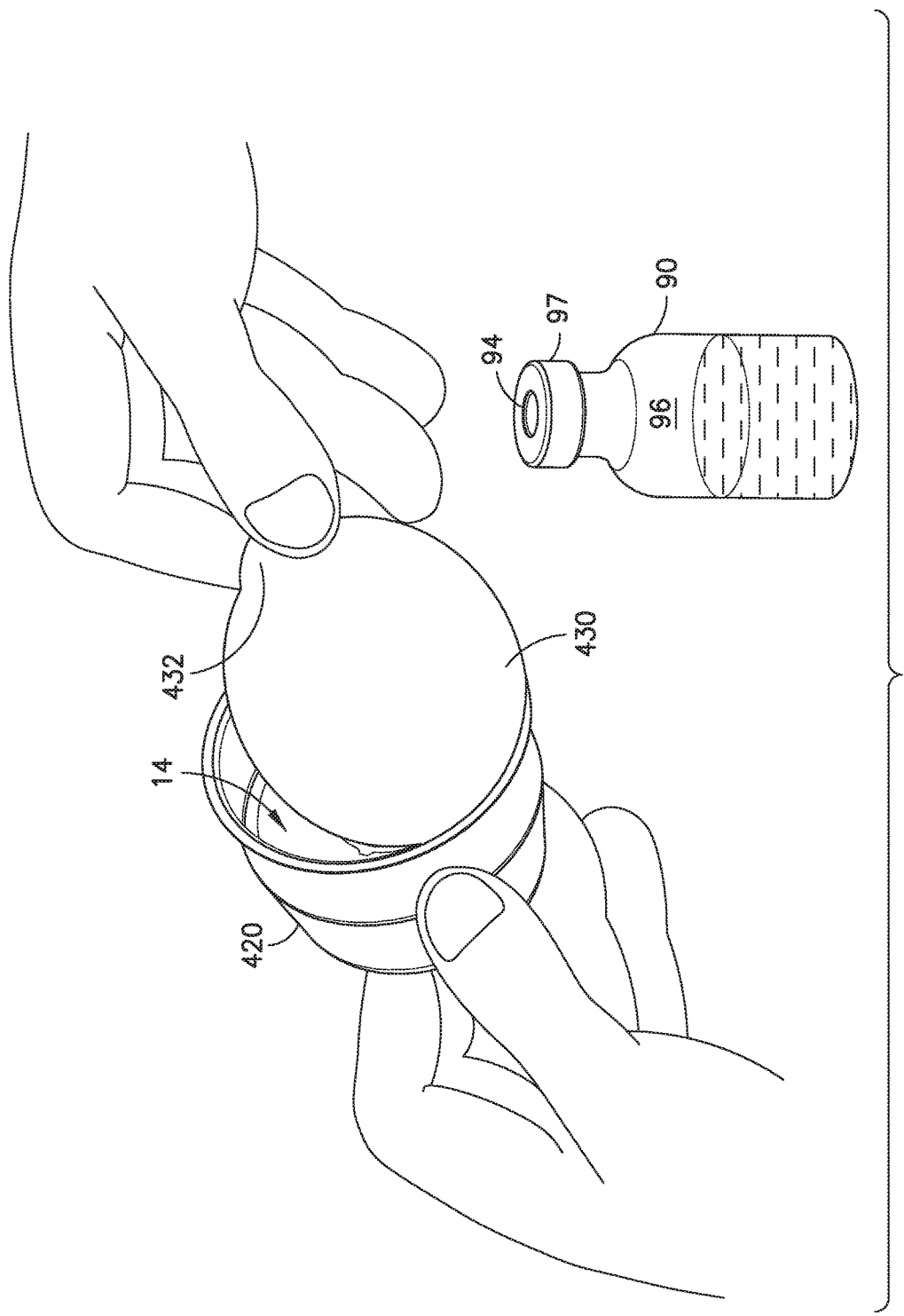
FIG. 23A is a perspective view of a first step of using a system of the present disclosure in accordance with an embodiment of the present invention.
Figure 23C:
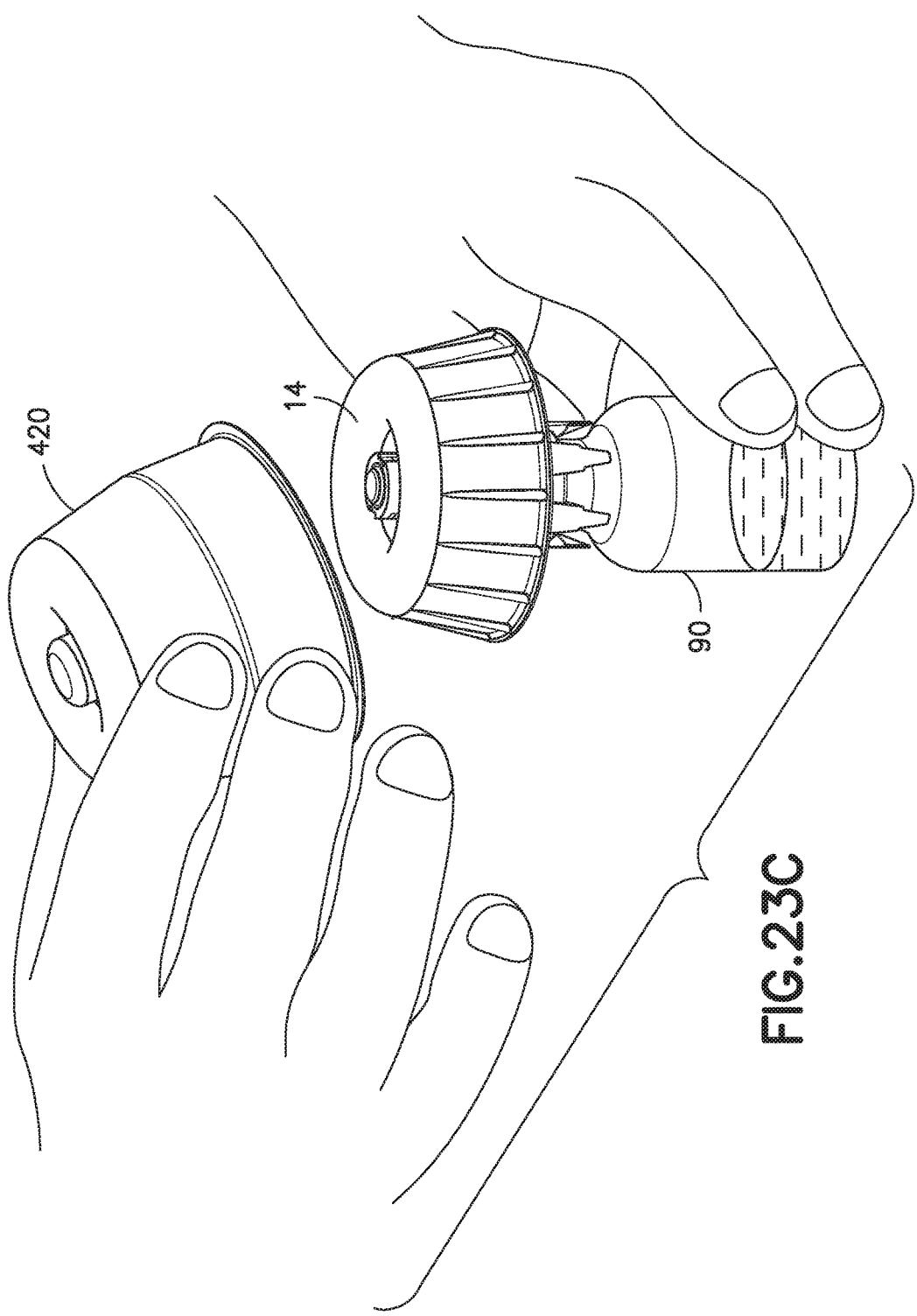
FIG. 23C is a perspective view of a third step of using a system of the present disclosure in accordance with an embodiment of the present invention.

Referring to FIGS. 23A-23C, the use of packaging member 420 to engage vial adapter 14 with a vial will now be described. Referring to FIG. 23A, with vial adapter 14 properly positioned within packaging member 420 and with sealing member 430 secured to first end 424 of packaging member 420 to seal vial adapter 14 within packaging member 420, when it is desired to use and place vial adapter 14 onto a drug vial 90, the sealing member 430 can be gripped at gripping area 432 and removed.

Next, packaging member 420 can be used as an interface between the hand of a user and vial adapter 14 so that vial adapter 14 can be placed onto a vial 90 without taking vial adapter 14 out of packaging member 420. Referring to FIG. 23B, packaging member 420 can be rotated downward so that second end 334 of vial access housing 330 is facing vial 90, i.e., vial connection member 337 of vial access housing 330 is engageable with a vial 90 while vial adapter 14 is received within interior compartment 434 of packaging member 420. Due to the vial adapter 14 being secured and contained within packaging member 420 using a taper lock and an interference connection to provide a secure fit therebetween as described above, vial adapter 14 does not fall out of packaging member 420 when packaging member 420 is rotated downward to face vial 90. The taper lock and interference connection between vial adapter 14 and packaging member 420 is designed to not cause difficulty when removing packaging member 420 from vial adapter 14 after the engagement between vial adapter 14 and vial 90 is complete.

With packaging member 420 rotated downward so that second end 334 of vial access housing 330 is facing vial 90 as shown in FIG. 23B, the vial connection member 337 of second end 334 of vial access housing 330 is directly engageable with vial 90 while vial adapter 14 is still received and maintained within interior compartment 434 of packaging member 420. Referring to FIG. 23C, with vial adapter 14 engaged with vial 90, a user may then remove packaging member 420 from vial adapter 14. The engagement between vial adapter 14 and vial 90 provides a resistance force that allows the taper lock and interference connection between vial adapter 14 and packaging member 420 to be overcome by a pulling force exerted by a user while the vial adapter 14 is maintained in engagement with vial 90.

In this manner, packaging member 420 allows for vial adapter 14 to be placed onto a drug vial without ever contacting vial adapter 14 thereby ensuring vial adapter 14 is maintained in a sterile environment and does not contact any contaminates. Typical packaging requires a vial adapter to be taken out of the packaging before engaging the vial adapter with a drug vial. For this reason, removal of a vial adapter from typical packaging requires direct contact with the vial adapter. Such contact with a vial adapter may contaminate the vial adapter and adds an additional step to a vial access procedure. Thus, packaging member 420 of the present disclosure maintains vial adapter 14 in a sterile environment and eliminates the step of removing the vial adapter from the packaging before engaging the vial adapter to a vial.

In one embodiment, packaging member 420 may also serve as a protective cap for multi-use vials between use cycles. When packaging member 420 is used as a protective cap, relevant medical information such as expiration date or time can be written directly onto the exterior surface of sidewall 428 of packaging member 420.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A syringe adapter comprising:
   a cannula attachable to a first container having a first chamber such that the cannula is in fluid communication with the first chamber of the first container;
   a syringe adapter housing including a first connection element, the first connection element engageable with a second connection element of a vial adapter to secure the syringe adapter to the vial adapter;

a cannula seal comprising a resilient sleeve enclosing at least a portion of the cannula, the cannula seal disposed within the syringe adapter housing;

a spring disposed over the cannula such that the spring is positioned between the cannula and the cannula seal, wherein the spring provides a biasing force;

an intake air filter disposed within the syringe adapter housing; and a gliding ring positioned at least partially between the cannula seal and the syringe adapter housing, wherein the gliding ring is spaced from the spring.

2. The syringe adapter of claim 1, wherein the syringe adapter housing includes a first end, a second end, and a sidewall extending therebetween, the sidewall having an exterior surface and an interior surface, the interior surface of the sidewall having the first connection element.

3. The syringe adapter of claim 1, wherein the gliding ring is secured to a distal end of the cannula seal.

\* \* \* \* \*